US007015372B2

(12) United States Patent
Preuss et al.

(10) Patent No.: US 7,015,372 B2
(45) Date of Patent: *Mar. 21, 2006

(54) PLANT ARTIFICIAL CHROMOSOME COMPOSITIONS AND METHODS

(75) Inventors: Daphne Preuss, Chicago, IL (US); Gregory Copenhaver, Oak Park, IL (US)

(73) Assignee: University of Chicago, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 10/161,849

(22) Filed: Aug. 6, 2002

(65) Prior Publication Data

US 2006/0003449 A1    Jan. 5, 2006

Related U.S. Application Data

(63) Continuation of application No. 09/553,231, filed on Apr. 19, 2000, now Pat. No. 6,900,012, which is a continuation of application No. 09/090,051, filed on Jun. 3, 1998, now Pat. No. 6,156,953.

(60) Provisional application No. 60/073,741, filed on Feb. 5, 1998, provisional application No. 60/048,451, filed on Jun. 3, 1997.

(51) Int. Cl.
| A01H 1/00 | (2006.01) |
| A01H 11/00 | (2006.01) |
| A01H 5/00 | (2006.01) |
| C12N 15/32 | (2006.01) |
| C12N 15/87 | (2006.01) |

(52) U.S. Cl. ............... 800/278; 800/279; 800/281; 800/283; 800/284; 800/289; 800/292; 800/293; 800/294; 800/295; 800/298; 435/6; 435/91.1

(58) Field of Classification Search .......... 435/6, 435/91.1; 800/260, 268, 278, 279, 281, 283, 800/284, 289, 292, 293, 294, 295, 298, 306
See application file for complete search history.

(56) References Cited

U.S. PATENT DOCUMENTS

| 4,889,806 A | 12/1989 | Olson et al. ............. 435/172.3 |
| 5,270,201 A | 12/1993 | Richards et al. ......... 435/240.4 |
| 5,288,625 A | 2/1994 | Hadlaczky ............... 435/172.2 |
| 5,695,967 A | 12/1997 | Van Bokkelen et al. ... 435/91.1 |
| 5,712,134 A | 1/1998 | Hadlaczky ............... 435/172.2 |
| 5,721,118 A | 2/1998 | Scheffler ................... 435/69.1 |
| 5,869,294 A | 2/1999 | Harrington et al. ........ 435/91.1 |
| 5,891,691 A | 4/1999 | Hadlaczky .................. 435/325 |
| 6,156,953 A * | 12/2000 | Preuss ....................... 800/278 |
| 6,162,963 A | 12/2000 | Kucherlapati et al. ........ 800/18 |

FOREIGN PATENT DOCUMENTS

WO    WO 89/09219    10/1989

OTHER PUBLICATIONS

Rugh, C.L. et al., "Mercuric ion reduction and resistance in transgenic *Arabidopsis thaliana* plants expressing a modified bacterial merA gene", PNAS, vol. 93, pp. 3182-3187 (1996).*

Siemens, J. et al., "Production and characterization of somatic hybrids between *Arabidopsis thaliana* and *Brassica nigra*", Plan Science, vol. 111, pp. 95-106 (1995).*

Abel et al., "Delay of disease development in transgenic plants that express the tobacco mosaic virus coat protein gene," *Science* 22:738-743, 1986.

Alfenito et al., "Molecular characterization of a maize B chromosome centric sequence," *Genetics*, 135:589-597, 1993.

Allshire, "Centromeres, checkpoints and chromatoid cohesion," *Genetics and Devel.*, 7:264-273, 1997.

Alonso-Blanco et al., "Development of an AFLP based linkage map of Ler, Col and Cvi *Arabidopsis thaliana* ecotypes and construction of a Ler/Cvi recombinant inbred line population," *J. Plant*, 14(2):259-271, 1998.

Baum et al., "The centrometric K-type repeat and the central core are together sufficient to establish a functional *Schizosaccharomyces pombe* centromere," *Mol. Bio. Cell.*, 5:747-761, 1994.

Bell et al., "Assignment of 30 microsatellite loci to the linkage map of *Arabidopsis*," *Genomics*, 19:137-144, 1994.

Birchler, "Do these sequences make CENs yet?" *Genome Res.*, 7:1035-1037, 1997.

Bloom, "The centromere frontier: Kinetochore components, microtubule-based motility, and the CEN-value paradox," *Cell*, 73:621-624, 1993.

Brown et al., "Mini-chromosomes derived from the human Y chromosome by telomere directed chromosome breakage, " *Proc. Natl. Acad. Sci. USA*, (93):7125-7130, 1996.

Burke et al., "Cloning of large segments of exogenous DNA into yeast by means of artificial chromosome vectors," *Science*, 236:806-812, 1987.

Capecchi, "High efficiency transformation by direct microinjection of DNA into cultured mammalian cells," *Cell* 22(2):479-488, 1980.

Carbon and Clarke, "Structural and functional analysis of a yeast centromere (CEN 3)," *Journal Cell Science*, Suppl. 1:43-58, 1984.

(Continued)

Primary Examiner—Jeffrey Fredman
Assistant Examiner—Teresa Strzelecka
(74) Attorney, Agent, or Firm—Marshall, Gerstein & Borun LLP

(57) ABSTRACT

The present invention provides for the identification and cloning of functional plant centromeres in *Arabidopsis*. This will permit construction of stably inherited plant artificial chromosomes (PLACs) which can serve as vectors for the construction of transgenic plant and animal cells. In addition, information on the structure and function of these regions will prove valuable in isolating additional centromeric and centromere related genetic elements and polypeptides from other species.

16 Claims, 40 Drawing Sheets

OTHER PUBLICATIONS

Carbon et al., "Centromere structure and function in budding and fission yeasts," *New Biologist*, 2:10-19, 1990.

Chang et al., "Restriction fragment length polymorphism linkage map for *Arabidopsis thaliana*," *Proc. Natl. Acad. Sci., USA*, 85:6856-6860, 1988.

Choo, "Turning on the centromere," *Nature Gene*, 18:3-4, 1998.

Christou et al., "Stable transformation of soybean callus by DNA-coated gold particles," *Plant Physiol.*, 87:671-674, 1988.

Chu et al., "Separation of large DNA molecules by contour-clamped homogeneous electric fields," *Science*, 234:1582-1585, 1986.

Clarke et al., "Analysis of centrometric DNA in the fission yeast *Schizosaccharomyces pombe*," *Proc. Natl. Acad. Sci. USA*, 83:8253-8257, 1986.

Clarke et al., "Isolation of a yeast centromere and construction of functional small circular chromosomes," *Nature*, 287:504-509, 1980.

Clarke, "Centromeres: proteins, protein complexes, and repeated domains at centromeres of simple eukaryotes," *Genetics and Development*, 8:212-218, 1998.

Copenhaver et al., "Assaying genome-wide recombination and centromere functions with *Arabidopsis* terads," *Proc. Natl. Acad. Sci. USA*, 95:247-252, 1998.

Depicker et al., "A negative selection scheme for tobacco protoplast-derived cells expressing the T-DNA gene 2," *Plant Cell Reports*, 7:63-66, 1988.

du Sart et al., "A functional neo-centromere formed through activation of a latent human centromere and consisting of non-alpha-satellite DNA," *Nature Gene.*, 16:144-153, 1997.

Earnshaw et al., "Proteins of the inner and outer centromere of mitotic chromosomes," *Genome*, 31:541-552, 1989.

Earnshaw, "When is a centromere not a kinetochore?," *J. Cell Sci.*, 99:1-4, 1991.

Fransz et al., "Cytogenetics for the model system *Arabidopsis thaliana*," *J. Plant*, 13(6):867-876, 1998.

Frary et al., "Molecular mapping of the centromeres of tomato chromosomes 7 and 9," *Mol. Gen. Genet.*, 250:295-304, 1996.

Fromm et al., "Expression of genes transferred into monocot and dicot plant cells by electroporation," *Proc. Natl. Acad. Sci. USA* 82(17):5824-5828, 1985.

Grill and Somerville, "Construction and characterization of a yeast artificial chromosome library of *Arabidopsis* which is suitable for chromosome walking," *Mol. Gen. Genet,.* 226:484-490, 1991.

Hadlaczky et al., "Centromere formation in mouse cells cotransformed with human DNA and a dominant marker gene," *Proc. Natl. Acad. Sci. USA*, 88:8106-8110, 1991.

Harrington et al., "Formation of de novo centromeres and construction of first-generation human artificial microchromosomes," *Nature Genetics*, 15:345-355, 1997.

Hegemann et al., "The centromere of budding yeast," *Bioassays*, 15(7):451-460, 1993.

Hwang et al., Identification and map position of YAC clones comprising one-third of the *Arabidopsis* genome, *The Plant Journal*, 1:367-374, 1991.

Ikeno et al., "Construction of YAC-based mammalian artificial chromosomes," *Nature Biotech.*, 16:431-439, 1998.

International Search Report dated Oct. 28, 1998 (PCT/US98/11288)(ARCD:257P).

Kaszas and Birchler, "Misdivision analysis of centromere structure in maize," *J. EMBO*, 15(19):5248-5256, 1996.

Klein et al., "High-velocity microprojectiles for delivering nucleic acids into living cells," *Nature*, 327:70-73, 1987.

Klein et al., "Stable genetic transformation of intact Nicotiana cells by the particle bombardment process," *Proc. Nat'l Acad. Sci. USA*, 85:8502-8505, 1988.

Konieczny et al., "A procedure for mapping *Arabidopsis* mutations usiing codominant ecotype-specific PCR-based markers," *The Plant Journal*, 4:403-410, 1993.

Koorneef et al., "Trisomics in *Arabidopsis thaliana* and the location of linkage groups," *Genetica*, 61:41-46, 1983.

Koorneef, "Linkage map of *Arabidopsis thaliana*," *J. Heredity*, 74:265-272, 1983.

Koorneef, The use of telotrisomics for centromere mapping in *Arabidopsis thaliana* (L.) Heynh, *Genetica*, 62:33-40, 1983.

Lorz et al., "Gene transfer to cereal cells mediated by protoplast transformation," *Mol. Gen. Genet.*, 199:178, 1985.

Maluszynaska et al., "Molecular cytogenetics of the genus *Arabidopsis*: In situ localization of rDNA sites, chromosome numbers and diversity in centrometric heterochromatin," *Annals Botany*, 71:479-484, 1993.

Maluszynska and Heslop-Harrison, Localization of tandemly repeated DNA sequences in *Arabidopsis thaliana*, *J. Plant*, 1(2):159-166, 1991.

Martinez-Zapater et al., "A highly repeated DNA sequence in *Arabidopsis thaliana*," *Mol. Gen. Genet.*, 204:417-423, 1986.

Mozo et al., "Construction and characterization of the IGF *Arabidopsis* BAC library," *Mol. Gen. Genet.*, 258:562-570, 1998.

Murphy and Karpen, "Localization of centromere function in a drosophila minichromosome," *Cell*, 82:599-609, 1995.

Murray et al., "Construction of artificial chromosomes in yeast," *Nature*, 305:189-193, 1983.

Napoli et al., "Introduction of a Chimeric Chalcone Synthase Gene into Petunia results in reversible co-suppression of homologous genes in trans," *The Plant Cell*, 2:279-289, 1990.

Perkins, "The detection of linkage in tetrad analysis," *Genetics*, 38, 187-197, 1953.

Potrykus et al., "Direct gene transfer to cells of a graminaceous monocot," *Mol. Gen. Genet.*, 199:183, 1985.

Preuss et al., "Tetrad analysis possible in *Arabidopsis* with mutation of the QUARTET (QRT) genes," *Science*, 264: 1458, 1994.

Rattner, "The structure of the mammalian centromere," *BioEssays*,13(2):51-55, 1991.

Richards et al., "The centromere region of *Arabidopsis thaliana* chromosome 1 contains telomere-similar sequences," *Nucleic Acids Research*, 19(12):3351-3357, 1991.

Rosenfeld, "Human artificial chromosomes get real," *Nature Genetics*, 15:333-335, 1997.

Round et al., "*Arabidopsis thaliana* centromere region: genetic map positions and repetitive DNA structure," *Gen. Res.*, 7:1045-1053, 1997.

Sasnauskas et al., "Molecular cloning and analysis of autonomous replicating sequence of *Candida maltosa*," *Yeast*, 8:253-259, 1992.

Schmidt et al., "Physical map and organization of *Arabidopsis thaliana* chromosome 4," *Science*, 270:480-483, 1995.

Singh et al., Centromere mapping and orientation of the molecular linkage map of rice (*Oryza sativa* L.), *Proc. Natl. Acad. Sci. USA*, 93:6163-6168, 1996.

Smythe, "Pollen clusters," *Current Biology*, 4:851-853, 1994.

Sun et al., "Human artificial episomal chromosomes for cloning large DNA fragments in human cells," *Nature Genetics*, 8:33-41, 1994.

Sun et al., "Molecular structure of a functional drosophila centromere," *Cell.* 91:1007-1019, 1997.

Tavoletti et al., "Half tetrad analysis of alfalfa using multiple restriction fragment length polymorphism markers," *Proc. Natl. Acad. Sci. USA*, 93:10918-10922, 1996.

Tyler-Smith et al., "Localization of DNA sequences required for human centromere function through an analysis of rearranged Y chromosomes," *Nature Genetics*, 5:370-375, 1993b.

Tyler-Smith et al., "Mammalian chromosome structure," *Current Biology*, 3:390-397, 1993a.

Valvekens et al., "Agrobacterium tumefaciens-mediated transformation of *Arabidopsis thaliana* root explants by using kanamycin selection," *Proc. Natl. Acad. Sci., USA* 85:5536-5540, 1988.

Wevrick et al., "Partial deletion of alpha satellite DNA association with reduced amounts of the centromere protein CENP-B in a mitotically stable human chromosome rearrangement," *Mol Cell Biol.*, 10:6374-6380, 1990.

Willard, "Centromeres of mammalian chromosomes" *Trends Genet.*, 6:410-416, 1990.

Willard, "Centromeres: the missing link in the development of human artificial chromosomes," *Genetics and Development*, 8:219-225, 1998a.

Willard, "Human artificial chromosomes coming into focus, " *Nature Biotech.*, 16:415-416, 1998b.

Williams et al., "Neurocentromere activity of structurally acentric mini-chromosomes in *Drosophila*," *Nature Genetics*, 18:30-37, 1998.

Xiang and Guerra, "The anti-nptll gene," *Plant Physiol.*, 102:287-293, 1993.

Zentgraf, "Telomere-binding proteins of *Arabidopsis thaliana*," *Plant Molecular Biology*, 27:467-475, 1995.

* cited by examiner

|   | A | B | C | D |
|---|---|---|---|---|
| 1 | T1-1 | PLA391 | tetrad seed stock | |
| 2 | T1-2 | PLA392 | tetrad seed stock | |
| 3 | T1-3 | PLA393 | tetrad seed stock | |
| 4 | T1-4 | PLA394 | tetrad seed stock | |
| 5 | | | | |
| 6 | T2-1 | PLA395 | tetrad seed stock | |
| 7 | T2-2 | PLA396 | tetrad seed stock | |
| 8 | T2-3 | PLA397 | tetrad seed stock | |
| 9 | T2-4 | PLA398 | tetrad seed stock | |
| 10 | | | | |
| 11 | T3-1 | PLA399 | tetrad seed stock | |
| 12 | T3-2 | PLA400 | tetrad seed stock | |
| 13 | T3-3 | PLA401 | tetrad seed stock | |
| 14 | T3-4 | PLA402 | tetrad seed stock | |
| 15 | | | | |
| 16 | T4-1 | PLA403 | tetrad seed stock | |
| 17 | T4-2 | PLA404 | tetrad seed stock | |
| 18 | T4-3 | PLA405 | tetrad seed stock | |
| 19 | T4-4 | PLA406 | tetrad seed stock | |
| 20 | | | | |
| 21 | T5-1 | PLA407 | tetrad seed stock | |
| 22 | T5-2 | PLA408 | tetrad seed stock | |
| 23 | T5-3 | PLA409 | tetrad seed stock | |
| 24 | T5-4 | PLA410 | tetrad seed stock | |
| 25 | | | | |
| 26 | T6-1 | PLA411 | tetrad seed stock | |
| 27 | T6-2 | PLA412 | tetrad seed stock | |
| 28 | T6-3 | PLA413 | tetrad seed stock | |
| 29 | T6-4 | PLA414 | tetrad seed stock | |
| 30 | | | | |
| 31 | T7-1 | PLA415 | tetrad seed stock | |
| 32 | T7-2 | PLA416 | tetrad seed stock | |
| 33 | T7-3 | PLA417 | tetrad seed stock | |
| 34 | T7-4 | PLA418 | tetrad seed stock | |
| 35 | | | | |

FIG. 4A

|    | A     | B      | C                 | D |
|----|-------|--------|-------------------|---|
| 36 | T8-1  | PLA419 | tetrad seed stock |   |
| 37 | T8-2  | PLA420 | tetrad seed stock |   |
| 38 | T8-3  | PLA421 | tetrad seed stock |   |
| 39 |       |        |                   |   |
| 40 | T10-1 | PLA422 | tetrad seed stock |   |
| 41 | T10-2 | PLA423 | tetrad seed stock |   |
| 42 | T10-3 | PLA424 | tetrad seed stock |   |
| 43 |       |        |                   |   |
| 44 | T11-1 | PLA425 | tetrad seed stock |   |
| 45 | T11-2 | PLA426 | tetrad seed stock |   |
| 46 | T11-3 | PLA427 | tetrad seed stock |   |
| 47 |       |        |                   |   |
| 48 | T12-1 | PLA428 | tetrad seed stock |   |
| 49 | T12-2 | PLA429 | tetrad seed stock |   |
| 50 | T12-3 | PLA430 | tetrad seed stock |   |
| 51 |       |        |                   |   |
| 52 | T13-1 | PLA431 | tetrad seed stock |   |
| 53 | T13-2 | PLA432 | tetrad seed stock |   |
| 54 | T13-3 | PLA433 | tetrad seed stock |   |
| 55 |       |        |                   |   |
| 56 | T14-1 | PLA434 | tetrad seed stock |   |
| 57 | T14-2 | PLA435 | tetrad seed stock |   |
| 58 | T14-3 | PLA436 | tetrad seed stock |   |
| 59 |       |        |                   |   |
| 60 | T18-1 | PLA437 | tetrad seed stock |   |
| 61 | T18-2 | PLA438 | tetrad seed stock |   |
| 62 | T18-3 | PLA439 | tetrad seed stock |   |
| 63 |       |        |                   |   |
| 64 | T20-1 | PLA440 | tetrad seed stock |   |
| 65 | T20-2 | PLA441 | tetrad seed stock |   |
| 66 | T20-3 | PLA442 | tetrad seed stock |   |
| 67 |       |        |                   |   |
| 68 | T27-1 | PLA443 | tetrad seed stock |   |
| 69 | T27-2 | PLA444 | tetrad seed stock |   |
| 70 | T27-3 | PLA445 | tetrad seed stock |   |

FIG. 4B

|     | A     | B      | C                  | D |
|-----|-------|--------|--------------------|---|
| 71  |       |        |                    |   |
| 72  | T28-1 | PLA446 | tetrad seed stock  |   |
| 73  | T28-2 | PLA447 | tetrad seed stock  |   |
| 74  | T28-3 | PLA448 | tetrad seed stock  |   |
| 75  |       |        |                    |   |
| 76  | T29-1 | PLA449 | tetrad seed stock  |   |
| 77  | T29-2 | PLA450 | tetrad seed stock  |   |
| 78  | T29-3 | PLA451 | tetrad seed stock  |   |
| 79  |       |        |                    |   |
| 80  | T30-1 | PLA452 | tetrad seed stock  |   |
| 81  | T30-2 | PLA453 | tetrad seed stock  |   |
| 82  | T30-3 | PLA454 | tetrad seed stock  |   |
| 83  | T30-4 | PLA455 | tetrad seed stock  |   |
| 84  |       |        |                    |   |
| 85  | T31-1 | PLA456 | tetrad seed stock  |   |
| 86  | T31-2 | PLA457 | tetrad seed stock  |   |
| 87  | T31-3 | PLA458 | tetrad seed stock  |   |
| 88  |       |        |                    |   |
| 89  | T32-1 | PLA459 | tetrad seed stock  |   |
| 90  | T32-2 | PLA460 | tetrad seed stock  |   |
| 91  | T32-3 | PLA461 | tetrad seed stock  |   |
| 92  | T32-4 | PLA462 | tetrad seed stock  |   |
| 93  |       |        |                    |   |
| 94  | T33-1 | PLA463 | tetrad seed stock  |   |
| 95  | T33-2 | PLA464 | tetrad seed stock  |   |
| 96  | T33-3 | PLA465 | tetrad seed stock  |   |
| 97  |       |        |                    |   |
| 98  | T34-1 | PLA466 | tetrad seed stock  |   |
| 99  | T34-2 | PLA467 | tetrad seed stock  |   |
| 100 | T34-3 | PLA468 | tetrad seed stock  |   |
| 101 | T34-4 | PLA469 | tetrad seed stock  |   |
| 102 |       |        |                    |   |
| 103 | T35-1 | PLA470 | tetrad seed stock  |   |
| 104 | T35-2 | PLA471 | tetrad seed stock  |   |
| 105 | T35-3 | PLA472 | tetrad seed stock  |   |

FIG. 4C

|     | A      | B       | C                  | D |
| --- | ------ | ------- | ------------------ | - |
| 106 | T35-4  | PLA473  | tetrad seed stock  |   |
| 107 |        |         |                    |   |
| 108 | T36-1  | PLA474  | tetrad seed stock  |   |
| 109 | T36-2  | PLA475  | tetrad seed stock  |   |
| 110 | T36-3  | PLA476  | tetrad seed stock  |   |
| 111 | T36-4  | PLA477  | tetrad seed stock  |   |
| 112 |        |         |                    |   |
| 113 | T37-1  | PLA478  | tetrad seed stock  |   |
| 114 | T37-2  | PLA479  | tetrad seed stock  |   |
| 115 | T37-3  | PLA480  | tetrad seed stock  |   |
| 116 | T37-4  | PLA481  | tetrad seed stock  |   |
| 117 |        |         |                    |   |
| 118 | T38-1  | PLA482  | tetrad seed stock  |   |
| 119 | T38-2  | PLA483  | tetrad seed stock  |   |
| 120 | T38-3  | PLA484  | tetrad seed stock  |   |
| 121 | T38-4  | PLA485  | tetrad seed stock  |   |
| 122 |        |         |                    |   |
| 123 | T39-1  | PLA486  | tetrad seed stock  |   |
| 124 | T39-2  | PLA487  | tetrad seed stock  |   |
| 125 | T39-3  | PLA488  | tetrad seed stock  |   |
| 126 |        |         |                    |   |
| 127 | T40-1  | PLA489  | tetrad seed stock  |   |
| 128 | T40-2  | PLA490  | tetrad seed stock  |   |
| 129 | T40-3  | PLA491  | tetrad seed stock  |   |
| 130 |        |         |                    |   |
| 131 | T41-1  | PLA492  | tetrad seed stock  |   |
| 132 | T41-2  | PLA493  | tetrad seed stock  |   |
| 133 | T41-3  | PLA494  | tetrad seed stock  |   |
| 134 | T41-4  | PLA495  | tetrad seed stock  |   |
| 135 |        |         |                    |   |
| 136 | T42-1  | PLA496  | tetrad seed stock  |   |
| 137 | T42-2  | PLA497  | tetrad seed stock  |   |
| 138 | T42-3  | PLA498  | tetrad seed stock  |   |
| 139 |        |         |                    |   |
| 140 | T43-1  | PLA499  | tetrad seed stock  |   |

FIG. 4D

|     | A      | B       | C                  | D |
|-----|--------|---------|--------------------|---|
| 141 | T43-2  | PLA500  | tetrad seed stock  |   |
| 142 | T43-3  | PLA501  | tetrad seed stock  |   |
| 143 |        |         |                    |   |
| 144 | T44-1  | PLA502  | tetrad seed stock  |   |
| 145 | T44-2  | PLA503  | tetrad seed stock  |   |
| 146 | T44-3  | PLA504  | tetrad seed stock  |   |
| 147 | T44-4  | PLA505  | tetrad seed stock  |   |
| 148 |        |         |                    |   |
| 149 | T45-1  | PLA506  | tetrad seed stock  |   |
| 150 | T45-2  | PLA507  | tetrad seed stock  |   |
| 151 | T45-3  | PLA508  | tetrad seed stock  |   |
| 152 | T45-4  | PLA509  | tetrad seed stock  |   |
| 153 |        |         |                    |   |
| 154 | T46-1  | PLA510  | tetrad seed stock  |   |
| 155 | T46-2  | PLA511  | tetrad seed stock  |   |
| 156 | T46-3  | PLA512  | tetrad seed stock  |   |
| 157 | T46-4  | PLA513  | tetrad seed stock  |   |
| 158 |        |         |                    |   |
| 159 | T48-1  | PLA514  | tetrad seed stock  |   |
| 160 | T48-2  | PLA515  | tetrad seed stock  |   |
| 161 | T48-3  | PLA516  | tetrad seed stock  |   |
| 162 |        |         |                    |   |
| 163 | T49-1  | PLA517  | tetrad seed stock  |   |
| 164 | T49-2  | PLA518  | tetrad seed stock  |   |
| 165 | T49-3  | PLA519  | tetrad seed stock  |   |
| 166 | T49-4  | PLA520  | tetrad seed stock  |   |
| 167 |        |         |                    |   |
| 168 | T52-1  | PLA521  | tetrad seed stock  |   |
| 169 | T52-2  | PLA522  | tetrad seed stock  |   |
| 170 | T52-3  | PLA523  | tetrad seed stock  |   |
| 171 |        |         |                    |   |
| 172 | T53-1  | PLA524  | tetrad seed stock  |   |
| 173 | T53-2  | PLA525  | tetrad seed stock  |   |
| 174 | T53-3  | PLA526  | tetrad seed stock  |   |
| 175 |        |         |                    |   |

FIG. 4E

|     | A      | B       | C                  | D |
|-----|--------|---------|--------------------|---|
| 176 | T55-1  | PLA527  | tetrad seed stock  |   |
| 177 | T55-2  | PLA528  | tetrad seed stock  |   |
| 178 | T55-3  | PLA529  | tetrad seed stock  |   |
| 179 |        |         |                    |   |
| 180 | T56-1  | PLA530  | tetrad seed stock  |   |
| 181 | T56-2  | PLA531  | tetrad seed stock  |   |
| 182 | T56-3  | PLA532  | tetrad seed stock  |   |
| 183 | T56-4  | PLA533  | tetrad seed stock  |   |
| 184 |        |         |                    |   |
| 185 | T57-1  | PLA534  | tetrad seed stock  |   |
| 186 | T57-2  | PLA535  | tetrad seed stock  |   |
| 187 | T57-3  | PLA536  | tetrad seed stock  |   |
| 188 | T57-4  | PLA537  | tetrad seed stock  |   |
| 189 |        |         |                    |   |
| 190 | T58-1  | PLA538  | tetrad seed stock  |   |
| 191 | T58-2  | PLA539  | tetrad seed stock  |   |
| 192 | T58-3  | PLA540  | tetrad seed stock  |   |
| 193 |        |         |                    |   |
| 194 | T60-1  | PLA541  | tetrad seed stock  |   |
| 195 | T60-2  | PLA542  | tetrad seed stock  |   |
| 196 | T60-3  | PLA543  | tetrad seed stock  |   |
| 197 | T60-4  | PLA544  | tetrad seed stock  |   |
| 198 |        |         |                    |   |
| 199 | T61-1  | PLA545  | tetrad seed stock  |   |
| 200 | T61-2  | PLA546  | tetrad seed stock  |   |
| 201 | T61-3  | PLA547  | tetrad seed stock  |   |
| 202 | T61-4  | PLA548  | tetrad seed stock  |   |
| 203 |        |         |                    |   |
| 204 | T62-1  | PLA549  | tetrad seed stock  |   |
| 205 | T62-2  | PLA550  | tetrad seed stock  |   |
| 206 | T62-3  | PLA551  | tetrad seed stock  |   |
| 207 |        |         |                    |   |
| 208 | T63-1  | PLA552  | tetrad seed stock  |   |
| 209 | T63-2  | PLA553  | tetrad seed stock  |   |
| 210 | T63-3  | PLA554  | tetrad seed stock  |   |

FIG. 4F

|     | A     | B      | C                 | D |
|-----|-------|--------|-------------------|---|
| 211 |       |        |                   |   |
| 212 | T64-1 | PLA555 | tetrad seed stock |   |
| 213 | T64-2 | PLA556 | tetrad seed stock |   |
| 214 | T64-3 | PLA557 | tetrad seed stock |   |
| 215 | T64-4 | PLA558 | tetrad seed stock |   |
| 216 |       |        |                   |   |
| 217 | T66-1 | PLA559 | tetrad seed stock |   |
| 218 | T66-2 | PLA560 | tetrad seed stock |   |
| 219 | T66-3 | PLA561 | tetrad seed stock |   |
| 220 |       |        |                   |   |
| 221 | T68-1 | PLA562 | tetrad seed stock |   |
| 222 | T68-2 | PLA563 | tetrad seed stock |   |
| 223 | T68-3 | PLA564 | tetrad seed stock |   |
| 224 |       |        |                   |   |
| 225 | T69-1 | PLA565 | tetrad seed stock |   |
| 226 | T69-2 | PLA566 | tetrad seed stock |   |
| 227 | T69-3 | PLA567 | tetrad seed stock |   |
| 228 |       |        |                   |   |
| 229 | T70-1 | PLA568 | tetrad seed stock |   |
| 230 | T70-2 | PLA569 | tetrad seed stock |   |
| 231 | T70-3 | PLA570 | tetrad seed stock |   |
| 232 |       |        |                   |   |
| 233 | T71-1 | PLA571 | tetrad seed stock |   |
| 234 | T71-2 | PLA572 | tetrad seed stock |   |
| 235 | T71-3 | PLA573 | tetrad seed stock |   |
| 236 |       |        |                   |   |
| 237 | T72-1 | PLA574 | tetrad seed stock |   |
| 238 | T72-2 | PLA575 | tetrad seed stock |   |
| 239 | T72-3 | PLA576 | tetrad seed stock |   |
| 240 | T72-4 | PLA577 | tetrad seed stock |   |
| 241 |       |        |                   |   |
| 242 | T73-1 | PLA578 | tetrad seed stock |   |
| 243 | T73-2 | PLA579 | tetrad seed stock |   |
| 244 | T73-3 | PLA580 | tetrad seed stock |   |
| 245 |       |        |                   |   |

FIG. 4G

|  | A | B | C | D |
|---|---|---|---|---|
| 246 | T74-1 | PLA581 | tetrad seed stock |  |
| 247 | T74-2 | PLA582 | tetrad seed stock |  |
| 248 | T74-3 | PLA583 | tetrad seed stock |  |
| 249 |  |  |  |  |
| 250 | T75-1 | PLA584 | tetrad seed stock |  |
| 251 | T75-2 | PLA585 | tetrad seed stock |  |
| 252 | T75-3 | PLA586 | tetrad seed stock |  |
| 253 |  |  |  |  |
| 254 | T78-1 | PLA587 | tetrad seed stock |  |
| 255 | T78-2 | PLA588 | tetrad seed stock |  |
| 256 | T78-3 | PLA589 | tetrad seed stock |  |
| 257 |  |  |  |  |
| 258 | T79-1 | PLA590 | tetrad seed stock |  |
| 259 | T79-2 | PLA591 | tetrad seed stock |  |
| 260 | T79-3 | PLA592 | tetrad seed stock |  |
| 261 | T79-4 | PLA593 | tetrad seed stock |  |
| 262 |  |  |  |  |
| 263 | T89-1 | PLA685 | tetrad seed stock |  |
| 264 | T89-2 | PLA686 | tetrad seed stock |  |
| 265 | T89-3 | PLA687 | tetrad seed stock |  |
| 266 |  |  |  |  |
| 267 | T90-1 | PLA688 | tetrad seed stock |  |
| 268 | T90-2 | PLA689 | tetrad seed stock |  |
| 269 | T90-3 | PLA690 | tetrad seed stock |  |
| 270 | T90-4 | PLA691 | tetrad seed stock |  |
| 271 |  |  |  |  |
| 272 | T95-1 | PLA698 | tetrad seed stock |  |
| 273 | T95-2 | PLA699 | tetrad seed stock |  |
| 274 | T95-3 | PLA700 | tetrad seed stock |  |
| 275 |  |  |  |  |
| 276 | T106-1 | PLA718 | tetrad seed stock |  |
| 277 | T106-2 | PLA719 | tetrad seed stock |  |
| 278 | T106-3 | PLA720 | tetrad seed stock |  |
| 279 |  |  |  |  |
| 280 | T108-1 | PLA950 | tetrad seed stock |  |

FIG. 4H

|     | A      | B      | C                 | D |
|-----|--------|--------|-------------------|---|
| 281 | T108-2 | PLA951 | tetrad seed stock |   |
| 282 | T108-3 | PLA952 | tetrad seed stock |   |
| 283 |        |        |                   |   |
| 284 | T126-1 | PLA761 | tetrad seed stock |   |
| 285 | T126-2 | PLA762 | tetrad seed stock |   |
| 286 | T126-3 | PLA763 | tetrad seed stock |   |
| 287 |        |        |                   |   |
| 288 | T129-1 | PLA771 | tetrad seed stock |   |
| 289 | T129-2 | PLA772 | tetrad seed stock |   |
| 290 | T129-3 | PLA773 | tetrad seed stock |   |
| 291 |        |        |                   |   |
| 292 | T130-1 | PLA774 | tetrad seed stock |   |
| 293 | T130-2 | PLA775 | tetrad seed stock |   |
| 294 | T130-3 | PLA776 | tetrad seed stock |   |
| 295 | T130-4 | PLA777 | tetrad seed stock |   |
| 296 |        |        |                   |   |
| 297 | T131-1 | PLA778 | tetrad seed stock |   |
| 298 | T131-2 | PLA779 | tetrad seed stock |   |
| 299 | T131-3 | PLA780 | tetrad seed stock |   |
| 300 |        |        |                   |   |
| 301 | T132-1 | PLA781 | tetrad seed stock |   |
| 302 | T132-2 | PLA782 | tetrad seed stock |   |
| 303 | T132-3 | PLA783 | tetrad seed stock |   |
| 304 |        |        |                   |   |
| 305 | T138-1 | PLA806 | tetrad seed stock |   |
| 306 | T138-2 | PLA807 | tetrad seed stock |   |
| 307 | T138-3 | PLA808 | tetrad seed stock |   |
| 308 | T138-4 | PLA809 | tetrad seed stock |   |
| 309 |        |        |                   |   |
| 310 | T144-1 | PLA820 | tetrad seed stock |   |
| 311 | T144-2 | PLA821 | tetrad seed stock |   |
| 312 | T144-3 | PLA822 | tetrad seed stock |   |
| 313 |        |        |                   |   |
| 314 | T146-1 | PLA826 | tetrad seed stock |   |
| 315 | T146-2 | PLA827 | tetrad seed stock |   |

FIG. 41

|     | A      | B      | C                 | D |
|-----|--------|--------|-------------------|---|
| 316 | T146-3 | PLA828 | tetrad seed stock |   |
| 317 | T146-4 | PLA829 | tetrad seed stock |   |
| 318 |        |        |                   |   |
| 319 | T148-1 | PLA830 | tetrad seed stock |   |
| 320 | T148-2 | PLA831 | tetrad seed stock |   |
| 321 | T148-3 | PLA832 | tetrad seed stock |   |
| 322 |        |        |                   |   |
| 323 | T162-1 | PLA859 | tetrad seed stock |   |
| 324 | T162-2 | PLA860 | tetrad seed stock |   |
| 325 | T162-3 | PLA861 | tetrad seed stock |   |
| 326 |        |        |                   |   |
| 327 | T171-1 | PLA883 | tetrad seed stock |   |
| 328 | T171-2 | PLA884 | tetrad seed stock |   |
| 329 | T171-3 | PLA885 | tetrad seed stock |   |
| 330 |        |        |                   |   |
| 331 | T175-1 | PLA895 | tetrad seed stock |   |
| 332 | T175-2 | PLA896 | tetrad seed stock |   |
| 333 | T175-3 | PLA897 | tetrad seed stock |   |
| 334 |        |        |                   |   |
| 335 | T178-1 | PLA901 | tetrad seed stock |   |
| 336 | T178-2 | PLA902 | tetrad seed stock |   |
| 337 | T178-3 | PLA903 | tetrad seed stock |   |
| 338 |        |        |                   |   |
| 339 | T180-1 | PLA908 | tetrad seed stock |   |
| 340 | T180-2 | PLA909 | tetrad seed stock |   |
| 341 | T180-3 | PLA910 | tetrad seed stock |   |
| 342 |        |        |                   |   |
| 343 | T185-1 | PLA923 | tetrad seed stock |   |
| 344 | T185-2 | PLA924 | tetrad seed stock |   |
| 345 | T185-3 | PLA925 | tetrad seed stock |   |
| 346 |        |        |                   |   |
| 347 | T189-1 | PLA935 | tetrad seed stock |   |
| 348 | T189-2 | PLA936 | tetrad seed stock |   |
| 349 | T189-3 | PLA937 | tetrad seed stock |   |
| 350 |        |        |                   |   |

FIG. 4J

| | A | B | C | D |
|---|---|---|---|---|
| 351 | T222-1 | PLA1152 | tetrad seed stock | |
| 352 | T222-2 | PLA1153 | tetrad seed stock | |
| 353 | T222-3 | PLA1154 | tetrad seed stock | |
| 354 | T222-4 | PLA1155 | tetrad seed stock | |
| 355 | | | | |
| 356 | T227-1 | PLA1156 | tetrad seed stock | |
| 357 | T227-2 | PLA1157 | tetrad seed stock | |
| 358 | T227-3 | PLA1158 | tetrad seed stock | |
| 359 | T227-4 | PLA1159 | tetrad seed stock | |
| 360 | | | | |
| 361 | T233-1 | PLA1160 | tetrad seed stock | |
| 362 | T233-2 | PLA1161 | tetrad seed stock | |
| 363 | T233-3 | PLA1162 | tetrad seed stock | seed not available yet |
| 364 | | | | |
| 365 | T236-1 | PLA1163 | tetrad seed stock | seed not available yet |
| 366 | T236-2 | PLA1164 | tetrad seed stock | |
| 367 | T236-3 | PLA1165 | tetrad seed stock | seed not available yet |
| 368 | | | | |
| 369 | T261-1 | PLA1166 | tetrad seed stock | seed not available yet |
| 370 | T261-2 | PLA1167 | tetrad seed stock | seed not available yet |
| 371 | T261-3 | PLA1168 | tetrad seed stock | seed not available yet |
| 372 | | | | |
| 373 | T275-1 | PLA1169 | tetrad seed stock | seed not available yet |
| 374 | T275-2 | PLA1170 | tetrad seed stock | seed not available yet |
| 375 | T275-3 | PLA1171 | tetrad seed stock | |
| 376 | | | | |
| 377 | T276-1 | PLA1172 | tetrad seed stock | |

FIG. 4K

|     | A      | B       | C                 | D                  |
|-----|--------|---------|-------------------|--------------------|
| 378 | T276-2 | PLA1173 | tetrad seed stock | seed not available yet |
| 379 | T276-3 | PLA1174 | tetrad seed stock |                    |
| 380 | T276-4 | PLA1175 | tetrad seed stock |                    |
| 381 |        |         |                   |                    |
| 382 | T279-1 | PLA1176 | tetrad seed stock |                    |
| 383 | T279-2 | PLA1177 | tetrad seed stock | seed not available yet |
| 384 | T279-3 | PLA1178 | tetrad seed stock | seed not available yet |
| 385 |        |         |                   |                    |
| 386 | T281-1 | PLA1179 | tetrad seed stock | seed not available yet |
| 387 | T281-2 | PLA1180 | tetrad seed stock | seed not available yet |
| 388 | T281-3 | PLA1181 | tetrad seed stock |                    |
| 389 | T281-4 | PLA1182 | tetrad seed stock | seed not available yet |
| 390 |        |         |                   |                    |
| 391 | T289-1 | PLA1183 | tetrad seed stock | seed not available yet |
| 392 | T289-2 | PLA1184 | tetrad seed stock | seed not available yet |
| 393 | T289-3 | PLA1185 | tetrad seed stock |                    |
| 394 |        |         |                   |                    |
| 395 | T291-1 | PLA1186 | tetrad seed stock |                    |
| 396 | T291-2 | PLA1187 | tetrad seed stock | seed not available yet |
| 397 | T291-3 | PLA1188 | tetrad seed stock |                    |
| 398 |        |         |                   |                    |
| 399 | T303-1 | PLA1189 | tetrad seed stock |                    |
| 400 | T303-2 | PLA1190 | tetrad seed stock |                    |
| 401 | T303-3 | PLA1191 | tetrad seed stock |                    |
| 402 |        |         |                   |                    |
| 403 | T308-1 | PLA1192 | tetrad seed stock |                    |

FIG. 4L

|   | A | B | C | D |
|---|---|---|---|---|
| 404 | T308-2 | PLA1193 | tetrad seed stock | seed not available yet |
| 405 | T308-3 | PLA1194 | tetrad seed stock | seed not available yet |
| 406 |  |  |  |  |
| 407 | T311-1 | PLA1195 | tetrad seed stock | seed not available yet |
| 408 | T311-2 | PLA1196 | tetrad seed stock |  |
| 409 | T311-3 | PLA1197 | tetrad seed stock |  |
| 410 |  |  |  |  |
| 411 | T312-1 | PLA1198 | tetrad seed stock |  |
| 412 | T312-2 | PLA1199 | tetrad seed stock |  |
| 413 | T312-3 | PLA1200 | tetrad seed stock | seed not available yet |
| 414 |  |  |  |  |
| 415 | T324-1 | PLA1201 | tetrad seed stock |  |
| 416 | T324-2 | PLA1202 | tetrad seed stock |  |
| 417 | T324-3 | PLA1203 | tetrad seed stock |  |
| 418 | T324-4 | PLA1204 | tetrad seed stock |  |
| 420 | T330-1 | PLA1205 | tetrad seed stock | seed not available yet |
| 421 | T330-2 | PLA1206 | tetrad seed stock |  |
| 422 | T330-3 | PLA1207 | tetrad seed stock |  |
| 423 |  |  |  |  |
| 424 | T343-1 | PLA1208 | tetrad seed stock |  |
| 425 | T343-2 | PLA1209 | tetrad seed stock |  |
| 426 | T343-3 | PLA1210 | tetrad seed stock | seed not available yet |
| 427 |  |  |  |  |
| 428 | T354-1 | PLA1211 | tetrad seed stock |  |
| 429 | T354-2 | PLA1212 | tetrad seed stock | seed not available yet |
| 430 | T354-3 | PLA1213 | tetrad seed stock | seed not available yet |
| 431 |  |  |  |  |

FIG. 4M

|   | A | B | C | D |
|---|---|---|---|---|
| 432 | T363-1 | PLA1214 | tetrad seed stock | seed not available yet |
| 433 | T363-2 | PLA1215 | tetrad seed stock | seed not available yet |
| 434 | T363-3 | PLA1216 | tetrad seed stock | seed not available yet |
| 435 |   |   |   |   |
| 436 | T373-1 | PLA1217 | tetrad seed stock |   |
| 437 | T373-2 | PLA1218 | tetrad seed stock | seed not available yet |
| 438 | T373-3 | PLA1219 | tetrad seed stock | seed not available yet |
| 439 |   |   |   |   |
| 440 | T378-1 | PLA1220 | tetrad seed stock | seed not available yet |
| 441 | T378-2 | PLA1221 | tetrad seed stock | seed not available yet |
| 442 | T378-3 | PLA1222 | tetrad seed stock | seed not available yet |
| 443 |   |   |   |   |
| 444 | T388-1 | PLA1223 | tetrad seed stock | seed not available yet |
| 445 | T388-2 | PLA1224 | tetrad seed stock | seed not available yet |
| 446 | T388-3 | PLA1225 | tetrad seed stock | seed not available yet |
| 447 | T388-4 | PLA1226 | tetrad seed stock | seed not available yet |
| 448 |   |   |   |   |
| 449 | T390-1 | PLA1227 | tetrad seed stock | seed not available yet |
| 450 | T390-2 | PLA1228 | tetrad seed stock | seed not available yet |
| 451 | T390-3 | PLA1229 | tetrad seed stock | seed not available yet |

FIG. 4N

|     | A      | B       | C                 | D                   |
|-----|--------|---------|-------------------|---------------------|
| 452 |        |         |                   |                     |
| 453 | T395-1 | PLA1230 | tetrad seed stock | seed not available yet |
| 454 | T395-2 | PLA1231 | tetrad seed stock | seed not available yet |
| 455 | T395-3 | PLA1232 | tetrad seed stock | seed not available yet |
| 456 | T395-4 | PLA1233 | tetrad seed stock | seed not available yet |
| 457 |        |         |                   |                     |
| 458 | T396-1 | PLA1234 | tetrad seed stock | seed not available yet |
| 459 | T396-2 | PLA1235 | tetrad seed stock | seed not available yet |
| 460 | T396-3 | PLA1236 | tetrad seed stock | seed not available yet |
| 461 |        |         |                   |                     |
| 462 | T400-1 | PLA1237 | tetrad seed stock | seed not available yet |
| 463 | T400-2 | PLA1238 | tetrad seed stock | seed not available yet |
| 464 | T400-3 | PLA1239 | tetrad seed stock | seed not available yet |
| 465 |        |         |                   |                     |
| 466 | T410-1 | PLA1240 | tetrad seed stock | seed not available yet |
| 467 | T410-2 | PLA1241 | tetrad seed stock | seed not available yet |
| 468 | T410-3 | PLA1242 | tetrad seed stock | seed not available yet |
| 469 |        |         |                   |                     |
| 470 | T436-1 | PLA1243 | tetrad seed stock | seed not available yet |
| 471 | T436-2 | PLA1244 | tetrad seed stock | seed not available yet |

FIG. 40

|     | A      | B       | C                 | D                        |
|-----|--------|---------|-------------------|--------------------------|
| 472 | T436-3 | PLA1245 | tetrad seed stock | seed not available yet   |
| 473 |        |         |                   |                          |
| 474 | T440-1 | PLA1246 | tetrad seed stock | seed not available yet   |
| 475 | T440-2 | PLA1247 | tetrad seed stock | seed not available yet   |
| 476 | T440-3 | PLA1248 | tetrad seed stock | seed not available yet   |
| 477 |        |         |                   |                          |
| 478 | T442-1 | PLA1249 | tetrad seed stock | seed not available yet   |
| 479 | T442-2 | PLA1250 | tetrad seed stock | seed not available yet   |
| 480 | T442-3 | PLA1251 | tetrad seed stock | seed not available yet   |
| 481 | T442-4 | PLA1252 | tetrad seed stock | seed not available yet   |
| 482 |        |         |                   |                          |
| 483 | T443-1 | PLA1253 | tetrad seed stock | seed not available yet   |
| 484 | T443-2 | PLA1254 | tetrad seed stock | seed not available yet   |
| 485 | T443-3 | PLA1255 | tetrad seed stock | seed not available yet   |
| 486 |        |         |                   |                          |
| 487 | T451-1 | PLA1256 | tetrad seed stock | seed not available yet   |
| 488 | T451-2 | PLA1257 | tetrad seed stock | seed not available yet   |
| 489 | T451-3 | PLA1258 | tetrad seed stock | seed not available yet   |
| 490 | T451-4 | PLA1259 | tetrad seed stock | seed not available yet   |
| 491 |        |         |                   |                          |

FIG. 4P

|  | A | B | C | D |
|---|---|---|---|---|
| 492 | T456-1 | PLA1260 | tetrad seed stock | seed not available yet |
| 493 | T456-2 | PLA1261 | tetrad seed stock | seed not available yet |
| 494 | T456-3 | PLA1262 | tetrad seed stock | seed not available yet |
| 495 |  |  |  |  |
| 496 | T465-1 | PLA1263 | tetrad seed stock | seed not available yet |
| 497 | T465-2 | PLA1264 | tetrad seed stock | seed not available yet |
| 498 | T465-3 | PLA1265 | tetrad seed stock | seed not available yet |
| 499 | T465-4 | PLA1266 | tetrad seed stock | seed not available yet |
| 500 |  |  |  |  |
| 501 | T467-1 | PLA1267 | tetrad seed stock | seed not available yet |
| 502 | T467-2 | PLA1268 | tetrad seed stock | seed not available yet |
| 503 | T467-3 | PLA1269 | tetrad seed stock | seed not available yet |
| 504 |  |  |  |  |
| 505 | T470-1 | PLA1270 | tetrad seed stock | seed not available yet |
| 506 | T470-2 | PLA1271 | tetrad seed stock | seed not available yet |
| 507 | T470-3 | PLA1272 | tetrad seed stock | seed not available yet |
| 508 | T470-4 | PLA1273 | tetrad seed stock | seed not available yet |

FIG. 4Q

| Chromo-some# | Marker Name | Marker Type | Public? |
|---|---|---|---|
| 1 | nga59 | SSLP | YES |
| 1 | nga63 | SSLP | YES |
| 1 | m59 | CAPS (BstU I) | YES |
| 1 | g2395 | CAPS (Xba I) | YES |
| 1 | m235 | CAPS (Hind III) | YES |
| 1 | athZFPG | SSLP | YES |
| 1 | S0392 | SSLP | YES |
| 1 | UFO | CAPS (Taq I) | YES |
| 1 | Cxc750 | SSLP | NO |
| 1 | 7G6 | CAPS (Acc I) | NO |
| 1 | AIG1 | CAPS (MnI I) | NO |
| 1 | mi63 | CAPS (NIa III) | NO |
| 1 | mi342 | CAPS (Hinf I) | NO |
| 1 | T22C23 | CAPS (MnI I) | NO |
| 1 | T5D18 | CAPS (Aci I) | NO |
| 1 | T3L4 | CAPS (Mae III) | NO |
| 1 | T27K12 | SSLP | YES |
| 1 | jcc3 | CAPS (NIa III) | NO |
| 1 | GPCmi19 | CAPS (Fnu4h I) | NO |
| 1 | nga280 | SSLP | YES |
| 1 | nga128 | SSLP | YES |
| 1 | ETR | CAPS (Nco I) | YES |

FIG. 5A-1

| Forward Primer | Reverse Primer |
|---|---|
| CGCCAAAGACTACGAAATGATC | ATAATAGATAAAGAGCCCCACAC |
| GGGTCTGGTTATGCCGTGAAG | GTTTTACTTAGTCCAATGGTAG |
| AAATGGCCAACGATCAGAGAATAG | GAAGTCCGGCATGTTATCACCAAG |
| CAAGTCGCAAACGGGAAAATG | AAACTACGCCTAACCACTATTCTC |
| GAAGTACAGCGGCTCAAAAGAAG | TTGCTGCCATGTAATACCTAAGTG |
| GTTGACTTGTATTTGATTTCTTTTTC | CGAGTGATTTCCTTTTGCTACC |
| AAGATAAAGCAGCGAATGTGTC | CGAAAGCCGTAACTAGATAATAAG |
| ATTCATGAGTGCAAAGGGTAGAG | CTCAGCCAAAGAATCAAGTAGAG |
| GGCTACTGGTCAAATCATTC | GAATCTTTGCAAACGAGTGG |
| GCGGCTGATGATCTCCACCTC | TTACCCCGCAGGAAAAAGTATG |

FIG. 5A-2

| Chromo-some# | Marker Name | Marker Type | Public? |
|---|---|---|---|
| 1 | TAG1 | SSLP | YES |
| 1 | AthATPASE | SSLP | YES |
| 1 | nga692 | SSLP | YES |
| 2 | nga1145 | SSLP | YES |
| 2 | m246 | CAPS (Mae III) | YES |
| 2 | mi310 | SSLP | NO |
| 2 | mi421 | CAPS (Hae III) | NO |
| 2 | GPC6 | SSLP | NO |
| 2 | mi398 | CAPS (MnI i) | NO |
| 2 | THY-1 | CAPS (Rsa I) | NO |
| 2 | PhyB | CAPS (Xho I) | YES |
| 2 | nga1126 | SSLP | YES |
| 2 | nga361 | SSLP | YES |
| 2 | nga168 | SSLP | YES |
| 3 | nga32 | SSLP | YES |
| 3 | nga172 | SSLP | YES |
| 3 | nga162 | SSLP | YES |
| 3 | ARLim | CAPS (EcoR I) | YES |
| 3 | GAPA | SSLP | YES |
| 3 | GL1 | CAPS (Taq I) | YES |

FIG. 5B-1

| Forward Primer | Reverse Primer |
|---|---|
| ACTTCATCACTTGCGGGACTG | GGCCCAAGAAGCCCACAACAC |
| TAACGTTCCCACATGAGC | AACTCTGTACCTGCTGGA |
| AGTCGATGTCTAGGCTCTTC | CTTCCATTTCTTGATTTAGTTC |
| ACTAAGGCCTGTGTTGATGTTTCTC | AACCGCTTCCCATTCGTCTTC |
| GGCGACCTTGGACCTGTATACG | AACCGCCATTTTCATTTCTATC |

FIG. 5B-2

| Chromo-some# | Marker Name | Marker Type | Public? |
|---|---|---|---|
| 3 | atbox | CAPS (Msp I) | NO |
| 3 | 91F1T7 | CAPS (Gun4H I) | NO |
| 3 | NIT | SSLP | YES |
| 3 | AFC1 | CAPS (Pvu II) | YES |
| 3 | TSA | CAPS (Alu I) | YES |
| 3 | nga112 | SSLP | YES |
| 3 | GA1 | CAPS (BsaB I) | YES |
| 4 | mi233 | SSLP | NO |
| 4 | T27D20 C4 | CAPS (Dde I) | NO |
| 4 | mi306 | CAPS (Tai I) | NO |
| 4 | mi87 | SSLP | NO |
| 4 | nga12 | SSLP | YES |
| 4 | F13H14 | SSLP | NO |
| 4 | mi167 | SSLP | NO |
| 4 | T25J3 | SSLP | NO |
| 4 | T3F12.0 | CAPS (Bgl II) | NO |
| 4 | HY4 | CAPS (Rsa I) | YES |
| 4 | nga8 | SSLP | YES |
| 4 | nga1111 | SSLP | YES |
| 4 | DET1 | SSLP | YES |
| 4 | COP9 | CAPS (Apo I) | NO |
| 4 | SC5 | CAPS (Acc I) | YES |

FIG. 5C-1

| Forward Primer | Reverse Primer |
|---|---|
| TCTGCTGCGGTGGGAATACAAAAG | GCCATCATTCCCCGGTTCTCATAAG |
| CCCCTCCCGCCCTAAACCTAC | TTCCGCTACATGGCCTTTCTACCTTG |
| | |
| | |
| | |
| CGTATTCCCCTGAAAAGTGACCTG | ACATCCGGCCTTCCCATTG |
| AAACGCCGCCAAATCAGAAC | ACAACCTTAGCCCCATCCATTC |
| CTGCGAGCGAGGTCAATG | GCAGCCGTGTGGATGGAG |
| TTTGCACCGCCTATGTTACC | GAGGACGTTTTGCAGAGTG |
| GCGAATTCCTTGCCACTAAG | AAGAAGAAGAGGAGGAAGAAGATGTC |
| AGTGGACGCCTTTCTTCAATGTG | TGGTCCGTCGTAGGCAAC |
| CTTCACGCTGCCTTCACTCTC | GATACGCTCGTCTTCCCACTCG |
| CAAAACCAAATCCGGGAAGAAC | AGTGGCCAGCCTTCTTAACATACC |
| CCGGGGAAGAAAGCCGTGAATC | CCCGGAGTTACAGCCCTTATGATG |
| | |
| | |
| TTGGGGATTGGTCAGAAG | ATATGTTGCAACTTAGAAATCAG |

FIG. 5C-2

| Chromo-some # | Marker Name | Marker Type | Public? |
|---|---|---|---|
| 4 | g4539 | CAPS (Hind III) | YES |
| 4 | AG | CAPS (Xba I) | YES |
| 4 | nga1139 | SSLP | YES |
| 4 | nga1107 | SSLP | YES |
| 5 | CTR1 | SSLP | YES |
| 5 | ca72 | SSLP | YES |
| 5 | nga106 | SSLP | YES |
| 5 | nga139 | SSLP | YES |
| 5 | SO262 | SSLP | YES |
| 5 | nga76 | SSLP | YES |
| 5 | CUE1 | CAPS (Mse I) | NO |
| 5 | PhyC | SSLP | YES |
| 5 | SO191 | SSLP | YES |
| 5 | DFR | CAPS (BsaA I) | YES |
| 5 | LFY | CAPS (Rsa I) | YES |

CAPS = Codominant cut amplified polymorphic sequence
SSLP = Simple sequence length polymorphism
grey boxes = markers between which centromere has been mapped

FIG. 5D-1

| Forward Primer | | | | | | | | | | | | | | | Reverse Primer | | | | | | | | | | | | | |
|---|---|---|---|---|---|---|---|---|---|---|---|---|---|---|---|---|---|---|---|---|---|---|---|---|---|---|---|---|
| | | | | | | | | TCTCGTTCTGATGGCTCCTGTG | | | | | | | GTGTAACCGGTGATACTCTCGCC | | | | | | | | | | | | | |

FIG. 5D-2

SEQUENCE LISTING

<160> NUMBER OF SEQ ID NOS: 44

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
cgccaaagac tacgaaatga tc                                           22

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
ataatagata aagagcccca cac                                          23

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
gggtctggtt atgccgtgaa g                                            21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
gttttactta gtccaatggt ag                                           22

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
aaatggccaa cgatcagaag aata                                         24

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gaagtccggc atgttatcac ccaag                                        25

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
caagtcgcaa acggaaaatg                                             20

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
aaactacgcc taaccactat tctc                                        24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
gaagtacagc ggctcaaaaa gaag                                        24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
ttgctgccat gtaataccta agtg                                        24

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
ggctactggt caaatcaaat cattc                                       25

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
gaatctttgc aaacgagtgg                                             20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
gcggctggat gatctccacc tc                                          22

```
<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
ttaccccgca ggaaaaagta tg                                              22

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
acttcatcac ttgcgggact g                                               21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
ggcccaagaa gcccacaaca c                                               21

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
gaggatgtcc aaggcgtctg tgc                                             23

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
ggggatttcg gttgtctgtc                                                 20

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
taacgttccc acatgagc                                                   18
```

```
<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
aactctgtac ctgctgga                                                     18

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
agtcgatgtc taggctcttc                                                   20

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
cttccatttc ttgatttagt tc                                                22

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
actaaggcct gtgttgatgt ttctc                                             25

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
aaccgcttcc cattcgtctt c                                                 21

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
ggcgaccttg gacctgtata cg                                                22
```

```
<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
aaccgccatt ttcatttcta tc                                              22

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
tctgcggtgg gaatacaaaa g                                               21

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
gccatcattc cccggttctc ataag                                           25

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
cccctcccgc cctaaaccta c                                               21

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
ttccgctaca tggccttcta ccttg                                           25

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
cgtattcccc tgaaaagtga cctg                                            24

<210> SEQ ID NO 32
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
acatccggcc ttcccattg                                                   19

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
tttgcaccgc ctatgttacc                                                  20

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
gaggacgttt tgcagagtg                                                   19

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
agtggacgcc ttcttcaatg tg                                               22

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
tggtccgtcg tagggcaac                                                   19

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
caaaaccaaa tccgcgaaga ac                                               22

<210> SEQ ID NO 38
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
agtggccagc cttcttaaca tacc                                           24

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
ccggggaaga aagcgtgaat c                                              21

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
cccggagtta cagcccttat gatg                                           24

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
ttgggggatt ggtcagaag                                                 19

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
atatgttgca acttagaatc ag                                             22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
tctcgttctg atggctcctg tg                                             22

<210> SEQ ID NO 44
<211> LENGTH: 25
<212> TYPE: DNA
```

```
<213> ORGANISM: Artificial Sequence
<220> FEATURE:
<223> OTHER INFORMATION: Description of Artificial Sequence:  Synthetic
      Primer

<400> SEQUENCE: 44
gtgtaaccgg tgatactctc tcgcc                                           25
```

PLANT ARTIFICIAL CHROMOSOME COMPOSITIONS AND METHODS

This application is a continuation of U.S. application Ser. No. 09/553,231, filed Apr. 19, 2000, now issued as U.S. Pat. No. 6,900,012 which application is a continuation application of Ser. No. 09/090,051, filed Jun. 3, 1998, now issued as U.S. Pat. No. 6,156,953; which application claims the priority of U.S. Provisional Patent Application Ser. No. 60/048,451, filed Jun. 3, 1997; and U.S. Provisional Patent Application Ser. No. 60/073,741, filed Feb. 5, 1998. The foregoing disclosures are each specifically incorporated herein by reference in their entirety.

The government owns rights in the present invention pursuant to U.S. Department of Agriculture Grant No. 96-35304-3491 and Grant No. DE-FC05-920R22072 from the Consortium for Plant Biotechnology.

BACKGROUND OF THE INVENTION

I. Field of the Invention

The present invention relates generally to the field of molecular biology. More particularly, it concerns the construction and use of plant artificial chromosomes.

II. Description of Related Art

Two general approaches are used for introduction of new genetic information ("transformation") into cells. One approach is to introduce the new genetic information as part of another DNA molecule, referred to as a "vector," which can be maintained as an independent unit (an episome) apart from the chromosomal DNA molecule(s). Episomal vectors contain all the necessary DNA sequence elements required for DNA replication and maintenance of the vector within the cell. Many episomal vectors are available for use in bacterial cells (for example, see Maniatis et al., 1982). However, only a few episomal vectors that function in higher eukaryotic cells have been developed. The available higher eukaryotic episomal vectors are based on naturally occurring viruses and most function only in mammalian cells (Willard, 1997). In higher plant systems the only known double-stranded DNA viruses that replicate through a double-stranded intermediate upon which an episomal vector could be based is the gemini virus, although the gemini virus is limited to an approximately 800 bp insert. Although an episomal plant vector based on the Cauliflower Mosaic Virus has been developed, its capacity to carry new genetic information also is limited (Brisson et al., 1984).

The other general method of genetic transformation involves integration of introduced DNA sequences into the recipient cell's chromosomes, permitting the new information to be replicated and partitioned to the cell's progeny as a part of the natural chromosomes. The most common form of integrative transformation is called "transfection" and is frequently used in mammalian cell culture systems. Transfection involves introduction of relatively large quantities of deproteinized DNA into cells. The introduced DNA usually is broken and joined together in various combinations before it is integrated at random sites into the cell's chromosome (see, for example Wigler et al., 1977). Common problems with this procedure are the rearrangement of introduced DNA sequences and unpredictable levels of expression due to the location of the transgene in the genome or so called "position effect variation" (Shingo et al., 1986). Further, unlike episomal DNA, integrated DNA cannot normally be precisely removed. A more refined form of integrative transformation can be achieved by exploiting naturally occurring viruses that integrate into the host's chromosomes as part of their life cycle, such as retroviruses (see Cepko et al., 1984). In mouse, homologous integration has recently become common, although it is significantly more difficult to use in plants (Lam et al. 1996).

The most common genetic transformation method used in higher plants is based on the transfer of bacterial DNA into plant chromosomes that occurs during infection by the phytopathogenic soil bacterium *Agrobacterium* (see Nester et al., 1984). By substituting genes of interest for the naturally transferred bacterial sequences (called T-DNA), investigators have been able to introduce new DNA into plant cells. However, even this more "refined" integrative transformation system is limited in three major ways. First, DNA sequences introduced into plant cells using the *Agrobacterium* T-DNA system are frequently rearranged (see Jones et al., 1987). Second, the expression of the introduced DNA sequences varies between individual transformants (see Jones et al., 1985). This variability is presumably caused by rearranged sequences and the influence of surrounding sequences in the plant chromosome (i.e., position effects), as well as methylation of the transgene. A third drawback of the *Agrobacterium* T-DNA system is the reliance on a "gene addition" mechanism: the new genetic information is added to the genome (i.e., all the genetic information a cell possesses) but does not replace information already present in the genome.

One attractive alternative to commonly used methods of transformation is the use of an artificial chromosome. Artificial chromosomes are man-made linear or circular DNA molecules constructed from essential cis-acting DNA sequence elements that are responsible for the proper replication and partitioning of natural chromosomes (see Murray et al., 1983). The essential elements are: (1) Autonomous Replication Sequences (ARS) (these have properties of replication origins, which are the sites for initiation of DNA replication), (2) Centromeres (site of kinetochore assembly and responsible for proper distribution of replicated chromosomes at mitosis or meiosis), and (3) Telomeres (specialized structures at the ends of linear chromosomes that function to stabilize the ends and facilitate the complete replication of the extreme termini of the DNA molecule).

At present, the essential chromosomal elements for construction of artificial chromosomes have been precisely characterized only from lower eukaryotic species. ARSs have been isolated from unicellular fungi, including *Saccharomyces cerevisiae* (brewer's yeast) and *Schizosaccharomyces pombe* (see Stinchcomb et al., 1979 and Hsiao et al., 1979). ARSs behave like replication origins allowing DNA molecules that contain the ARS to be replicated as an episome after introduction into the cell nuclei of these fungi. Plasmids containing these sequences replicate, but in the absence of a centromere they are partitioned randomly into daughter cells.

Artificial chromosomes have been constructed in yeast using the three cloned essential chromosomal elements. Murray et al., 1983, disclose a cloning system based on the in vitro construction of linear DNA molecules that can be transformed into yeast, where they are maintained as artificial chromosomes. These yeast artificial chromosomes (YACS) contain cloned genes, origins of replication, centromeres and telomeres and are segregated in daughter cells with high affinity when the YAC is at least 100 kB in length. Smaller CEN containing vectors may be stably segregated, however, when in circular form.

None of the essential components identified in unicellular organisms, however, function in higher eukaryotic systems.

For example, a yeast CEN sequence will not confer stable inheritance upon vectors transformed into higher eukaryotes. While such DNA fragments can be readily be introduced, they do not stably exist as episomes in the host cell. This has seriously hampered efforts to produce artificial chromosomes in higher organisms.

In one case, a plant artificial chromosome was discussed (Richards et al., U.S. Pat. No. 5,270,201). However, this vector was based on plant telomeres, as a functional plant centromere was not disclosed. While telomeres are important in maintaining the stability of chromosomal termini, they do not encode the information needed to ensure stable inheritance of an artificial chromosome. It is well documented that centromere function is crucial for stable chromosomal inheritance in almost all eukaryotic organisms (reviewed in Nicklas 1988). For example, broken chromosomes that lack a centromere (acentric chromosomes) are rapidly lost from cell lines, while fragments that have a centromere are faithfully segregated. The centromere accomplishes this by attaching, via centromere binding proteins, to the spindle fibers during mitosis and meiosis, thus ensuring proper gene segregation during cell divisions.

In contrast to the detailed studies done in *S. cerevisiae* and *S. pombe*, little is known about the molecular structure of functional centromeric DNA of higher eukaryotes. Ultrastructural studies indicate that higher eukaryotic kinetochores, which are specialized complexes of proteins that form on the chromosome during late prophase, are large structures (mammalian kinetochore plates are approximately 0.3 $\mu$m in diameter) which possess multiple microtubule attachment sites (reviewed in Rieder, 1982). It is therefore possible that the centromeric DNA regions of these organisms will be corresponding large, although the minimal amount of DNA necessary for centromere function may be much smaller.

While the above studies have been useful in elucidating the structure and function of centromeres, they have failed to provide a cloned, functional centromere from a higher eukaryotic organism. The extensive literature indicating both the necessity of centromeres for stable inheritance of chromosomes, and the non-functionality of yeast centromeres in higher organisms, demonstrate that cloning of a functional centromere from a higher eukaryote is a necessary first step in the production of artificial chromosomes suitable for use in higher plants and animals. The production of artificial chromosomes with centromeres which function in higher eukaryotes would overcome many of the problems associated with the prior art and represent a significant breakthrough in biotechnology research.

SUMMARY OF THE INVENTION

The current invention overcomes deficiencies in the prior art by providing methods for obtaining a functional plant centromere and uses therefor. More particularly, the present invention provides for the production of a stably inherited plant artificial chromosome.

In a first embodiment, there is provided a method for the identification plant centromeres. Briefly, tetrad analysis measures the recombination frequency between genetic makers and a centromere by analyzing all four products of individual meiosis. A particular advantage arises from the quartet (qrt 1) mutation in *Arabidopsis*, which causes the four products of pollen mother cell meiosis in *Arabidopsis* to remain attached. When used to pollinate a flower, one tetrad can result in the formation of four seeds, and the plants from these seeds can be analyzed genetically. With unordered tetrads, however, such as those produced by *Arabidopsis*, genetic mapping using tetrad analysis requires that two markers be scored simultaneously.

In another embodiment, the present invention provides new plant artificial chromosomes (PLACs) and DNA fragments for the creation thereof. In a preferred embodiment the PLAC will have functional sequences which include telomeres, a plant and/or other autonomous replicating sequence, a centromere, and selectable markers which confer a growth advantage under particular conditions to plant cells carrying the marker, thereby allowing identification of plants, plants cells or cells from any other organism of interest containing the PLAC. A selectable marker may in particular embodiments of the invention function in bacterial cells. The PLAC also may contain "negative" selectable markers which confer susceptibility to an antibiotic, herbicide or other agent, thereby allowing for selection against plants, plant cells or cells of any other organism of interest containing a PLAC. The PLAC also may include genes which control the copy number of the PLAC within a cell. One or more structural genes also may be included in the PLAC. Specifically contemplated as being useful will be as many structural genes as may be inserted into the PLAC while still maintaining a functional vector. This may include one, two, three, four, five, six, seven, eight, nine or more structural genes.

In another embodiment, the invention provides methods for expressing foreign genes in plants, plant cells or cells of any other organism of interest. The foreign genes may be from any organism, including plants, animals and bacteria. It is further contemplated that PLACs could be used to simultaneously transfer multiple foreign genes to a plant comprising entire biochemical or regulatory pathways. In yet another embodiment of the invention, it is contemplated that the PLACs can be used as DNA cloning vectors. Such a vector could be used in plant and animal sequencing projects. The current invention may be of particular use in the cloning of sequences which are "unclonable" in yeast and bacteria, but which may be easier to clone in a plant based system.

In still yet another embodiment of the invention, it is contemplated that the PLACs disclosed herein may be used clone functional segments of DNA such as origins of DNA replication, telomeres, telomere associated genes, nuclear matrix attachment regions (MARs), scaffold attachment regions (SARs), boundary elements, enhancers, silencers, promoters, recombinational hot-spots and centromeres. This embodiment may be carried out by cloning DNA into a defective PLAC which is deficient for one or more type of functional elements. Sequences which complemented such deficient elements would cause the PLAC to be stably inherited. A selectable marker on the PLAC could then be used to select for viable PLAC containing cells which contain cloned functional elements of the type that were non-functional in the defective PLAC.

In still yet another embodiment of the invention, the sequences disclosed herein may be used for the isolation of centromeric sequences from other plant species including agriculturally important species such as *Brassica* species (Broccoli, Cauliflower, Mustard, etc.), and monocots such as wheat and corn. Methods for isolating centromeric sequences using the sequences disclosed herein are well known in the art and are based on shared homology of the centromeric sequences.

In still yet another embodiment of the invention, the artificial chromosome vectors described herein may be used to perform efficient gene replacement studies. At present, gene replacement has been detected on only a few occasions in plant systems and has only been detected at low frequency in mammalian tissue culture systems (see Thomas et al, 1986; Smithies et al., 1985). The reason for this is the high frequency of illegitimate nonhomologous recombination events relative to the frequency of homologous recombination events (the latter are responsible for gene replacement). Artificial chromosomes may participate in homologous recombination preferentially. Since the artificial chromosomes remain intact upon delivery, no recombinogenic broken ends will be generated to serve as substrates for the extremely efficient illegitimate recombination machinery. Thus, the artificial chromosome vectors disclosed by the present invention will be stably maintained in the nucleus through meiosis and available to participate in homology-dependent meiotic recombination. In addition, because in principle, artificial chromosomes of any length could be constructed using the teaching of the present invention, the vectors could be used to introduce extremely long stretches of DNA from the same or any other organism into cells. Specifically contemplated inserts include those from about several base pairs to one hundred megabase pairs, including about 1 kb, 25 kB, 50 kB, 100 kB, 125 kB, 150 kB, 200 kB, 300 kB, 400 kB, 500 kB, 600 kB, 700 kB, 800 kB, 900 kB, 1 MB, 1.25 Mb, 1.5 Mb, 2 Mb, 3 Mb, 5 Mb, 10 Mb, 25 Mb, 50 Mb and 100 Mb.

In still yet another embodiment, the present invention relates to the construction of artificial chromosome vectors for the genetic transformation of plant cells, processes for their preparation, uses of the vectors, and organisms transformed by them. Standard reference works setting forth the general principles of recombinant DNA technology include Lewin, 1985. Other works describe methods and products of genetic engineering; see, e.g., Maniatis et al., 1982; Watson et al., 1983; Setlow et al., 1979; and Dillon et al., 1985.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 4A–Q: Seed stock used for tetrad analysis in *Arabidopsis thaliana*. The individual strains are identified by the strain number. The tetrad member number indicates the tetrad source (i.e. T1 indicates seeds from tetrad number 1, and the numbers −1, −2, −3, or −4 indicate individual members of the tetrad). These strains have been deposited with the *Arabidopsis* Biological Resources Center (ABRC) at Ohio State University under the name of Daphne Preuss.

FIGS. 5A-1 through 5D-2: Genetic markers used to map *Arabidopsis thaliana* centromeres.

In FIGS. 7A–7H, the vectors include a multiple cloning site which can contain recognition sequences for conventional restriction endonucleases with 4–8 bp specificity as well as recognition sequences for very rare cutting enzymes such as, for example, I-Ppo I, I-Ceu I, PI-Tli I, PI-Psp 1, Not I, and PI See I. In FIG. 7A, FIG. 7B, FIG. 7C, FIG. 7D, FIG. 7E, FIG. 7G, and FIG. 7H the centromere is flanked by Lox sites which can act as targets for the site specific recombinase Cre. FIG. 7A: An *E. Coli* plant circular shuttle vector with a plant ARS. FIG. 7B: A plant circular shuttle vector without a plant ARS. The vector relies on a plant origin of replication function found in other plant DNA sequences such as selectable markers. FIG. 7C: A yeast-plant circular shuttle vector with a plant ARS. The yeast ARS is included twice, once on either side of the multiple cloning site to ensure that large inserts are stable. FIG. 7D: A yeast-plant circular shuttle vector without a plant ARS. The vector relies on a plant origin of replication function found in other plant DNA sequences such as selectable markers. The yeast ARS is included twice, once on either side of the multiple cloning site to ensure that large inserts are stable. FIG. 7E: An *E. Coli*—*Agrobacterium*—Plant circular shuttle vector with a plant ARS. Vir functions for T-DNA transfer would be provided in trans by using the appropriate *Agrobacterium* strain. FIG. 7F: An *E. Coli*—*Agrobacterium*—plant circular shuttle vector without a plant ARS. The vector relies on the plant origin of replication function found in other plant DNA sequences such as selectable markers. Vir functions for T-DNA transfer would be provided in trans by using the appropriate *Agrobacterium* strain. FIG. 7G: A linear plant vector with a plant ARS. The linear vector could be assembled in vitro and then transferred into the plant by, for example, mechanical means such as microprojectile bombardment, electroporation, or PEG-mediated transformation. FIG. 7H: A linear plant vector without a plant ARS. The linear vector could be assembled in vitro and then transferred into the plant by, for example, mechanical means such microprojectile bombardment, electroporation, and PEG-mediated transformation.

DETAILED DESCRIPTION OF THE INVENTION

The prior art has failed to provide a centromere which is functional in plants. This failure is exemplified by the general lack of detailed information in the art regarding the centromeres of multicellular organisms in general. To date, the most extensive and reliable characterization of centromere sequences has come from studies of lower eukaryotes such as *S. cerevisiae* and *S. pombe*, where the ability to analyze centromere functions has provided a clear picture of the essential DNA sequences. The *S. cerevisiae* centromere consists of three essential regions, CDEI, CDEII, and CDEIII, totaling only 125 bp, or approximately 0.006 to 0.06% of each yeast chromosome (Carbon et al., 1990; Bloom 1993). *S. pombe* centromeres are between 40 and 100 kB in length and consist of repetitive elements that comprise 1 to 3% of each chromosome (Baum et al., 1994). Subsequent studies, using tetrad analysis to follow the segregation of artificial chromosomes, demonstrated that less than ⅕ of the naturally occurring *S. pombe* centromere is sufficient for centromere function (Baum et al., 1994).

Figure 2:
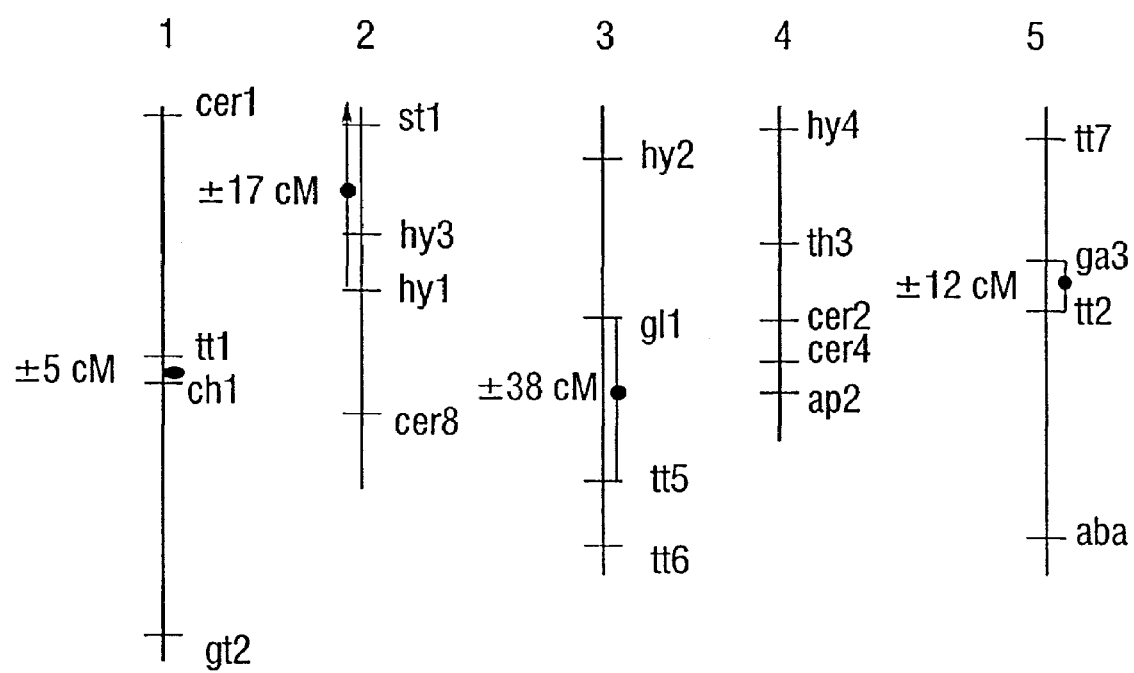
FIG. 2: Low resolution map location of *Arabidopsis* centromeres. Trisomic mapping was used to determine the map position of centromeres on four of the five *Arabidopsis* chromosomes (Koornneef 1983; Sears et al, 1970). For chromosome 4, useful trisomic strains were not obtained. With the methods of Koornneef and Sears et al, 1983. (which rely on low-resolution deletion mapping) the centromere on chromosome 1 was found to lie between the two visible markers, tt1 and ch1, that are separated by 5 cM. Centromere positions on the other chromosomes are mapped to a lower resolution.
Figure 3A:
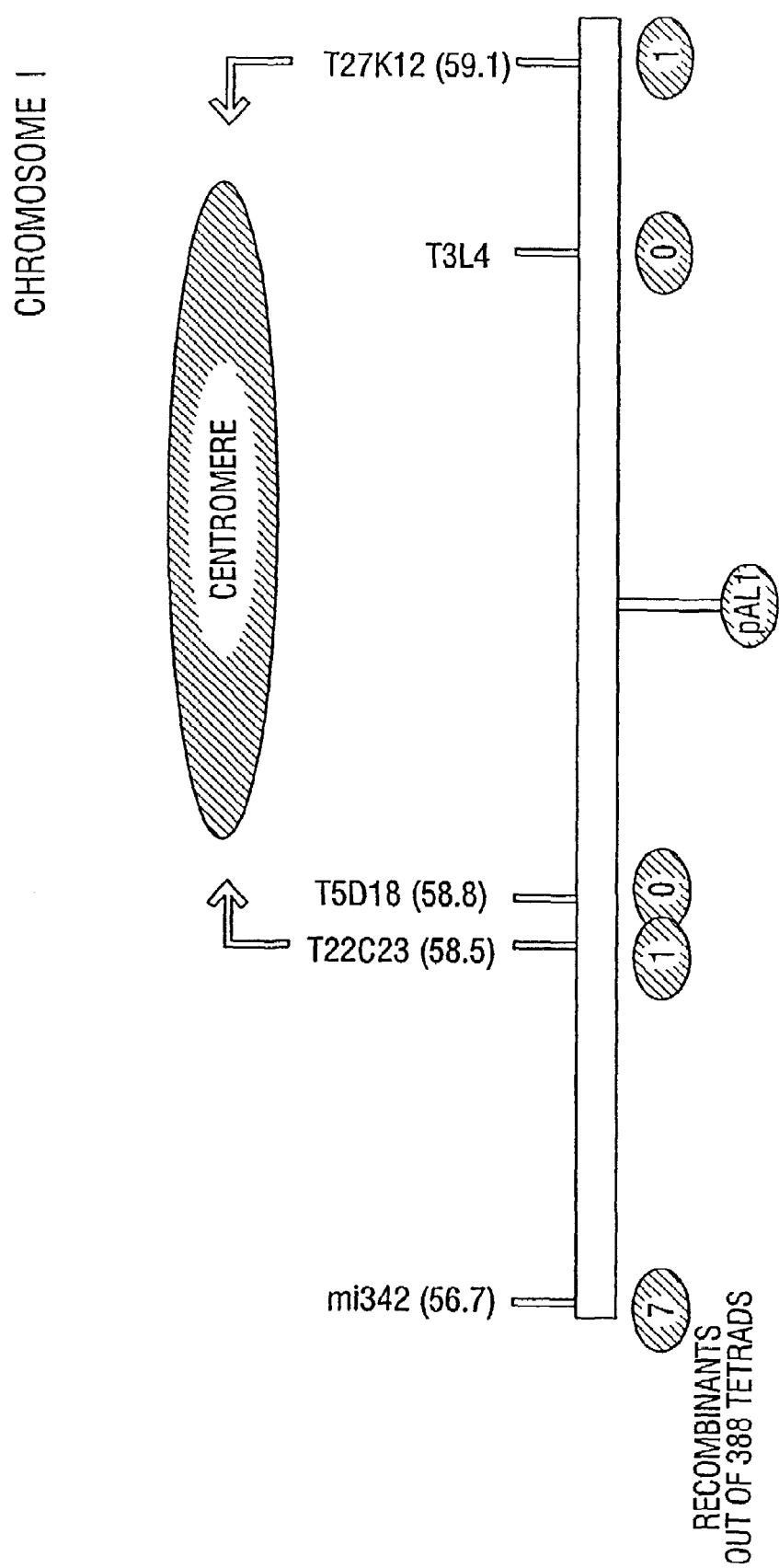
FIGS. 3A–E: Map location of *Arabidopsis thaliana* centromeres on chromosomes 1–5. Centromeres were mapped by tetrad analysis as described below. Genetic markers used to map the centromeres are displayed above the chromosomes and are designated by their cM values (all cM values were derived from the Lister and Dean recombinant inbred map at the web site: http://genome www3.stanford.edu/atdb_welcome.html).
Figure 3B:
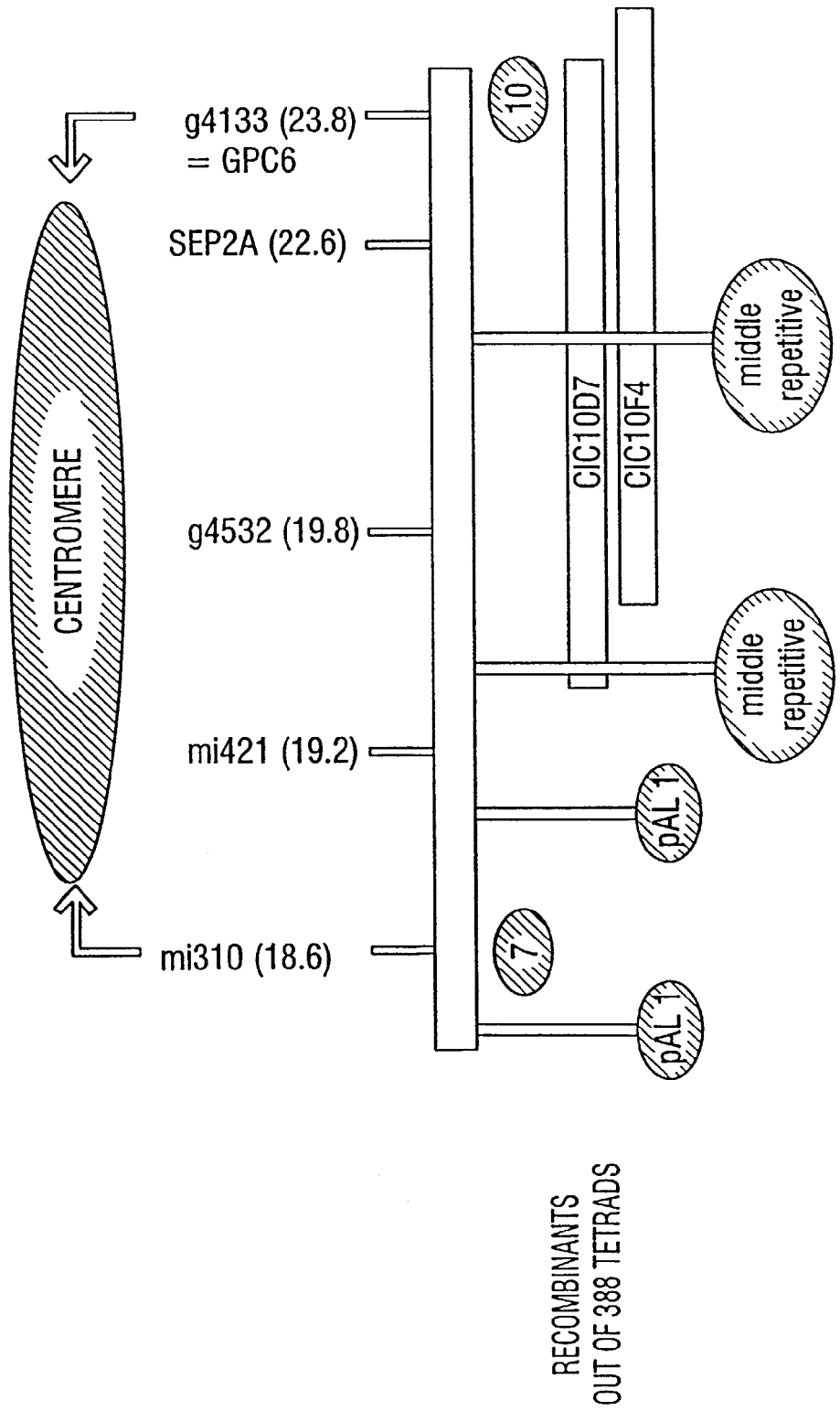
Figure 3C:
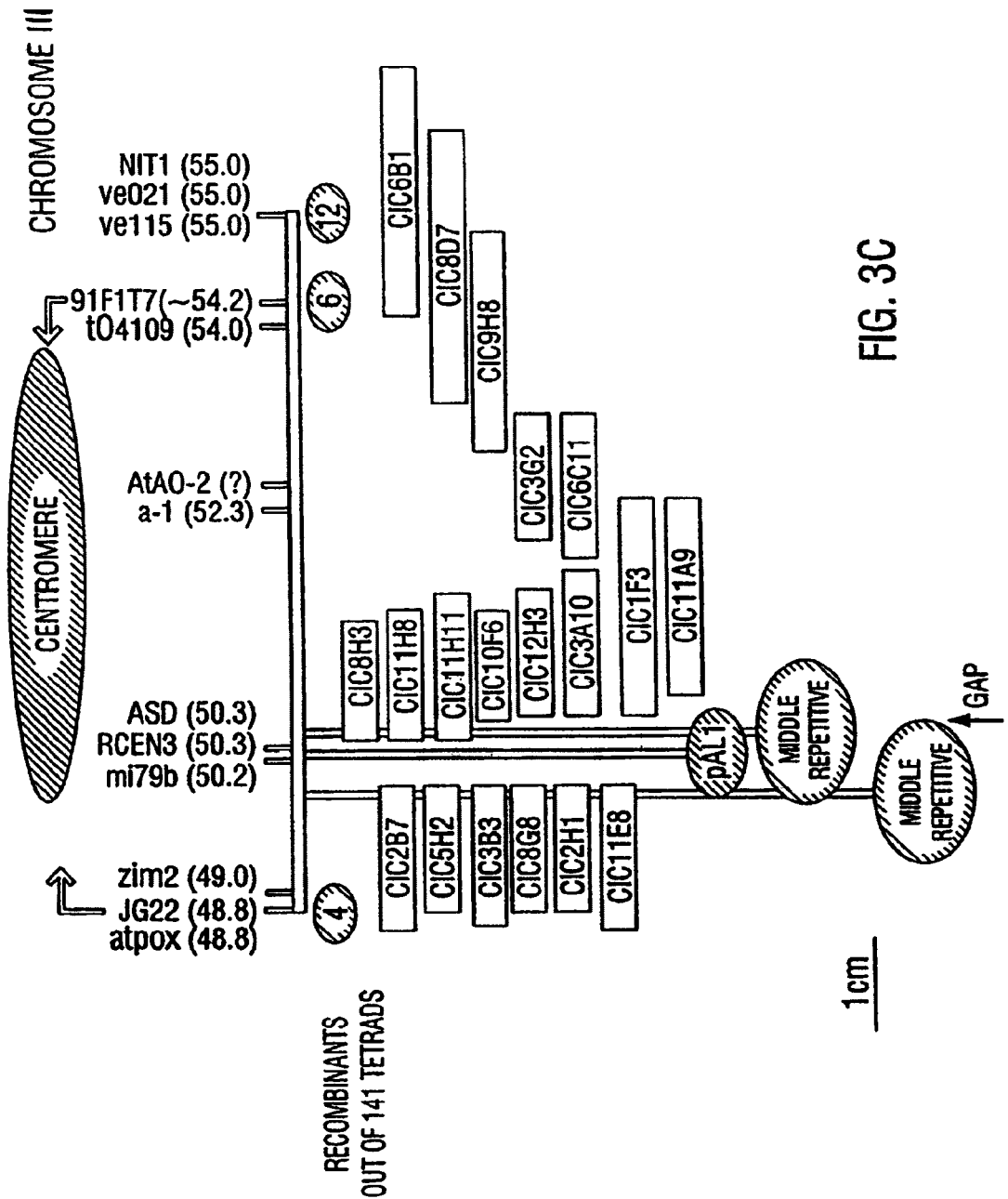
Figure 3D:
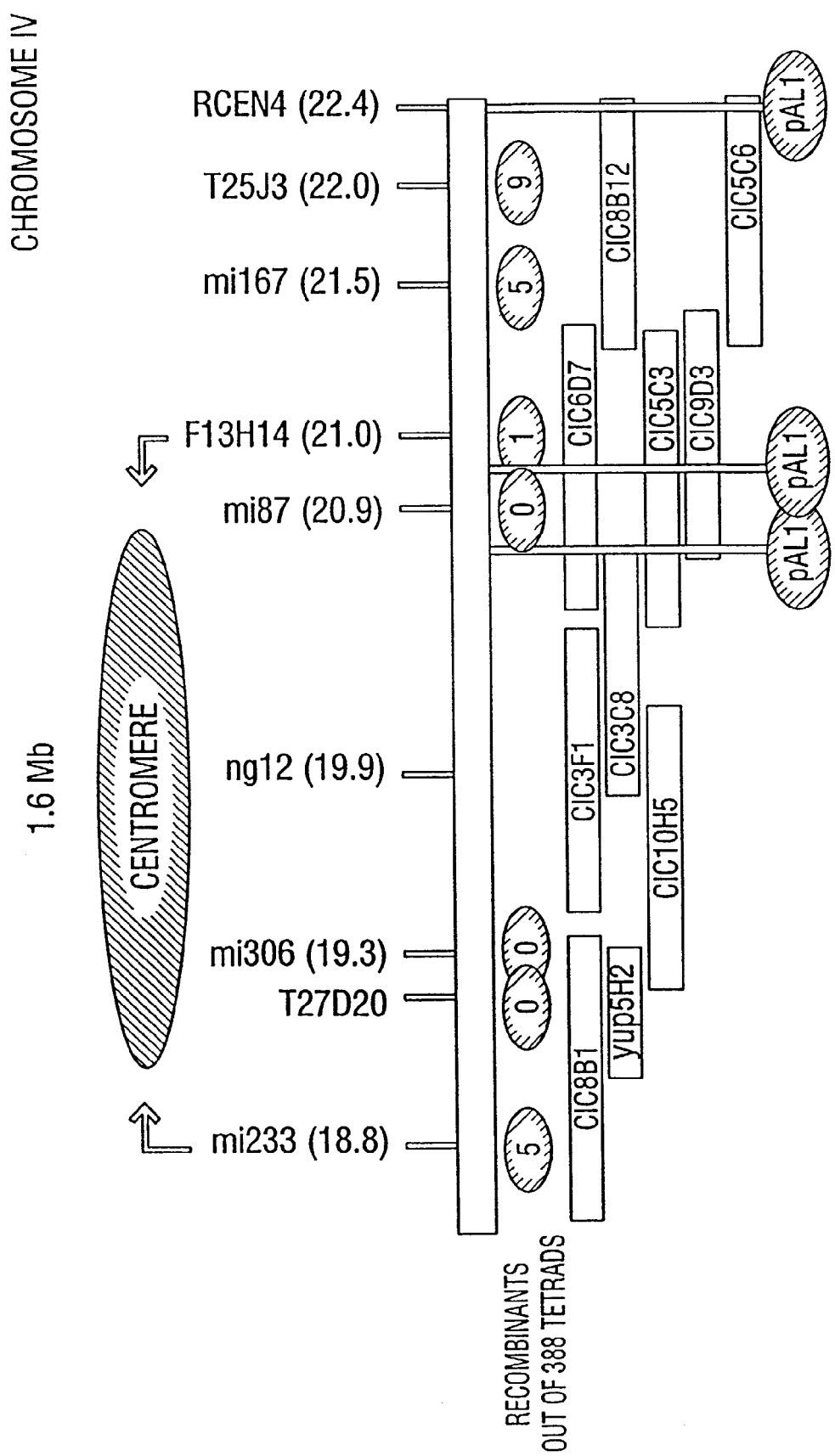
Figure 3E:
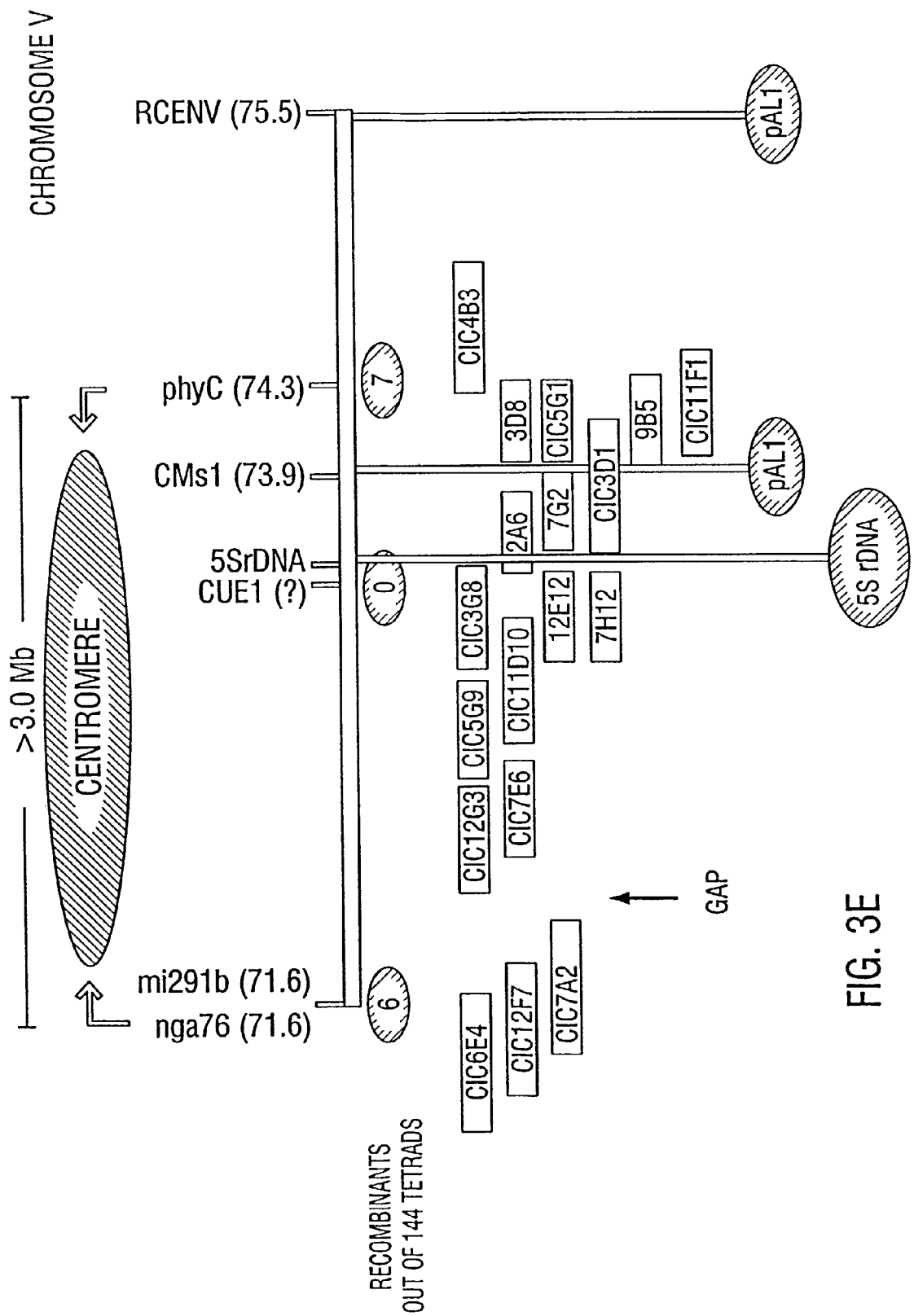

In contrast, the centromeres of mammals and other higher eukaryotes are poorly defined. Although DNA fragments that hybridize to centromeric regions in higher eukaryotes have been identified, little is known regarding the functionality of these sequences (see Tyler-Smith et al., 1993). In many cases centromere repeats correlate with centromere location, with probes to the repeats mapping both cytologically and genetically to centromere regions. Many of these sequences are tandemly-repeated satellite elements and dispersed repeated sequences in arrays ranging from 300 kB to 5000 kB in length (Willard 1990). To date, only one of these repeats, a 171 bp element known as the alphoid satellite, has been shown by in situ hybridization to be present at each human centromere (Tyler-Smith et al., 1993). Whether repeats themselves represent functional centromeres remains controversial, as other genomic DNA is required to confer inheritance upon a region of DNA (Willard, 1997). Alternatively, the positions of some higher eukaryotic centromeres have been estimated by analyzing the segregation of chromosome fragments. This approach is imprecise, however, because a limited set of fragments can be obtained, and because normal centromere function is influenced by surrounding chromosomal sequences (for example, see Koornneef, 1983; FIG. 2).

A more precise method for mapping centromeres that can be used in intact chromosomes is tetrad analysis (Mortimer et al., 1981), which provides a functional definition of a centromere in its native chromosomal context. At present, the only centromeres that have been mapped in this manner are from unicellular eukaryotes, including the yeasts *Saccharomyces cerevisiae, Schizosaccharomyces pombe*, and *Kluyveromyces lactis* (Carbon et al., 1990; Hegemann et al., 1993). In these systems, accurate mapping of the centromeres made it possible to clone centromeric DNA, using a chromosome walking strategy (Clarke et al., 1980). Subsequently, artificial chromosome assays were used to define more precisely the centromere sequences (Hegemann et al., 1993; Baum et al., 1994).

Attempts to develop a reliable centromeric assay in mammals have yielded ambiguous results. For example, Hadlaczky et al., (1991) identified a 14 kB human fragment that can, at low frequency, result in de novo centromere formation in a mouse cell line. In situ hybridization studies, however, have shown that this fragment is absent from naturally occurring centromeres, calling into question the reliability of this approach for testing centromere function (Tyler-Smith et al., 1993). Similarly, transfection of alphoid satellites into cell lines results in the formation of new chromosomes, yet these chromosomes also contain host sequences that could contribute centromere activity (Haaf et al., 1992; Willard, 1997). Further, the novel chromosomes can have alphoid DNA spread throughout their length yet have only a single centromeric constriction, indicating that a block of alphoid DNA alone may be insufficient for centromere function (Tyler-Smith et al., 1993).

Although plant centromeres can be visualized easily in condensed chromosomes, they have not been characterized as extensively as centromeres from yeast or mammals. Genetic characterization has relied on segregation analysis of chromosome fragments, and in particular on analysis of trisomic strains that carry a genetically marked, telocentric fragment (for example, see Koornneef 1983; FIG. 2). In addition, repetitive elements have been identified that are either genetically (Richards et al., 1991) or physically (Alfenito et al., 1993; Maluszynska et al., 1991) linked to a centromere. In no case, however, has the functional significance of these sequences been tested.

Cytology in *Arabidopsis thaliana* has served to correlate centromere structure with repeat sequences. A fluorescent dye, DAPI, allows visualization of centromeric chromatin domains in metaphase chromosomes. A fluorescence in situ hybridization (FISH) probe based on 180 bp pAL1 repeat sequences colocalized with the DAPI signature near the centromeres of all five *Arabidopsis* chromosomes (Maluszynska et al., 1991; Martinez-Zapater et al., 1986), however this repeat probe also hybridizes within noncentromeric regions of the chromosomes. Although a functional role for pAL1 has been proposed, more recent studies have failed to detect this sequence near the centromeres in species closely related to *Arabidopsis thaliana* (Maluszynska et al., 1993). These results are particularly troubling because one of the species tested, *A. pumila*, is thought be an amphidiploid, derived from a cross between *A. thaliana* and another close relative (Maluszynska et al., 1991; Price et al., 1995). Another repetitive sequence, pAtT12, has been genetically mapped to within 5 cM of the centromere on chromosome 1 and to the central region of chromosome 5 (Richards et al., 1991), although its presence on other chromosomes has not been established. Like pAL1, a role for pAtT12 in centromere function remains to be demonstrated.

Due to the fact that kinetochores constitute a necessary link between centromeric DNA and the spindle apparatus, the proteins that are associated with these structures recently have been the focus of intense investigation (Bloom 1993; Earnshaw 1991). Human autoantibodies that bind specifically in the vicinity of the centromere have facilitated the cloning of centromere-associated proteins (CENPs, Rattner 1991), and at least one of these proteins belongs to the kinesin superfamily of microtubule-based motors (Yen 1991). Yeast centromere-binding proteins also have been identified, both through genetic and biochemical studies (Bloom 1993; Lechner et al., 1991). Although the basic features of mitosis and meiosis (including spindle attachment, chromosome pairing, and chromosome separation) are conserved among all eukaryotes, a comparison of the known centromere-binding proteins from yeast and humans reveals little similarity (Bloom, 1993; Earnshaw and Cooke, 1989).

The centromeres of *Arabidopsis thaliana* have been mapped using trisomic strains, where the segregation of chromosome fragments (Koornneef 1983) or whole chromosomes (Sears et al., 1970) was used to localize four of the centromeres to within 5, 12, 17 and 38 cM, respectively (FIG. 2). These positions have not been refined by more recent studies because the method is limited, not only by the difficulty in obtaining viable trisomic strains, but also by the inaccuracy of comparing recombination frequencies in chromosome fragments to those in intact chromosomes (Koornneef 1983). These factors introduce significant error into the calculated position of the centromere, and in *Arabidopsis*, where 1 cM corresponds roughly to 200 kB (Koornneef 1987; Hwang et al., 1991), this method did not map any of the centromeres with sufficient precision to make chromosome walking strategies practical.

I. Tetrad Analysis

Figure 1:
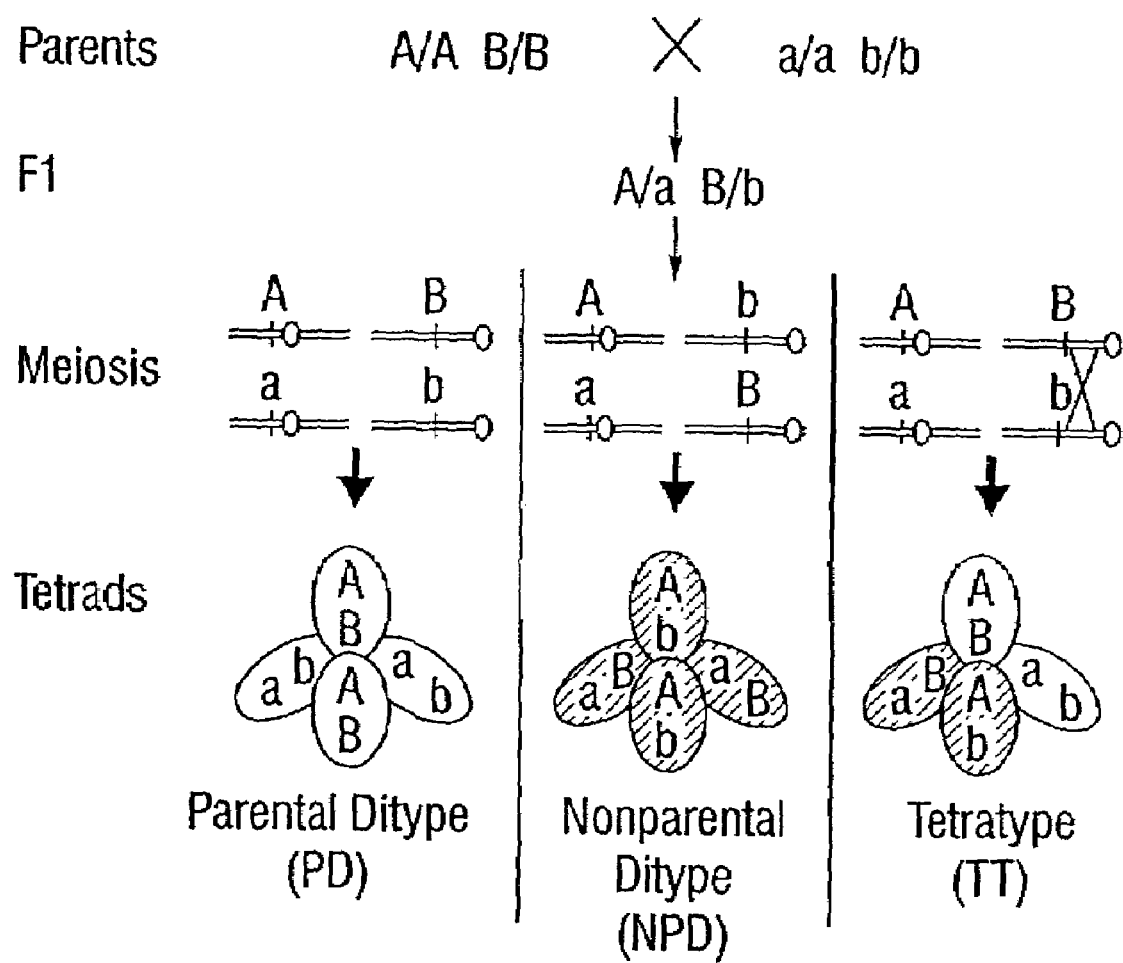
FIG. 1: Centromere mapping with unordered tetrads: A cross of two parents (AABB×aabb), in which "A" is on the centromere of one chromosome, and "B" is linked to the centromere of a second chromosome. At meiosis, the A and B chromosomes assort independently, resulting in equivalent numbers of parental ditype (PD) and nonparental ditype (NPD) tetrads (recombinant progeny are shown in gray). Tetratype tetrads (TT) result only from a crossover between "B" and the centromere.

With tetrad analysis, the recombination frequency between genetic markers and a centromere can be measured directly (FIG. 1). This method requires analysis of all four products of individual meiosis, and it has not been applied previously to multicellular eukaryotes because their meiotic products typically are dissociated. Identification of the quartet mutation makes tetrad analysis possible for the first time in a multicellular genetic model system (Preuss et al., 1994). The quartet (qrt 1) mutation causes the four products of pollen mother cell meiosis in *Arabidopsis* to remain attached. When used to pollinate a flower, one tetrad can result in the formation of four seeds, and the plants from these seeds can be analyzed genetically.

With unordered tetrads, such as those produced by *S. cerevisiae* or *Arabidopsis*, genetic mapping using tetrad analysis requires that two markers be scored simultaneously (Whitehouse 1950). Tetrads fall into different classes depending on whether the markers are in a parental (non-recombinant) or nonparental (recombinant) configuration (FIG. 1). A tetrad with only nonrecombinant members is referred to as a parental ditype (PD); one with only recombinant members as a nonparental ditype (NPD); and a tetrad with two recombinant and two nonrecombinant members as a tetratype (TT) (Perkins 1953). If two genetic loci are on different chromosomes, and thus assort independently, the frequency of tetratype (crossover products) versus parental or nonparental assortment ditype (noncrossover products) depends on the frequency of crossover between each of the two loci and their respective centromeres.

Tetratype tetrads arise only when a crossover has occurred between a marker in question and its centromere. Thus, to identify genes that are closely linked to the centromere, markers are examined in a pair-wise fashion until the TT frequency approaches zero. The genetic distance (in centimorgans, cM) between the markers and their respective centromeres is defined by the function [(1/2)TT]/100 (Mortimer et al., 1981). Because positional information obtained by tetrad analysis is a representation of physical distance between two points, as one approaches the centromere the chance of a recombination event declines.

Tetrad analysis has been used to genetically track centromeres in yeasts and other fungi in which products of a single meioses can be collected. The budding yeast *Saccharomyces cerevisiae* lacks mitotic condensation and thus cytogenetics (Hegemann et al., 1993), yet due to tetrad analysis, has served as the vehicle of discovery for centromere function. Meiosis is followed by the generation of four spores held within an ascus and these can be directly assayed for gene segregation.

Figure 6:
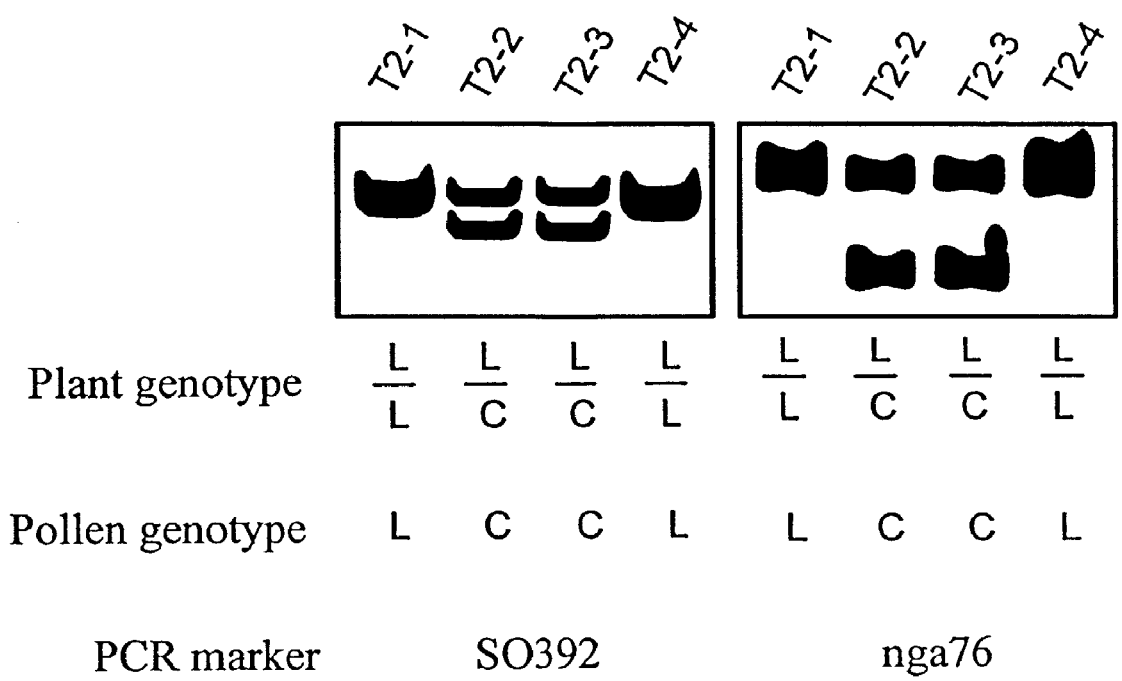
FIG. 6: Scoring PCR-based markers for tetrad analysis. The genotype of the progeny from one pollen tetrad (T2) was determined for two genetic markers ($SO_{392}$ and nga76). Analysis of the four progeny plants (T2-1 through T24) using PCR and gel electrophoresis allows the genotype of the plant to be determined, and the genotype of the pollen parent to be inferred.
Figure 7A:
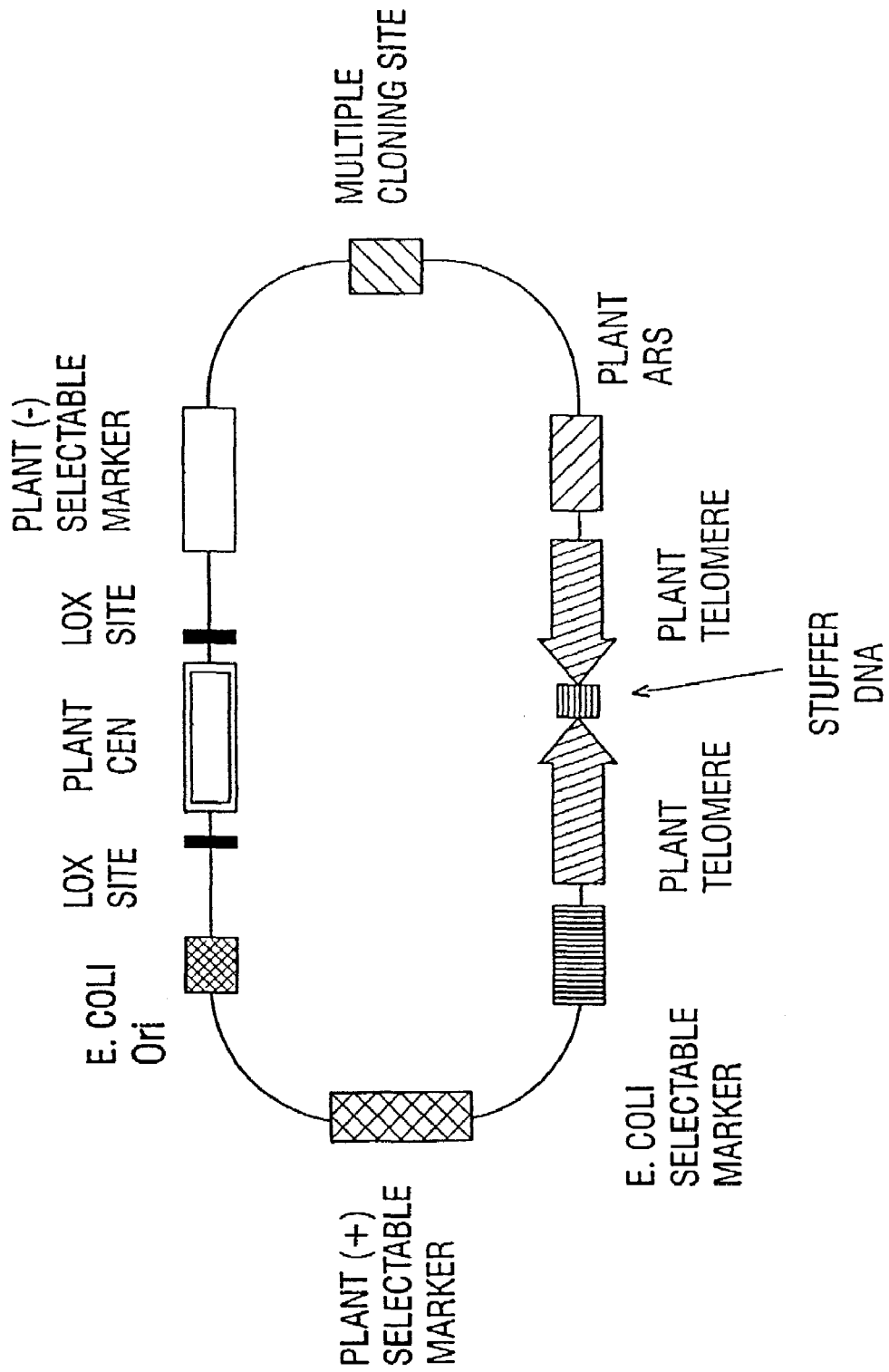
FIGS. 7A–7H: Exemplary PLAC vectors: The vectors shown in FIG. 7A, FIG. 7B, FIG. 7E, and FIG. 7F have an *E. coli* origin of replication which can be high copy number, low copy number or single copy.
Figure 7B:
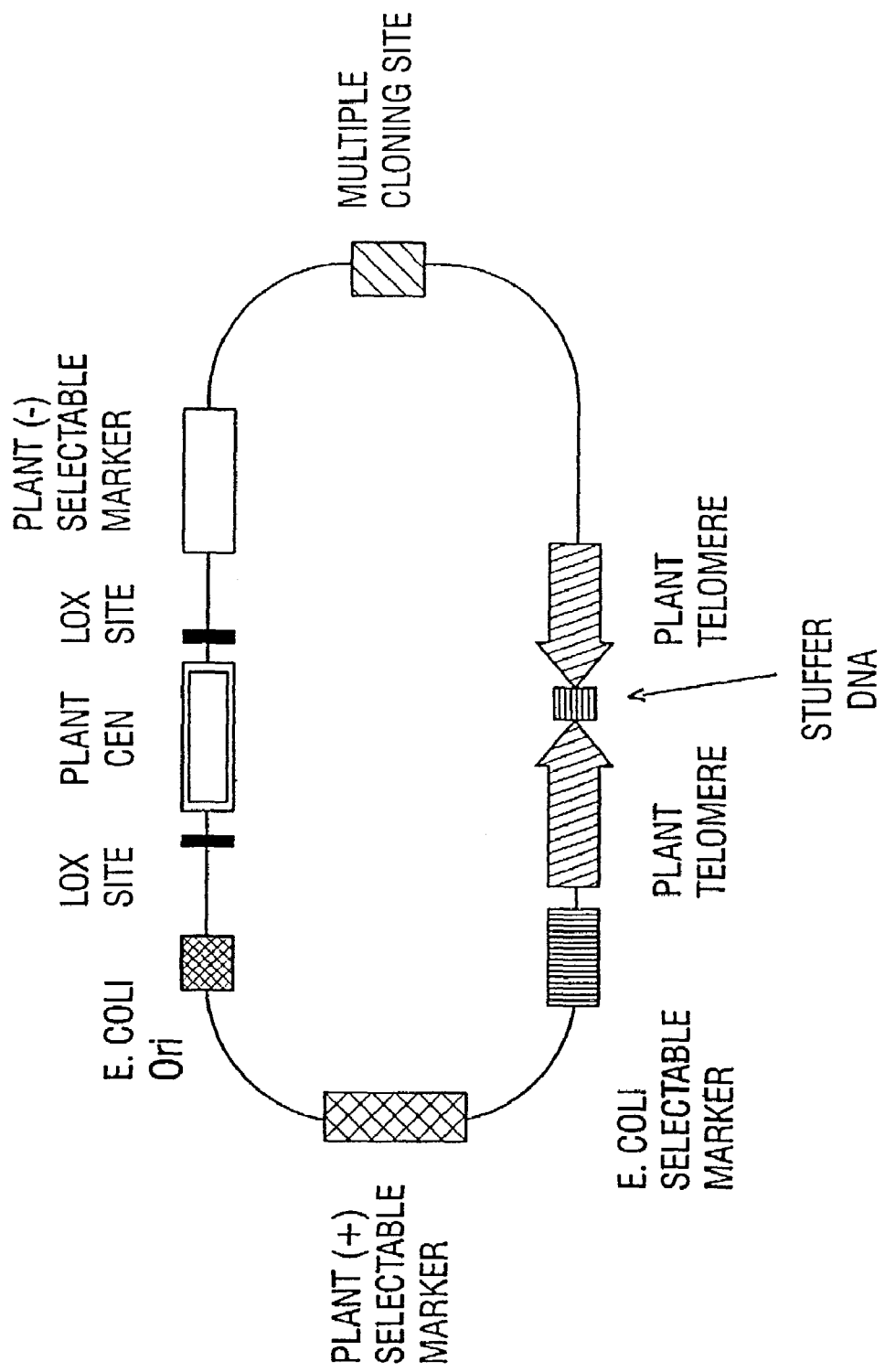
Figure 7C:
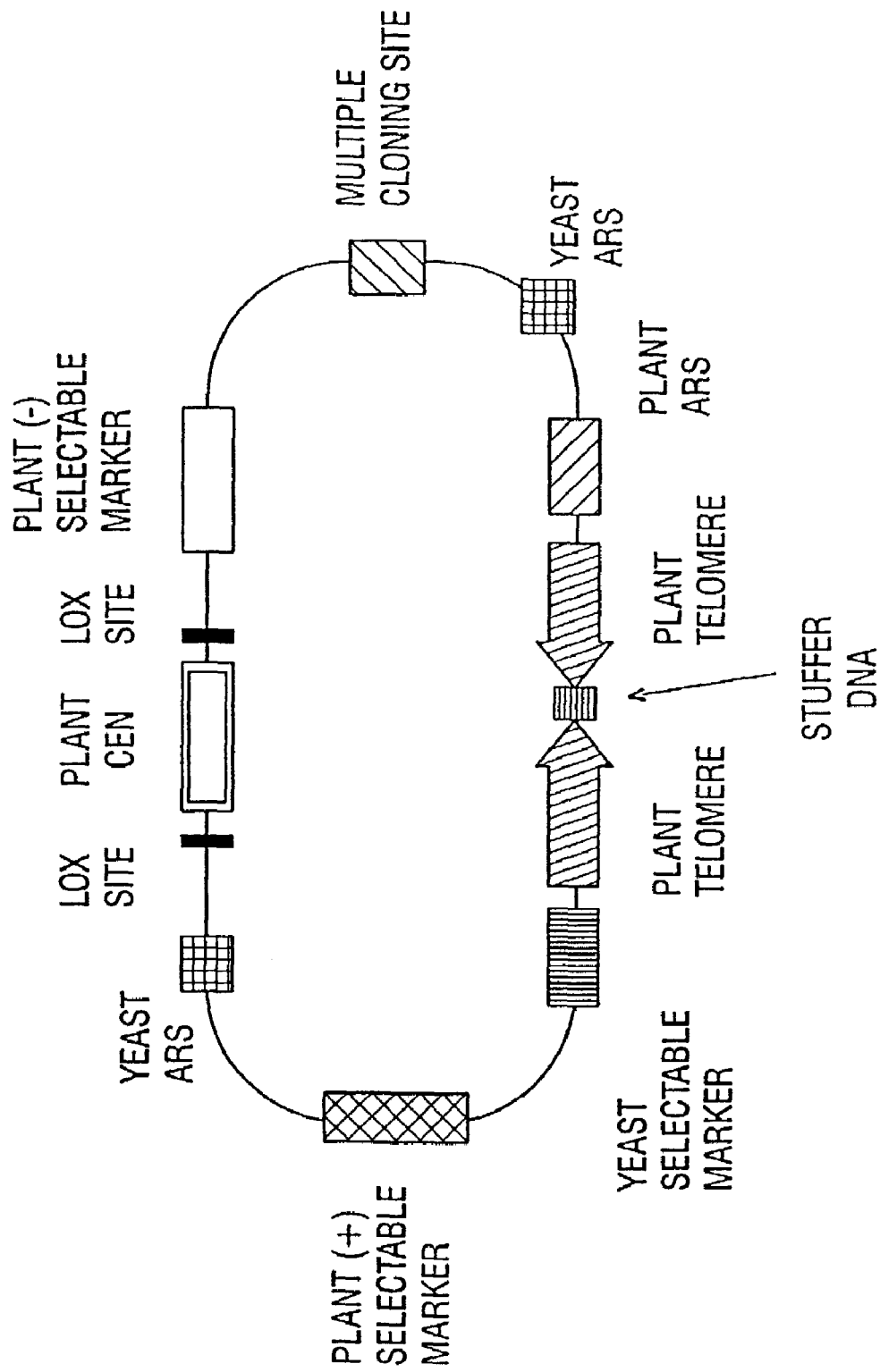
Figure 7D:
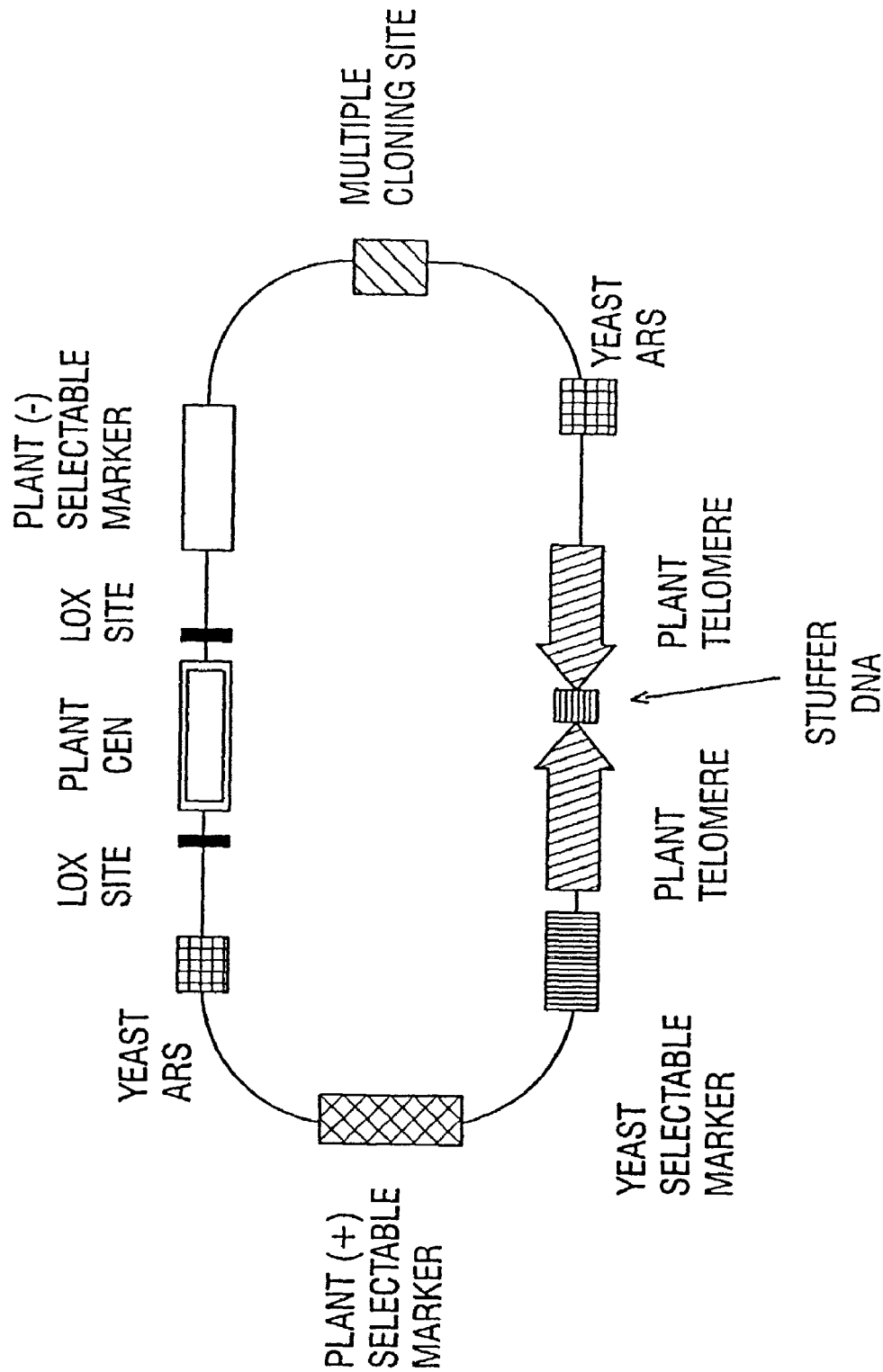
Figure 7E:
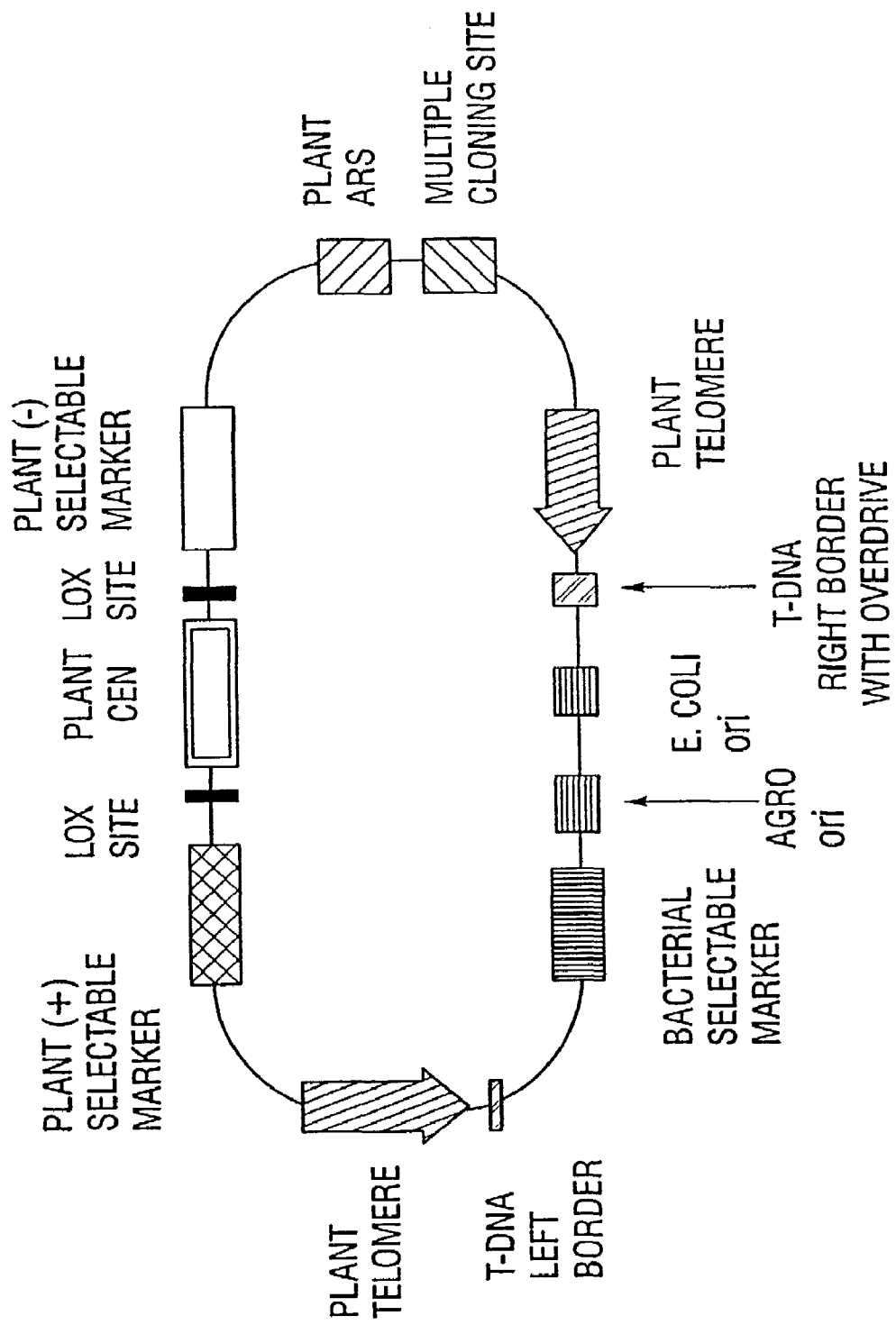
Figure 7F:
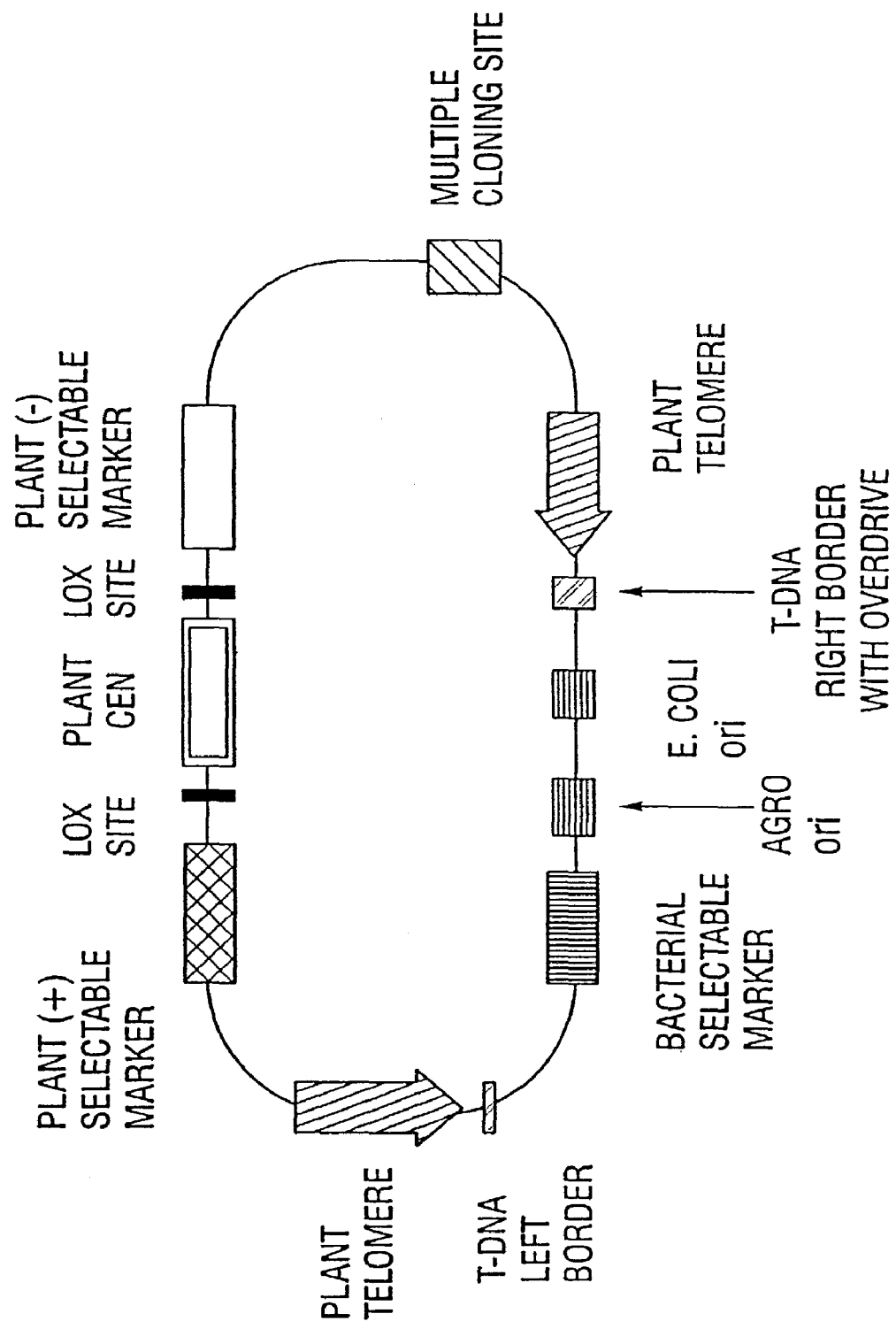
Figure 7G:
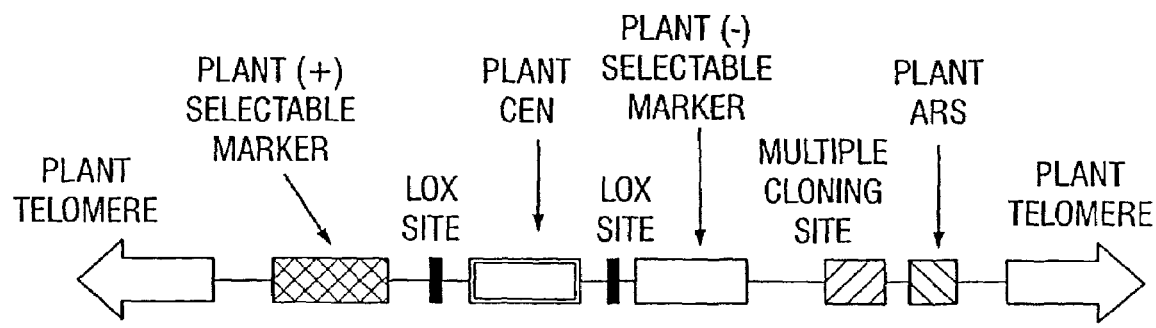
Figure 7H:
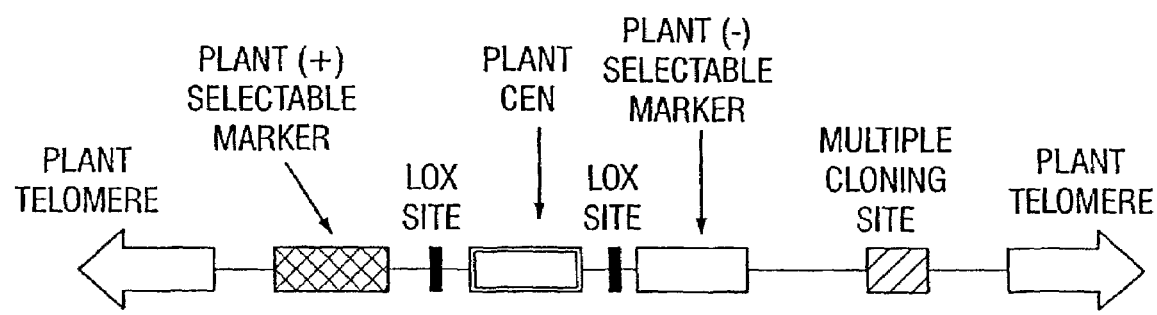

The recessive qrt1 mutation makes it possible to perform tetrad analysis in *Arabidopsis* by causing the four products of meiosis to remain attached (Preuss et al., 1994; and Smythe 1994; both incorporated herein by reference). As previously shown, within each tetrad, genetic loci segregate in a 2:2 ratio (FIG. 6). Individual tetrads can be manipulated onto flowers with a fine brush (at a rate of 20 tetrads per hour), and in 30% of such crosses, four viable seeds can be obtained (Preuss et al., 1994).

Mapping centromeres with high precision requires a dense genetic map, and although the current *Arabidopsis* map contains many visible markers, it would be laborious to cross each into the qrtI background. Alternatively, hundreds of DNA polymorphisms can be introduced simultaneously by crossing two different strains, both containing the qrtI mutation. A dense RFLP map (Chang et al., 1988) and PCR-based maps (Konieczny et al., 1993; Bell et al., 1994) have been generated in *Arabidopsis* from crosses of the Landsberg and Columbia strains (*Arabidopsis* map and genetic marker data is available from the internet at http://genome-www.stanford.edu/*Arabidopsis* and http://cbil-.humgen.upenn.edu/atgc/sslp_info/sslp.html). These strains differ by 1% at the DNA sequence level and have colinear genetic maps (Chang et al., 1988; Koornneef, 1987).

Centromere mapping with tetrad analysis requires simultaneous analysis of two markers, one of which must be centromere-linked (FIG. 1). To identify these centromere-linked markers, markers distributed across all 5 chromosomes were scored and compared in a pairwise fashion.

Initially, genetic markers that can be scored by PCR analysis were tested (Konieczny et al., 1993; Bell et al., 1994). Such markers are sufficiently dense to map any locus to ±10 cM, and as additional PCR-detectable polymorphisms are identified they are incorporated into the analyses. As higher resolution mapping becomes necessary, selected RFLPs, from the existing set of over 350 markers will be scored. In addition, as described in FIG. 5, new CAPS and SSLP markers useful for mapping the centromere can be readily identified.

II. Tetrad Sets

To date, progeny plants from 388 isolated tetrad seed sets have been germinated and leaf tissue collected and stored from each of the tetrad progeny plants. The leaf tissue from individual plants was used to make DNA for PCR based marker analysis. The plants also were allowed to self-fertilize and the seed they produced was collected (a list of the seed stock of informative individuals used for tetrad analysis is given in FIG. 4). From each of these individual seed sets, seedlings can be germinated and their tissues utilized for making genomic DNA. Tissue pooled from multiple seedlings is useful for making Southern genomic DNA blots for the analysis of restriction fragment length polymorphisms (RFLPs). Informative plants which have been used for tetrad analysis are given in FIG. 4.

III. Mapping Strategy

The initial mapping of the centromeres was completed with selected PCR™ based markers (such as CAPS and SSLPs) (FIG. 5). These markers were selected from the large number of markers available for *Arabidopsis* and are distributed across the genetic map. Due to the fact that analysis of RFLP markers is labor intensive, those markers that could be analyzed with PCR™-based markers were surveyed first. Only a subset of the original 388 tetrads have provided crossovers close enough to their centromeres as to require the use of RFLP marker segregation analysis. For those tetrads in which existing markers do not identify the region of crossover between centromere and marker, new markers may be developed. This may be accomplished by screening cloned sequences in regions of interest for new potential markers, i.e., RFLPs, CAPS, SSLPs, and the like. The new markers may then be used to generate new data with the relevant tetrads. In addition to the markers in centromeric regions, the segregation of two markers per chromosome that are both, far from, and flank the centromeric regions were assessed. Data from these markers will often be tetratype and thus identify whether a Landsberg to Columbia crossover or a Columbia to Landsberg crossover is visible as the centromere is approached.

Codominant cleaved amplified polymorphic sequences (CAPS) were amplified by PCR™. The PCR™ products were observed on agarose gels prior to cleavage by restriction enzymes. Once cleaved, the products were scored for marker segregation on agarose or acrylamide gels. Simple sequence length polymorphisms (SSLPs) also were amplified by PCR™. The PCR™ products were directly scored by polyacrylamide gel electrophoresis (PAGE), or on agarose gels.

IV. High Resolution Positioning of Centromeres on the Genetic Map

Southern genomic DNA blots in combination with RFLP analysis may be used to map centromeres with a high degree of resolution. The stored seedling tissue provides the necessary amount of DNA for analysis of the restriction fragments. Southern blots are hybridized to probes labeled by radioactive or non-radioactive methods.

It may, in many cases, be desired to identify new polymorphic DNA markers which are closely linked to the target region. In some cases this can be readily done. For example when comparing Landsberg and Columbia DNA, a polymorphic Sau3A site can be found for about every 8 to 20 kB surveyed. Subtractive methods are available for identifying such polymorphisms (Rosenberg et al., 1994), and these subtractions may be performed using DNA from selected, centromeric YAC clones. Screens for RFLP markers potentially linked to centromeres also can be performed using DNA fragments from a centromere-linked YAC clone to probe blots of Landsberg and Columbia genomic DNA that has been digested with a panel of restriction enzymes.

V. Isolation of Centromere Containing DNA Fragments

Using the markers flanking each centromere (see FIG. 3) it is possible to purify a contiguous DNA fragment that contains both flanking markers and the centromere encoded between those markers. In order to carry this out, very large DNA fragments up to the size of an entire chromosome are prepared by embedding Arabidopsis tissues in agarose using, for example, the method described by Copenhaver et al., (1995). These large pieces of DNA can be digested in the agarose with any restriction enzyme. Those restriction enzymes which will be particularly useful for isolating intact centromeres include enzymes which yield very large DNA fragments. Such restriction enzymes include those with specificities greater than six base pairs such as, for example, Asc I, Bae I, BbvC I, Fse I, Not I, Pac I, Pme I, PpuM I, Rsr II, SanD I, Sap I, SexA I, Sfi I, Sgf I, SgrA I, Sbf I, Srf I, Sse8387 I, Sse8647 I, Swa, UbaD I, and UbaE I, or any other enzyme that cuts at a low frequency within the Arabidopsis genome, and specifically within the centromeric region. Alternatively, a partial digest with a more frequent cutting restriction enzyme could be used.

The large DNA fragments produced by digestion with restriction enzymes are then separated by size using pulsed-field gel electrophoresis (PFGE) (Schwartz et al., 1982). Specifically, Contour-clamped Homogeneous Electric Field (CHEF) electrophoresis (a variety of PFGE) can be used to separate DNA molecules as large as 10 Mb (Chu et al., 1985). Large DNA fragments resolved on CHEF gels can then be analyzed using standard Southern hybridization techniques to identify and measure the size of those fragments which contain both centromere flanking markers and therefor, the centromere. After determining the size of the centromere containing fragment by comparison with known size standards, the region from the gel that contains the centromere fragment can be cut out of a duplicate gel. This centromeric DNA can then be analyzed, sequenced, and used in a variety of applications, as described below, including the construction of plant artificial chromosomes (PLACs). As indicated in detail below, PLACs can be constructed by attaching telomeres and selectable markers to the centromere fragment cut from the agarose gel using standard techniques which allow DNA ligation within the gel slice. Plant cells can then be transformed with this hybrid DNA molecule using the techniques described herein below.

VI. PLAC Constructs

In light of the instant disclosure it will be possible for those of ordinary skill in the art to construct the artificial chromosomes described herein. Useful construction methods are well-known (see, for example, Maniatis et al., 1982). As constructed, the PLAC will preferably include at least an autonomous replication sequence (ARS) functional in plants, a centromere functional in plants, and telomeres which are functional in plants.

In addition to the basic elements, positive and negative selectable plain makers (e.g., antibiotic or herbicide resistance genes), and a cloning site for insertion of foreign DNA will preferably be included. In addition, a visible marker, such as green fluorescent protein, also may be desirable. In order to propagate the vectors in E. coli, it is necessary to convert the linear molecule into a circle by addition of a stuffer fragment between the telomeres. Inclusion of an E. coli plasmid replication origin and selectable marker also may be preferred. It also may be desirable to include Agrobacterium sequences to improve replication and transfer to plant cells. Exemplary artificial chromosome constructs are given in FIGS. 7A–7H, although it will be apparent to those in skill art that many changes may be made in the order and types of elements present in these constructs and still obtain a functional artificial chromosome within the scope of the instant invention.

Artificial plant chromosomes which replicate in yeast also may be constructed to take advantage of the large insert capacity and stability of repetitive DNA inserts afforded by this system (see Burke et al., 1987). In this case, yeast ARS and CEN sequences are added to the vector. The artificial chromosome is maintained in yeast as a circular molecule using a stuffer fragment to separate the telomeres.

A fragment of DNA, from any source whatsoever, may be purified and inserted into an artificial plant chromosome at any appropriate restriction endonuclease cleavage site. The DNA segment usually will include various regulatory signals for the expression of proteins encoded by the fragment. Alternatively, regulatory signals resident in the artificial chromosome may be utilized.

The techniques and procedures required to accomplish insertion are well-known in the art (see Maniatis et al., 1982). Typically, this is accomplished by incubating a circular plasmid or a linear DNA fragment in the presence of a restriction endonuclease such that the restriction endonuclease cleaves the DNA molecule. Endonucleases preferentially break the internal phosphodiester bonds of polynucleotide chains. They may be relatively unspecific, cutting polynucleotide bonds regardless of the surrounding nucleotide sequence. However, the endonucleases which cleave only a specific nucleotide sequence are called restriction enzymes. Restriction endonucleases generally internally cleave DNA molecules at specific recognition sites, making breaks within "recognition" sequences that in many, but not all, cases exhibit two-fold symmetry around a given point. Such enzymes typically create double-stranded breaks.

Many of these enzymes make a staggered cleavage, yielding DNA fragments with protruding single-stranded 5' or 3' termini. Such ends are said to be "sticky" or "cohesive" because they will hydrogen bond to complementary 3' or 5' ends. As a result, the end of any DNA fragment produced by an enzyme, such as EcoRI, can anneal with any other fragment produced by that enzyme. This properly allows splicing of foreign genes into plasmids, for example. Some restriction endonucleases that may be particularly useful with the current invention include HindIII, PstI, EcoRI, and BamHI.

Some endonucleases create fragments that have blunt ends, that is, that lack any protruding single strands. An alternative way to create blunt ends is to use a restriction enzyme that leaves overhangs, but to fill in the overhangs with a polymerase, such as klenow, thereby resulting in blunt ends. When DNA has been cleaved with restriction enzymes that cut across both strands at the same position, blunt end ligation can be used to join the fragments directly together. The advantage of this technique is that any pair of ends may be joined together, irrespective of sequence.

Those nucleases that preferentially break off terminal nucleotides are referred to as exonucleases. For example, small deletions can be produced in any DNA molecule by treatment with an exonuclease which starts from each 3' end of the DNA and chews away single strands in a 3' to 5' direction, creating a population of DNA molecules with single-stranded fragments at each end, some containing terminal nucleotides. Similarly, exonucleases that digest DNA from the 5' end or enzymes that remove nucleotides from both strands have often been used. Some exonucleases which may be particularly useful in the present invention include Bal31, SI, and ExoIII. These nucleolytic reactions can be controlled by varying the time of incubation, the temperature, and the enzyme concentration needed to make deletions. Phosphatases and kinases also may be used to control which fragments have ends which can be joined. Examples of useful phosphatases include shrimp alkaline phosphatase and calf intestinal alkaline phosphatase. An example of a useful kinase is T4 polynucleotide kinase.

Once the source DNA sequences and vector sequences have been cleaved and modified to generate appropriate ends they are incubated together with enzymes capable of mediating the ligation of the two DNA molecules. Particularly useful enzymes for this purpose include T4 ligase, E. Coli ligase, or other similar enzymes. The action of these enzymes results in the sealing of the linear DNA to produce a larger DNA molecule containing the desired fragment (see, for example, U.S. Pat. Nos. 4,237,224; 4,264,731; 4,273,875; 4,322,499 and 4,336,336, which are specifically incorporated herein by reference).

It is to be understood that the termini of the linearized plasmid and the termini of the DNA fragment being inserted must be complementary or blunt in order for the ligation reaction to be successful. Suitable complementarity can be achieved by choosing appropriate restriction endonucleases (i.e., if the fragment is produced by the same restriction endonuclease or one that generates the same overhang as that used to linearize the plasmid, then the termini of both molecules will be complementary). As discussed previously, in a preferred embodiment, at least two classes of the vectors used in the present invention are adapted to receive the foreign oligonucleotide fragments in only one orientation. After joining the DNA segment to the vector, the resulting hybrid DNA can then be selected from among the large population of clones or libraries.

A method useful for the molecular cloning of DNA sequences includes in vitro joining of DNA segments, fragmented from a source high molecular weight genomic DNA, to vector DNA molecules capable of independent replication. The cloning vector may include plasmid DNA (see Cohen et al., 1973), phage DNA (see Thomas et al., 1974), SV40 DNA (see Nussbaum et al., 1976), yeast DNA, E. coli DNA and most significantly, plant DNA.

A variety of processes are known which may be utilized to effect transformation; i.e., the inserting of a heterologous DNA sequences into a host cell, whereby the host becomes capable of efficient expression of the inserted sequences.

VII. Definitions

By "transformation" or "transfection" is meant the acquisition in cells of new DNA sequences through incorporation of added DNA. This is the process by which naked DNA, DNA coated with protein, or whole artificial chromosomes are introduced into a cell, resulting in a heritable change.

By "gene" is meant a DNA sequence that contains information for construction of a polypeptide or protein, and includes 5' and 3' ends. This also includes genes which encode only RNA products such as tRNA or rRNA genes.

As used herein, "eukaryote" refers to living organisms whose cells contain nuclei. A eukaryote may be distinguished from a "prokaryote" which is an organism which lacks nuclei. Prokaryotes and eukaryotes differ fundamentally in the way their genetic information is organized, as well as their patterns of RNA and protein synthesis.

By the term "lower eukaryote" is meant a eukaryote characterized by a comparatively simple physiology and composition, and most often unicellularity. Examples of lower eukaryotes include flagellates, ciliates, and yeast.

By contrast, the term "higher eukaryote" means a multicellular eukaryote, typically characterized by its greater complex physiological mechanisms and relatively large size. Generally, complex organisms such as plants and animals are included in this category. Preferred higher eukaryotes to be transformed by the present invention include, for example, monocot and dicot angiosperm species, gymnosperm species, fern species, plant tissue culture cells of these species, animal cells and algal cells. It will of course be understood that prokaryotes and eukaryotes alike may be transformed by the methods of this invention.

As used herein, the term "plant" includes plant cells, plant protoplasts, plant calli, and the like, as well as whole plants regenerated therefrom.

As used herein, "heterologous gene" or "foreign gene" is a structural gene that is foreign, i.e., originating from a donor different from the host or a chemically synthesized gene, and can include a donor of a different species from the host. The heterologous gene codes for a polypeptide or RNA ordinarily not produced by the organism susceptible to transformation by the expression vehicle. Another type of "heterologous gene" is an altered gene from the host itself, or an unaltered gene which is present in one or more extra copies. One example of such an altered gene useful in the present invention is a mutant gene which encodes a herbicide-resistant form of a normally occurring enzyme.

By "host" is meant any organism that is the recipient of a replicable plasmid, or expression vector comprising an artificial chromosome. Ideally, host strains used for cloning experiments should be free of any restriction enzyme activity that might degrade the foreign DNA used. Preferred examples of host cells for cloning, useful in the present invention, are bacteria such as *Escherichia coli, Bacillus subtilis, Pseudomonas, Streptomyces, Salmonella*, and yeast cells such as *S. cerevisiae*. Host cells which can be targeted for expression of an artificial chromosome may be plant cells of any source and specifically include *Arabidopsis*, maize, rice, sugarcane, sorghum, barley, soybeans, tobacco, wheat, tomato, potato, citrus, or any other agronomically or scientifically important species.

By "expression" is meant the process by which a structural gene produces an RNA molecule, typically termed messenger RNA (mRNA). The mRNA is typically, but not always, translated into polypeptide(s).

By "linker" it is meant a DNA molecule, generally up to 50 or 60 nucleotides long and synthesized chemically, or cloned from other vectors. In a preferred embodiment, this fragment contains one, or preferably more than one, restriction enzyme site for a blunt-cutting enzyme and a staggered-cutting enzyme, such as BamHI. One end of the linker fragment is adapted to be ligatable to one end of the linear molecule and the other end is adapted to be ligatable to the other end of the linear molecule.

As used herein, a "library" is a pool of random DNA fragments which are cloned. In principle, any gene can be isolated by screening the library with a specific hybridization probe (see, for example, Young et al., 1977). Each library may contain the DNA of a given organism inserted as discrete restriction enzyme-generated fragments or as randomly sheered fragments into many thousands of plasmid vectors. For purposes of the present invention, *E. coli*, yeast, and *Salmonella* plasmids are particularly useful when the genome inserts come from other organisms.

By "hybridization" is meant the pairing of complementary RNA and DNA strands to produce an RNA-DNA hybrid, or alternatively, the pairing of two DNA single strands from genetically different or the same sources to produce a double stranded DNA molecule.

The term "plasmid" or "cloning vector" as used herein refers to a closed covalently circular extrachromosomal DNA or linear DNA which is able to autonomously replicate in a host cell and which is normally nonessential to the survival of the cell. A wide variety of plasmids and other vectors are known and commonly used in the art (see, for example, Cohen et al., U.S. Pat. No. 4,468,464, which discloses examples of DNA plasmids, and which is specifically incorporated herein by reference).

As used herein, a "probe" is any biochemical reagent (usually tagged in some way for ease of identification), used to identify or isolate a gene, a gene product, a DNA segment or a protein.

By "PLAC" it is meant a plant artificial chromosome of the current invention, as specifically disclosed herein.

A "selectable marker" is a gene whose presence results in a clear phenotype, and most often a growth advantage for cells that contain the marker. This growth advantage may be present under standard conditions, altered conditions such as elevated temperature, or in the presence of certain chemicals such as herbicides or antibiotics. Use of selectable markers is described, for example, in Broach et al. (1979). Examples of selectable markers include the thymidine kinase gene, the cellular adenine-phosphoribosyltransferase gene and the dihydrylfolate reductase gene, hygromycin phosphotransferase genes, the bar gene and neomycin phosphotransferase genes, among others. Preferred selectable markers in the present invention include genes whose expression confer antibiotic or herbicide resistance to the host cell, sufficient to enable the maintenance of a vector within the host cell, and which facilitate the manipulation of the plasmid into new host cells. Of particular interest in the present invention are proteins conferring cellular resistance to ampicillin, chlorarnphenicol, tetracycline, G-418, bialaphos, and glyphosate for example.

By "PLAC-encoded protein" it is meant a polypeptide which is encoded by a sequence of a PLAC of the current invention. This includes those proteins encoded by functional sequences of the PLAC, such as selectable markers, telomeres, etc., as well as those proteins encoded by heterologous genes of the PLAC.

By "PLAC-associated protein" it is meant a protein encoded by a sequence of the PLAC or a protein which is encoded by host DNA and binds with relatively high affinity to the centromeres of the current invention.

VIII. *Arabidopsis thaliana* Centromeric DNA Segments as Hybridization Probes and Primers In addition to their use in the construction of PLACs, the centromeric regions disclosed herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of a centromere of the current invention will find particular utility. Longer contiguous identical or complementary sequences, e.g., those of about 20, 30, 40, 50, 100, 200, 500, 1000, 2000, 5000 bp, etc. including all intermediate lengths and up to and including the full-length sequence of a centromere of the current invention also will be of use in certain embodiments.

The ability of such nucleic acid probes to specifically hybridize to centromeric sequences will enable them to be of use in detecting the presence of similar, partially complementary sequences from other plants or animals. However, other uses are envisioned, including the use of the centromeres for the preparation of mutant species primers, or primers for use in preparing other genetic constructions.

Nucleic acid molecules having sequence regions consisting of contiguous nucleotide stretches of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100 or even of 101–200 nucleotides or so, identical or complementary to DNA sequences of a centromere of the current invention, are particularly contemplated as hybridization probes for use in, e.g., Southern and Northern blotting. Smaller fragments will generally find use in hybridization embodiments, wherein the length of the contiguous complementary region may be varied, such as between about 10–14 and about 100 or 200 nucleotides, but larger contiguous complementarity stretches also may be used, according to the length complementary sequences one wishes to detect.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the centromeres of the current invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating centromeric DNA segments. Detection of DNA segments via hybridization is well-known to those of skill in the art, and the teachings of U.S. Pat. Nos. 4,965,188 and 5,176,995 (each specifically incorporated herein by reference in its entirety) are exemplary of the methods of hybridization analyses. Teachings such as those found in the texts of Maloy et al., 1991; Segal 1976; Prokop 1991; and Kuby 1994, are particularly relevant.

Of course, for some applications, for example, where one desires to prepare mutants employing a mutant primer strand hybridized to an underlying template or where one seeks to isolate centromere function-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature or decreased salt. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

IX. PLAC-Associated Protein Specific Antibody Compositions and Methods of Making In particular embodiments, the inventors contemplate the use of antibodies, either monoclonal or polyclonal which bind to PLAC-associated proteins of the current invention. Such PLAC-associated proteins include proteins which are coded by the sequences of the PLAC, as well as proteins encoded by host DNA that bind to the centromeres of the current invention. It is specifically contemplated that these PLAC-associated protein specific antibodies would allow for the further isolation and characterization of the PLAC-associated proteins. For example, proteins may be isolated which are encoded by the centromeres. Recombinant production of such proteins provides a source of antigen for production of antibodies.

Alternatively, the centromere may be used as a ligand to isolate, using affinity methods, centromere binding proteins. Once isolated, these protein can be used as antigens for the production polyclonal and monoclonal antibodies. A variation on this technique has been demonstrated by Rattner (1991), by cloning of centromere-associated proteins through the use of antibodies which bind in the vicinity of the centromere.

Means for preparing and characterizing antibodies are well known in the art (see, e.g., Antibodies: A Laboratory Manual, Cold Spring Harbor Laboratory, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of antisera is a rabbit, a mouse, a rat, a hamster, a guinea pig or a goat. A rabbit is a preferred choice for production of polyclonal antibodies because of the ease of handling, maintenance and relatively large blood volume.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin also can be used as carriers. Means for conjugating a polypeptide to a carrier protein are well known in the art and include glutaraldehyde, m-maleimido-bencoyl-N-hydroxysuccinimide ester, carbodimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection also may be given. The process of boosting and titering is repeated until a suitable titer is achieved. When a desired level of immunogenicity is obtained, the immunized animal can be bled and the serum isolated and stored, and/or the animal can be used to generate mAbs.

Monoclonal antibodies may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified PLAC-associated protein, polypeptide or peptide. The immunizing composition is administered in a manner effective to stimulate antibody producing cells. Rodents such as mice and rats are preferred animals, however, the use of rabbit, sheep, or frog cells also is possible. The use of rats may provide certain advantages (Goding 1986), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas).

Any one of a number of myeloma cells may be used, as are known to those of skill in the art (Goding 1986; Campbell 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S 194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler et al., 1975; 1976), and those using polyethylene glycol (PEG), such as 37% (v/v) PEG, (Gefter et al., 1977). The use of electrically induced fusion methods also is appropriate (Goding 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mabs in high concentration. The individual cell lines also could be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

X. ELISAs and Immunoprecipitation

ELISAs may be used in conjunction with the invention. Particularly, it is contemplated that ELISAs will find use in assays of PLAC gene expression. In an ELISA assay, proteins or peptides comprising PLAC-encoded protein antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate color or light development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

XI. Western Blots

The compositions of the present invention may find use in immunoblot or western blot analysis. The antibodies of the invention may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the protein moiety are considered to be of particular use in this regard.

XII. DNA Segments

Further aspects of the present invention concern isolated DNA segments and recombinant vectors encoding a functional *Arabidopsis thaliana* centromere and other sequences for the creation and use of recombinant sequences of a PLAC.

The present invention concerns DNA segments, isolatable from *A. thaliana* cells, that are enriched relative to total genomic DNA and are capable of conferring centromere activity to a recombinant molecule when incorporated into the host cell. As used herein, the term centromere activity indicates the ability to confer stable inheritance upon a DNA segment, artificial chromosome or chromosome.

As used herein, the term "DNA segment" refers to a DNA molecule that has been purified from total genomic DNA of a particular species. Therefore, a DNA segment encoding centromere function refers to a DNA segment that contains centromere coding sequences yet is isolated away from, or purified free from, total genomic DNA of *A. thaliana*. Included within the term "DNA segment", are DNA segments and smaller fragments of such segments, and also recombinant vectors, including, for example, plasmids, cosmids, phage, viruses, and the like.

Similarly, a DNA segment comprising an isolated or purified centromeric sequence refers to a DNA segment including centromere coding sequences and, in certain aspects, regulatory sequences, isolated substantially away from other naturally occurring genes, protein encoding sequences, or other DNA sequences. In this respect, the term "gene" is used for simplicity to refer to a functional DNA segment, protein, polypeptide or peptide encoding unit. As will be understood by those in the art, this functional term includes both genomic sequences, cDNA sequences and smaller engineered gene segments that may express, or may be adapted to express, proteins, polypeptides or peptides.

"Isolated substantially away from other coding sequences" means that the sequences of interest, in this case centromere function encoding sequences, are included within the genomic DNA clones provided herein. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode a centromere functional sequence that includes a contiguous sequence from the centromeres of the current invention. In certain other embodiments, the invention concerns isolated DNA segments and recombinant vectors that include within their sequence a contiguous nucleic acid sequence from an *A. thaliana* centromere. Again, DNA segments that exhibit centromere function activity will be most preferred.

The nucleic acid segments of the present invention, regardless of the length of the sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and ue in the intended recombinant DNA protocol.

XIII. Biologicall Functional Equivalents

Modification and changes may be made in the centromeric DNA segments of the current invention and still obtain a functional molecule with desirable characteristics. The following is a discussion based upon changing the nucleic acids of a centromere to create an equivalent, or even an improved, second-generation molecule.

In particular embodiments of the invention, mutated centromeric sequences are contemplated to be useful for increasing the utility of the centromere. It is specifically contemplated that the function of the centromeres of the current invention may be based upon the secondary structure of the DNA sequences of the centromere and/or the proteins which interact with the centromere. By changing the DNA sequence of the centromere, one may alter the affinity of one or more centromere-associated protein(s) for the centromere and/or the secondary structure of the centromeric sequences, thereby changing the activity of the centromere. Alternatively, changes may be made in the centromeres of the invention which do not effect the activity of the centromere. Changes in the centromeric sequences which reduce the size of the DNA segment needed to confer centromere activity are contemplated to be particularly useful in the current invention, as would changes which increased the fidelity with which the centromere was transmitted during mitosis and meiosis.

XIV. Obtaining *A. thaliana* Centromeric DNA from Yeast and Bacterial Clones

The *Arabidopsis* physical map consists primarily of YAC clones between 200 kb and 1 Mb in length, and an overlapping contig map with several anchors to the genetic map is available (Hwang et al., 1991) (http://cbil.humgen.upenn.edu/atgc/ATGCUP.html). To be certain that an entire centromeric region has been cloned, clones or a series of clones, are identified that hybridize to markers on either side of each centromere. These efforts can be complicated by the presence of repetitive DNA in the centromere, as well as by the potential instability of centromere clones. Thus, identification of large YACs with unique sequences that will serve as useful probes simplifies a chromosome walking strategy. Use of BACs may also be advantageous, as data has suggested that YAC clones may sometimes not span centromeres (Willard, 1997).

Blot hybridization allows comparison of the structure of the clones with that of genomic DNA, and thus determines whether the clones have suffered deletions or rearrangements. The centromeric clones identified are useful for hybridization experiments that can be used to determine whether they share common sequences, whether they localize in situ to the cytologically defined centromeric region, and whether they contain repetitive sequences thought to map near *Arabidopsis* centromeres (Richards et al., 1991; Maluszynska et al., 1991).

In a positional cloning approach, one may wish to begin sequencing if the region of interest has been narrowed to a sufficiently small area. The determination of what constitutes a sufficiently small sequence is dependent upon many factors including, but not necessarily limited to, the repetitive DNA content of the region of interest, the size of the region to be sequenced, the ability to obtain higher resolution genetic mapping data, and the relative efficiency of sequencing technology. In many cases, sequencing may be begun when the target region has been narrowed to 40 kB or less. It is estimated that in *Arabidopsis thaliana* 1 cM corresponds to approximately 200 kB (Hwang, 1991; Koormeef, 1987). Such a resolution will on average, be provided by analysis of about 100 tetrads for each centromere, although some centromeres may be mapped with higher resolution due to the fact that each tetrad is simultaneously mapping five centromeres, and thus has five times the usual probability of finding a crossover very close to a locus of interest. Nonetheless, because the amount of DNA per cM can increase in the vicinity of the centromere (Carpenter et al., 1982), examination of additional tetrad progeny and identification of additional genetic markers may be required to achieve the desired degree of genetic linkage.

XV. Transformed Host Cells and Transgenic Plants

Methods and compositions for transforming a bacterium, a yeast cell, a plant cell, or an entire plant with one or more artificial chromosomes are further aspects of this disclosure. A transgenic bacterium, yeast cell, plant cell or plant derived from such a transformation process or the progeny and seeds from such a transgenic plant also are further embodiments of the invention.

Means for transforming bacteria and yeast cells are well known in the art. Typically, means of transformation are similar to those well known means used to transform other bacteria or yeast such as *E. coli* or *Saccharomyces cerevisiae*. Methods for DNA transformation of plant cells include *Agrobacterium*-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known in the art which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by *Agrobacterium* infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham et al., 1973; Zatloukal et al., 1992); (2) physical methods such as microinjection (Capecchi, 1980), electroporation (Wong et al., 1982; Fromm et al., 1985; U.S. Pat. No. 5,384,253) and the gene gun (Johnston et al., 1994; Fynan et al., 1993); (3) viral vectors (Clapp 1993; Lu et al., 1993; Eglitis et al., 1988a; 1988b); and (4) receptor-mediated mechanisms (Curiel et al., 1991; 1992; Wagner et al., 1992).

(i) Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

(ii) Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Cristou et al., 1988) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens also are positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One also may minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

(iii) *Agrobacterium*-Mediated Transfer

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described (Fraley et al., 1985; Rogers et al., 1987). Using conventional transformation vectors, chromosomal integration is required for stable inheritance of the foreign DNA. However, the vector described herein may be used for transformation with or without integration, as the centromere function required for stable inheritance is encoded within the PLAC. In particular embodiments, transformation events in which the PLAC is not chromosomally integrated may be preferred, in that problems with site-specific variations in expression and insertional mutagenesis may be avoided.

The integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987). Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

*Agrobacterium*-mediated transformation of leaf disks and other tissues such as cotyledons and hypocotyls appears to be limited to plants that *Agrobacterium* naturally infects. *Agrobacterium*-mediated transformation is most efficient in dicotyledonous plants. Few monocots appear to be natural hosts for *Agrobacterium*, although transgenic plants have been produced in asparagus and more significantly in maize using *Agrobacterium* vectors as described (Bytebier et al., 1987; U.S. Pat. No. 5,591,616, specifically incorporated herein by reference). Therefore, commercially important cereal grains such as rice, corn, and wheat must usually be transformed using alternative methods. However, as mentioned above, the transformation of asparagus using *Agrobacterium* also can be achieved (see, for example, Bytebier et al., 1987).

A transgenic plant formed using *Agrobacterium* transformation methods typically contains a single gene on one chromosome. Such transgenic plants can be referred to as being hemizygous for the added gene. A more accurate name for such a plant is an independent segregant, because each transformed plant represents a unique T-DNA integration event.

More preferred is a transgenic plant that is homozygous for the added foreign DNA; i.e., a transgenic plant that contains two copies of a transgene, one gene at the same locus on each chromosome of a chromosome pair. A homozygous transgenic plant can be obtained by sexually mating (selfing) an independent segregant transgenic plant that contains a single added transgene, germinating some of the seed produced and analyzing the resulting plants produced for enhanced activity relative to a control (native, non-transgenic) or an independent segregant transgenic plant.

Even more preferred is a plant in which the PLAC has not been chromosomally integrated. Such a plant may be termed 2n+x, where 2n is the diploid number of chromosomes and where x is the number of PLACs. Initially, transformants may be 2n+1, i.e. having 1 additional PLAC. In this case, it may be desirable to self the plant or to cross the plant with another 2n+1 plant to yield a plant which is 2n+2. The 2n+2 plant is preferred in that it is expected to pass the PLAC through meiosis to all its offspring.

It is to be understood that two different transgenic plants also can be mated to produce offspring that contain two independently segregating added, exogenous PLACs. Selfing of appropriate progeny can produce plants that are homozygous for both added, exogenous PLACs that encode a polypeptide of interest. Back-crossing to a parental plant and out-crossing with a non-transgenic plant also are contemplated.

XVI. Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1986; Uchimiya et al., 1986; Callis et al., 1987; Marcotte et al., 1988).

Application of these systems to different plant strains for the purpose of making transgenic plants depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil 1988). In addition, "particle gun" or high-velocity microprojectile technology can be utilized (Vasil 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

XVII. Exogenous Genes for Expression in Plants

One particularly important advance of the present invention is that it provides methods and compositions for expression of exogenous genes in plant cells. Significantly, the current invention allows for the transformation of plant cells with a PLAC comprising a number of exogenous genes. Such genes often will be genes that direct the expression of a particular protein or polypeptide product, but they also may be non-expressible DNA segments, e.g., transposons such as Ds that do not direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The inventors also contemplate that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells often will depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch quantity and quality; oil quantity and quality; protein quality and quantity; amino acid composition; and the like. One may desire to incorporate one or more genes conferring any such desirable trait or traits, such as, for example, a gene or genes encoding herbicide resistance.

In certain embodiments, the present invention contemplates the transformation of a recipient cell with PLACs comprising more than one exogenous gene. As used herein, an "exogenous gene," is a gene not normally found in the host genome in an identical context. By this, it is meant that the gene may be isolated from a different species than that of the host genome, or alternatively, isolated from the host genome but operably linked to one or more regulatory regions which differ from those found in the unaltered, native gene. Two or more exogenous genes also can be supplied in a single transformation event using either distinct transgene-encoding vectors, or using a single vector incorporating two or more gene coding sequences. For example, plasmids bearing the bar and aroA expression units in either convergent, divergent, or colinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired.

(i) Herbicide Resistance

The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine (glyphosate). However, genes are known that encode glyphosate-resistant EPSP synthase enzymes. These genes are particularly contemplated for use in plant transformation. The deh gene encodes the enzyme dalapon dehalogenase and confers resistance to the herbicide dalapon. The bxn gene codes for a specific nitrilase enzyme that converts bronioxynil to a non-herbicidal degradation product.

(ii) Insect Resistance

Potential insect resistance genes that can be introduced include *Bacillus thuringiensis* crystal toxin genes or Bt genes (Watrud et al., 1985). Bt genes may provide resistance to lepidopteran or coleopteran pests such as European Corn Borer (ECB). Preferred Bt toxin genes for use in such embodiments include the CryIA (b) and CryIA(c) genes. Endotoxin genes from other species of *B. thuringiensis* which affect insect growth or development also may be employed in this regard.

It is contemplated that preferred Bt genes for use in the transformation protocols disclosed herein will be those in which the coding sequence has been modified to effect increased expression in plants, and more particularly, in monocot plants. Means for preparing synthetic genes are well known in the art and are disclosed in, for example, U.S. Pat. No. 5,500,365 and U.S. Pat. No. 5,689,052, each of the disclosures of which are specifically incorporated herein by reference in their entirety. Examples of such modified Bt toxin genes include a synthetic Bt CryIA(b) gene (Perlak et al., 1991), and the synthetic CryIA(c) gene termed 1800b (PCT Application WO 95/06128). Some examples of other Bt toxin genes known to those of skill in the art are given in Table 1 below.

TABLE 1

Bacillus thuringiensis δ-Endotoxin Genes[a]

| New Nomenclature | Old Nomenclature | GenBank Accession |
| --- | --- | --- |
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |
| Cry1Ba | CryIB | X06711 |
| Cry1Bb | ET5 | L32020 |
| Cry1Bc | PEG5 | Z46442 |
| Cry1Bd | CryE1 | U70726 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1Ga | PrtA | Z22510 |
| Cry1Gb | CryH2 | U70725 |
| Cry1Ha | PrtC | Z22513 |
| Cry1Hb |  | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K |  | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |
| Cry11A | CryIVD | M31737 |
| Cry11B | Jeg80 | X86902 |
| Cry12A | CryVB | L07027 |
| Cry13A | CryVC | L07023 |
| Cry14A | CryVD | U13955 |
| Cry15A | 34kDa | M76442 |
| Cry16A | cbm71 | X94146 |
| Cry17A | cbm71 | X99478 |
| Cry18A | CryBP1 | X99049 |
| Cry19A | Jeg65 | Y08920 |
| Cyt1Aa | CytA | X03182 |
| Cyt1Ab | CytM | X98793 |
| Cyt2A | CytB | Z14147 |
| Cyt2B | CytB | U52043 |

[a]Adapted from: http://epunix.biols.susx.ac.uk/Home/Neil_Crickmore/Bt/index.html Protease inhibitors also may provide insect resistance (Johnson et al., 1989), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered to produce synergistic insecticidal activity. Other genes which encode inhibitors of the insect's digestive system, or those that encode enzymes or co-factors that facilitate the production of inhibitors, also may be useful. This group may be exemplified by oryzacystatin and amylase inhibitors such as those from wheat and barley.

Also, genes encoding lectins may confer additional or alternative insecticide properties. Lectins (originally termed phytohemagglutinins) are multivalent carbohydrate-binding proteins which have the ability to agglutinate red blood cells from a range of species. Lectins have been identified recently as insecticidal agents with activity against weevils, ECB and rootworm (Murdock et al., 1990; Czapla & Lang, 1990). Lectin genes contemplated to be useful include, for example, barley and wheat germ agglutinin (WGA) and rice lectins (Gatehouse et al., 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, also may result in insecticidal activity, or perhaps cause cessation of metamorphosis (Hammock et al., 1990).

Transgenic plants expressing genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant plants. Genes that code for activities that affect insect molting, such as those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests also are encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson and Guss, 1972). It is further anticipated that other cereal, monocot or dicot plant species may have genes encoding proteins that are toxic to insects which would be useful for producing insect resistant plants.

Further genes encoding proteins characterized as having potential insecticidal activity also may be used as transgenes in accordance herewith. Such genes include, for example, the cowpea trypsin inhibitor (CpTI; Hilder et al., 1987) which may be used as a rootworm deterrent; genes encoding avermectin (*Avermectin and Abamectin*, Campbell, W. C., Ed., 1989; Ikeda et al, 1987) which may prove particularly useful as a corn rootworm deterrent; ribosome inactivating protein genes; and even genes that regulate plant structures. Transgenic plants including anti-insect antibody genes and genes that code for enzymes that can convert a non-toxic insecticide (pro-insecticide) applied to the outside of the plant into an insecticide inside the plant also are contemplated.

(iii) Environment or Stress Resistance

Improvement of a plants ability to tolerate various environmental stresses such as, but not limited to, drought, excess moisture, chilling, freezing, high temperature, salt, and oxidative stress, also can be effected through expression of novel genes. It is proposed that benefits may be realized in terms of increased resistance to freezing temperatures through the introduction of an "antifreeze" protein such as that of the Winter Flounder (Cutler et al, 1989) or synthetic gene derivatives thereof. Improved chilling tolerance also may be conferred through increased expression of glycerol-3-phosphate acetyltransferase in chloroplasts (Wolter et al, 1992). Resistance to oxidative stress (often exacerbated by conditions such as chilling temperatures in combination with high light intensities) can be conferred by expression of superoxide dismutase (Gupta et al, 1993), and may be improved by glutathione reductase (Bowler et al, 1992). Such strategies may allow for tolerance to freezing in newly emerged fields as well as extending later maturity higher yielding varieties to earlier relative maturity zones.

It is contemplated that the expression of novel genes that favorably effect plant water content, total water potential, osmotic potential, and turgor will enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments. In this aspect of the invention it is proposed, for example, that the expression of genes encoding for the biosynthesis of osmotically-active solutes, such as polyol compounds, may impart protection against drought. Within this class are genes encoding for mannitol-L-phosphate dehydrogenase (Lee and Saier, 1982) and trehalose-6-phosphate synthase (Kaasen et al., 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., 1992, 1993).

Similarly, the efficacy of other metabolites in protecting either enzyme function (e.g., alanopine or propionic acid) or membrane integrity (e.g., alanopine) has been documented (Loomis et al., 1989), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol (Coxson et al., 1992), sorbitol, dulcitol (Karsten et al., 1992), glucosylglycerol (Reed et al., 1984; ErdMann et al., 1992), sucrose, stachyose (Koster and Leopold, 1988; Blackman et al., 1992), raffinose (Bernal-Lugo and Leopold, 1992), proline (Rensburg et al., 1993), glycine betaine, ononitol and pinitol (Vernon and Bohnert, 1992). Continued canopy growth and increased reproductive fitness during times of stress will be augmented by introduction and expression of genes such as those controlling the osmotically active compounds discussed above and other such compounds. Currently preferred genes which promote the synthesis of an osmotically active polyol compound are genes which encode the enzymes mannitol-1-phosphate dehydrogenase, trehalose-6-phosphate synthase and myo-inositol O-methyltransferase.

It is contemplated that the expression of specific proteins also may increase drought tolerance. Three classes of Late Embryogenic Proteins have been assigned based on structural similarities (see Dure et al., 1989). All three classes of LEAs have been demonstrated in maturing (i.e. desiccating) seeds. Within these 3 types of LEA proteins, the Type-II (dehydrin-type) have generally been implicated in drought and/or desiccation tolerance in vegetative plant parts (i.e. Mundy and Chua, 1988; Piatkowski et al., 1990; Yamaguchi-Shinozaki et al., 1992). Recently, expression of a Type-III LEA (HVA-1) in tobacco was found to influence plant height, maturity and drought tolerance (Fitzpatrick, 1993). In rice, expression of the HVA-1 gene influenced tolerance to water deficit and salinity (Xu et al., 1996). Expression of structural genes from all three LEA groups may therefore confer drought tolerance. Other types of proteins induced during water stress include thiol proteases, aldolases and transmembrane transporters (Guerrero et al., 1990), which may confer various protective and/or repair-type functions during drought stress. It also is contemplated that genes that effect lipid biosynthesis and hence membrane composition might also be useful in conferring drought resistance on the plant.

Many of these genes for improving drought resistance have complementary modes of action. Thus, it is envisaged that combinations of these genes might have additive and/or synergistic effects in improving drought resistance in plants. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor-induced promoter (such as the promoters for the turgor-induced genes described in Guerrero et al., 1990 and Shagan et al., 1993 which are incorporated herein by reference). Spatial and temporal expression patterns of these genes may enable plants to better withstand stress.

It is proposed that expression of genes that are involved with specific morphological traits that allow for increased water extractions from drying soil would be of benefit. For example, introduction and expression of genes that alter root characteristics may enhance water uptake. It also is contemplated that expression of genes that enhance reproductive fitness during times of stress would be of significant value. For example, expression of genes that improve the synchrony of pollen shed and receptiveness of the female flower parts, i.e., silks, would be of benefit. In addition it is proposed that expression of genes that minimize kernel abortion during times of stress would increase the amount of grain to be harvested and hence be of value.

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

(iv) Disease Resistance

It is proposed that increased resistance to diseases may be realized through introduction of genes into plants, for example, into monocotyledonous plants such as maize. It is possible to produce resistance to diseases caused by viruses, bacteria, fungi and nematodes. It also is contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo et al., 1988, Hemenway et al., 1988, Abel et al., 1986). It is contemplated that expression of antisense genes targeted at essential viral functions may also impart resistance to viruses. For example, an antisense gene targeted at the gene responsible for replication of viral nucleic acid may inhibit replication and lead to resistance to the virus. It is believed that interference with other viral functions through the use of antisense genes also may increase resistance to viruses. Further, it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in monocotyledonous plants such as maize may be useful in conferring resistance to bacterial disease. These genes are induced following pathogen attack on a host plant and have been divided into at least five classes of proteins (Bol, Linthorst, and Cornelissen, 1990). Included amongst the PR proteins are $\beta$-1, 3-glucanases, chitinases, and osmotin and other proteins that are believed to function in plant resistance to disease organisms. Other genes have been identified that have antifungal properties, e.g., UDA (stinging nettle lectin) and hevein (Broakaert et al., 1989; Barkai-Golan et al., 1978). It is known that certain plant diseases are caused by the production of phytotoxins. It is proposed that resistance to these diseases would be achieved through expression of a novel gene that encodes an enzyme capable of degrading or otherwise inactivating the phytotoxin. It also is contemplated that expression of novel genes that alter the interactions between the host plant and pathogen may be useful in reducing the ability of the disease organism to invade the tissues of the host plant, e.g., an increase in the waxiness of the leaf cuticle or other morphological characteristics.

(v) Plant Agronomic Characteristics

Two of the factors determining where crop plants can be grown are the average daily temperature during the growing season and the length of time between frosts. Within the areas where it is possible to grow a particular crop, there are varying limitations on the maximal time it is allowed to grow to maturity and be harvested. For example, a variety to be grown in a particular area is selected for its ability to mature and dry down to harvestable moisture content within the required period of time with maximum possible yield. Therefore, crops of varying maturities is developed for different growing locations. Apart from the need to dry down sufficiently to permit harvest, it is desirable to have maximal drying take place in the field to minimize the amount of energy required for additional drying post-harvest. Also, the more readily a product such as grain can dry down, the more time there is available for growth and kernel fill. It is considered that genes that influence maturity and/or dry down can be identified and introduced into plant lines using transformation techniques to create new varieties adapted to different growing locations or the same growing location, but having improved yield to moisture ratio at harvest. Expression of genes that are involved in regulation of plant development may be especially useful.

It is contemplated that genes may be introduced into plants that would improve standability and other plant growth characteristics. Expression of novel genes in plants which confer stronger stalks, improved root systems, or prevent or reduce ear droppage would be of great value to the farmer. It is proposed that introduction and expression of genes that increase the total amount of photoassimilate available by, for example, increasing light distribution and/or interception would be advantageous. In addition, the expression of genes that increase the efficiency of photosynthesis and/or the leaf canopy would further increase gains in productivity. It is contemplated that expression of a phytochrome gene in crop plants may be advantageous. Expression of such a gene may reduce apical dominance, confer semidwarfism on a plant, and increase shade tolerance (U.S. Pat. No. 5,268,526). Such approaches would allow for increased plant populations in the field.

(vi) Nutrient Utilization

The ability to utilize available nutrients may be a limiting factor in growth of crop plants. It is proposed that it would be possible to alter nutrient uptake, tolerate pH extremes, mobilization through the plant, storage pools, and availability for metabolic activities by the introduction of novel genes. These modifications would allow a plant such as maize to more efficiently utilize available nutrients. It is contemplated that an increase in the activity of, for example, an enzyme that is normally present in the plant and involved in nutrient utilization would increase the availability of a nutrient. An example of such an enzyme would be phytase. It is further contemplated that enhanced nitrogen utilization by a plant is desirable. Expression of a glutamate dehydrogenase gene in plants, e.g., *E. coli* gdhA genes, may lead to increased fixation of nitrogen in organic compounds. Furthermore, expression of gdhA in plants may lead to enhanced resistance to the herbicide glufosinate by incorporation of excess ammonia into glutamate, thereby detoxifying the ammonia. It also is contemplated that expression of a novel gene may make a nutrient source available that was previously not accessible, e.g., an enzyme that releases a component of nutrient value from a more complex molecule, perhaps a macromolecule.

(vii) Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani et al., 1990).

A number of mutations were discovered in maize that confer cytoplasmic male sterility. One mutation in particular, referred to as T cytoplasm, also correlates with sensitivity to Southern corn leaf blight. A DNA sequence, designated TURF-13 (Levings, 1990), was identified that correlates with T cytoplasm. It is proposed that it would be possible through the introduction of TURF-13 via transformation, to separate male sterility from disease sensitivity. As it is necessary to be able to restore male fertility for breeding purposes and for grain production, it is proposed that genes encoding restoration of male fertility also may be introduced.

(viii) Negative Selectable Markers

Introduction of genes encoding traits that can be selected against may be useful for eliminating PLACs from a cell or for selecting against cells which comprise a particular PLAC. An example of a negative selectable marker which has been investigated is the enzyme cytosine deaminase (Stouggard, 1993). In the presence of this enzyme the compound 5-fluorocytosine is converted to 5-fluorouracil which is toxic to plant and animal cells. Therefore, cells comprising a PLAC with this gene could be directly selected against. Other genes that encode proteins that render the plant sensitive to a certain compound will also be useful in this context. For example, T-DNA gene 2 from *Agrobacterium tumefaciens* encodes a protein that catalyzes the conversion of α-naphthalene acetamide (NAM) to α-naphthalene acetic acid (NAA) renders plant cells sensitive to high concentrations of NAM (Depicker et al., 1988).

(ix) Non-Protein-Expressing Sequences

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes. However, as detailed below, DNA need not be expressed to effect the phenotype of a plant.

1. Antisense RNA

Genes may be constructed or isolated, which when transcribed, produce antisense RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

2. Ribozymes

Genes also may be constructed or isolated, which when transcribed, produce RNA enzymes (ribozymes) which can act as endoribonucleases and catalyze the cleavage of RNA molecules with selected sequences. The cleavage of selected messenger RNAs can result in the reduced production of their encoded polypeptide products. These genes may be used to prepare novel transgenic plants which possess them. The transgenic plants may possess reduced levels of polypeptides including, but not limited to, the polypeptides cited above.

Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoester in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes.

Several different ribozyme motifs have been described with RNA cleavage activity (Symons, 1992). Examples include sequences from the Group I self splicing introns including Tobacco Ringspot Virus (Prody et al., 1986), Avocado Sunblotch Viroid (Palukaitis et al., 1979; Symons, 1981), and Lucerne Transient Streak Virus (Forster and Symons, 1987). Sequences from these and related viruses are referred to as hammerhead ribozyme based on a predicted folded secondary structure.

Other suitable ribozymes include sequences from RNase P with RNA cleavage activity (Yuan et al., 1992, Yuan and Altman, 1994, U.S. Pat. Nos. 5,168,053 and 5,624,824), hairpin ribozyme structures (Berzal-Herranz et al., 1992; Chowrira et al., 1993) and Hepatitis Delta virus based ribozymes (U.S. Pat. No. 5,625,047). The general design and optimization of ribozyme directed RNA cleavage activity has been discussed in detail (Haseloff and Gerlach, 1988, Symons, 1992, Chowrira et al., 1994; Thompson et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A,C or U) (Perriman et al., 1992; Thompson et al., 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in down regulating a given gene is simply a matter of preparing and testing a given sequence, and is a routinely practiced "screening" method known to those of skill in the art.

3. Induction of Gene Silencing

It also is possible that genes may be introduced to produce novel transgenic plants which have reduced expression of a native gene product by the mechanism of co-suppression. It has been demonstrated in tobacco, tomato, and petunia (Goring et al., 1991; Smith et al., 1990; Napoli et al., 1990; van der Krol et al., 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

4. Non-RNA-Expressing Sequences

DNA elements including those of transposable elements such as Ds, Ac, or Mu, may be inserted into a gene to cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta et al., 1988). Once identified, the entire gene(s) for the particular trait, including control or regulatory regions where desired, may be isolated, cloned and manipulated as desired. The utility of DNA elements introduced into an organism for purposes of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences, could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary gerrnplasm or germplasm derived from such, from unlabelled germplasm.

Another possible element which may be introduced is a matrix attachment region element (MAR), such as the chicken lysozyme A element (Stief, 1989), which can be positioned around an expressible gene of interest to effect an increase in overall expression of the gene and diminish position dependent effects upon incorporation into the plant genome (Stief et al., 1989; Phi-Van et al., 1990).

XVIII. EXAMPLES

The following examples are included to demonstrate preferred embodiments of the invention. It should be appreciated by those of skilled the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Generation of an *Arabidopsis thaliana* Mapping Population

To generate a pollen donor plant, two alleles of qrtl were crossed to one another. The qrtl-1 allele was in the Landsberg ecotype background and the qrtl-2 allele was in the Columbia ecotype background. The Landsberg ecotype was readily discernible from the Columbia ecotype because it carries a recessive mutation, erecta, which causes the stems to thicken, infloresences to be more compact, and the leaves to be more rounded and small than wildtype. To utilize this as a marker of a donor plant, qrtl-2 pollen was crossed onto a qrtl-1 female stigma. The $F_1$ progeny were heterozygous at all molecular markers yet the progeny retain the quartet phenotype of a tetrad of fused pollen grains. In addition, progeny display the ERECTA phenotype of the Columbia plant. This visible marker serves as an indication that the crossing was successful in generating plants segregating ecotype specific markers. Further testing was done to the donor plants by performing PCR analysis to insure that progeny were heterozygous at molecular loci.

Due to the fact that the pollen grains can not be directly assayed for marker segregation and because of the desire to create a long-term resource available for multiple marker assays, it was necessary to cross individual tetrads generated by the donor plant. This created sets of progeny plants which yielded both large quantities of tissue and seed. These crosses were accomplished efficiently by generating a recipient plant homozygous for glaborous 1-1 and male sterility. The recessive visible mutant, glaborous 1-1, was chosen to guard against the possibility of the recipient plant self-fertilizing and the progeny being mistaken for tetrad plants. Pollen inviability through male sterile-1 was introduced to guard against the recipient plant self-fertilizing. Due to the fact that the homozygous plant does not self, a stock seed generated by a heterozygous male sterility I plant needs to be maintained from which sterile recipient plants can be selected. A large resource of seed segregating the optimal sterile and visually marked recipient plant was obtained.

Example 2

Tetrad Pollinations

Tetrad pollinations were carried out as follows. A mature flower was removed from the donor plant and tapped upon a glass microscope slide to release mature tetrad pollen grains. This slide was then placed under a 20–40× Zeiss dissecting microscope. To isolate individual tetrad pollen grains, a small wooden dowel was used to which an eyebrow hair with rubber cement was mounted. Using the light microscope, a tetrad pollen unit was chosen and touched to the eyebrow hair. The tetrad preferentially adhered to the eyebrow hair and was thus lifted from the microscope slide and transported the recipient plant stigmatic surface. The transfer was carried out without the use of the microscope, and the eyebrow hair with adhering tetrad was then placed against the recipient stigmatic surface and the hair was manually dragged across the stigma surface. The tetrad then preferentially adhered to the stigma of the recipient and the cross pollination was completed.

Preferably, an additional backcross of the qrtl-2 parent was used to increase the pollination efficiency, which was increased to >80% successful seed set production. Initially, 57 tetrad seed sets consisting of 34 seeds each, were collected. Plants were grown from these tetrad seed sets, and tissue was collected. DNA was extracted from a small portion of the stored tissue for PCR based segregation analysis. Additionally the segregation of the visible erecta phenotype was scored. When the plants set seed, the seed was collected as a source for the larger amounts of DNA required to analyze RFLP segregation by Southern blotting.

Example 3

Genetic Mapping of Centromeres

To map centromeres, $F_1$ plants which were heterozygous for hundreds of polymorphic DNA markers were generated by crossing quartet mutants from the Landsberg and Columbia ecotypes (Chang et al. 1988; Ecker, 1994; Konieczy and Ausubel, 1993). In tetrads from these plants, genetic markers segregate in a 2:2 ratio (FIG. 6; Preuss et al. 1994). The segregation of markers was then determined in plants which were generated by crossing pollen grains from the $F_1$ plants onto a Landsberg homozygote. The genotype of the pollen grains within a tetrad was inferred from the genotype of the progeny. Initially, seeds were generated from greater than 100 successful tetrad pollinations, and tissue and seeds were collected from 57 of these. This provided sufficient material for PCR, as well as seeds necessary for producing the large quantities of tissue required for Southern hybridization and RFLP mapping. In order to obtain a more precise localization of the centromeres the original tetrad population was increased from 57 tetrads to over 388 tetrads. Additional tetrads may be collected to provide even better resolution.

PCR analysis was performed to determine marker segregation. To account for the contribution of the Landsberg background from the female parent, one Landsberg complement from each of the four tetrad plants was subtracted. As shown in FIG. 5, markers from sites spanning the entire genome were used for pair-wise comparisons of all other markers. Tetratypes indicate a crossover between one or both markers and their centromeres where as ditypes indicate the absence of crossovers (or presence of a double crossover).

Thus, at every genetic locus, the resulting diploid progeny was either L/C or C/C. The map generated with these plants is based solely on male meioses, unlike the existing map, which represents an average of recombination's in both males and females. Therefore, several well-established genetic distances were recalculated and thus will determine whether recombination frequencies are significantly altered.

The large quantities of genetic data generated by the analysis must be compared pair-wise to perform tetrad analysis. All of the data was managed in a Microsoft Excel spread-sheet format, assigning Landsberg alleles a value of "1" and Columbia alleles a value of "0". Within a tetrad, the segregation of markers on one chromosome was compared to centromere-linked reference loci on a different chromosome (see Table 2 below). Multiplying the values of each locus by an appropriate reference, and adding the results for each tetrad easily distinguished PD, NPD, and TT tetrads with values of 2, 0, and 1, respectively. By scoring more than 53 PCR-based genetic markers distributed across the genome, all five *Arabidopsis thaliana* centromeres were mapped to small intervals (FIGS. 3A–3E). Additionally, for each centromeric interval, a number of useful recombinants were identified.

TABLE 2

Scoring protocol for tetratypes.

| Individual members of a tetrad | Locus 1 | Reference Locus | Locus 2 | Reference Locus | Locus 3 | Reference Locus |
|---|---|---|---|---|---|---|
| A | 1 | × 1 = 1 | 0 | × 1 = 0 | 0 | × 1 = 0 |
| B | 1 | × 1 = 1 | 0 | × 1 = 0 | 1 | × 1 = 1 |
| C | 0 | × 0 = 0 | 1 | × 0 = 0 | 0 | × 0 = 0 |
| D | 0 | × 0 = 0 | 1 | × 0 = 0 | 1 | × 0 = 0 |
| — | | 2 PD | | 0 NPD | | 1 TT |

Example 4

Mapping Results: *Arabidopsis* Chromosomes 1–5

The centromere on chromosome 1 was mapped between mi342 (56.7 cM) and T27K12 (59.1 cM). A more refined position places the centromere between the marker T22C23 (~58.5 cM) and T27K12 (59.1 cM). However, since T22C23 is not precisely mapped the centromere may be between the publicly available markers mi342 and T27K12.

The centromere on chromosome 2 was mapped between mi310 (18.6 cM) and g4133 (23.8 cM). Within this interval the centromere may be between the following publicly available marker pairs: mi310 and mi421, mi421 and g4532, g4532 and SEP2A, and SEP2A and g4133.

The centromere on chromosome 3 was mapped between atpox (48.6 cM) and ve021 (54.7 cM). A more refined position places the centromere between the marker atpox (48.6 cM) and 91F1T7 (~54.2 cM) however, since 91F1T7 is not precisely mapped, the centromere may be between the following publicly available marker pairs: atpox and zim2, zim2 and mi79b, mi79b and RCEN3, RCEN3 and ASD, ASD and a-1, a-1 and t04109, and t04109 and ve021.

The centromere on chromosome 4 was mapped between mi233 (18.8 cM) and mi167 (21.5 cM). A more refined position places the centromere between the markers mi233 and F13H14 however since F13H14 is not precisely mapped, the centromere may be between the following publicly available marker pairs: mi233 and g2616, g2616 and mi306, mi306 and m506, m506 and nga12, nga12 and B10200, B10200 and mi87, mi87 and C11Ath, C11Ath and m456A, and m456A and mi 167.

The centromere on chromosome 5 was mapped between nga76 (71.6 cM) and PhC (74.3 cM). Within this interval the centromere may be between the following publicly available marker pairs: nga76 and mi291b, mi291b and CMs1, and CMs1 and PhyC.

All of the above markers and genetic positions (i.e. cM values) correspond to the Lister and Dean Recombinant Inbred Genetic map, available on-line at: http://genome-www3.stanford.edu/atdb_welcome.html.

Example 5

Construction of Artificial Plant Chromosomes

Plant artificial chromosomes are constructed by combining the previously isolated essential chromosomal elements. Exemplary artificial chromosomes include those designed to be "shuttle vectors"; i.e., they can be maintained in a convenient host (such as *E. coli, Agrobacterium* or yeast) as well as plant cells.

An artificial chromosome can be maintained in *E coli* or other bacterial cells as a circular molecule by placing a removable stuffer fragment between the telomeric sequence blocks. The stuffer fragment is a dispensable DNA sequence, bordered by unique restriction sites, which can be removed by restriction digestion of the circular DNAs to create linear molecules with telomeric ends. The linear PLAC can then be isolated by, for example, gel electrophoresis. In addition to the stuffer fragment and the plant telomeres, the artificial chromosome contains a replication origin and selectable marker that can function in plants to allow the circular molecules to be maintained in bacterial cells. The artificial chromosomes also include a plant selectable marker, a plant centromere, and a plant ARS to allow replication and maintenance of the DNA molecules in plant cells. Finally, the artificial chromosome includes several unique restriction sites where additional DNA sequence inserts can be cloned. The most expeditious method of physically constructing such an artificial chromosome, ie., ligating the various essential elements together for example, will be apparent to those of ordinary skill in this art.

A number of artificial chromosome vectors have been designed by the current inventors and are disclosed herein for the purpose of illustration (FIGS. 7A–7H). These vectors are not limiting however, as it will be apparent to those of skill in the art that many changes and alterations may be made and still obtain a functional vector.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abdullah et al., *Biotechnology*, 4:1087, 1986.
Abel et al., *Science*, 232:738–743, 1986.
Alfenito et al., "Molecular characterization of a maize B chromosome centric sequence," *Genetics*, 135:589–597, 1993.
Barkai-Golan et al., *Arch. Microbiol.*, 116:119–124, 1978.
Baum et al., "The centromeric K-type repeat and the central core are together sufficient to establish a functional *Schizosaccharomyces pombe* centromere," Mol. *Bio. Cell.*, 5:747–761, 1994.
Bell et al., "Assignment of 30 microsatellite loci to the linkage map of *Arabidopsis*," *Genomics*, 19:137–144, 1994.
Bernal-Lugo and Leopold, *Plant Physiol*, 98:1207–1210, 1992.
Berzal-Herranz et al., *Genes and Devel.*, 6:129–134, 1992.
Blackman et al., *Plant Physiol.*, 100:225–230, 1992.
Bloom, "The centromere frontier: Kinetochore components, microtubule-based motility, and the CEN-value paradox," *Cell*, 73:621–624, 1993.
Bol et al., *Annu. Rev. Phytopath.*, 28:113–138, 1990.
Bowler et al., *Ann Rev. Plant Physiol.*, 43:83–116, 1992.
Branson and Guss, *Proceedings North Central Branch Entomological Society of America*, 27:91–95, 1972.
Brisson et al., *Nature*, 310:511, 1984.
Broach et al., *Gene*, 8:121–133, 1979.
Broakaert et al., *Science*, 245:1100–1102, 1989.
Burke et al., *Science*, 236:806–812, 1987.
Bytebier et al, *Proc. Natl. Acad. Sci. USA*, 84:5345, 1987.
Callis et al., *Genes and Development*, 1:1183, 1987.
Campbell (ed.), *In: Avermectin and Abamectin*, 1989.
Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.
Capecchi, "High efficiency transformation by direct microinjection of DNA into cultured mammalian cells," *Cell* 22(2):479–488, 1980.
Carbon et al, *In: Recombinant Molecules: Impact on Science and Society* (Raven Press), 335–378, 1977.
Carbon et al., "Centromere structure and function in budding and fission yeasts," *New Biologist*, 2:10–19, 1990.
Carpenter et al., "The control of the distribution of meiotic exchange in Drosophilla melanogaster," *Genetics*, 101:81–90, 1982.
Cech et al., "In vitro splicing of the ribosomal RNA precursor of Tetrahymena: involvement of a guanosine nucleotide in the excision of the intervening sequence," *Cell*, 27:487496, 1981.
Chang et al., "Restriction fragment length polymorphism linkage map for *Arabidopsis thaliana*," Proc. Nat'l Acad. Sci., USA, 85:6856–6860, 1988.
Chepko, *Cell*, 37:1053, 1984.
Chowrira et al., "In vitro and in vivo comparison of hammerhead, hairpin, and hepatitis delta virus self-processing ribozyme cassetyes," *J. Biol. Chem.*, 269:25856–25864, 1994.
Chu et al., "Separation of large DNA molecules by contour-clamped homogeneous electric fields" *Science*, 234, 1582–1585, 1986.
Clapp, "Somatic gene therapy into hematopoietic cells. Current status and future implications," *Clin. Perinatol.* 20(1): 155–168, 1993.
Clarke et al., "Isolation of a yeast centromere and construction of functional small circular chromosomes," *Nature*, 287:504–509, 1980.
Cohen et al., *Proc. Nat'l Acad. Sci. USA*, 70:3240, 1973.

Copenhaver et al., "Use of RFLPs larger than 100 kbp to map position and internal organization of the nucleolus organizer region on chromosome 2 in *Arabidopsis thaliana*," Plant J. 7, 273–286, 1995.
Coxson et al., *Biotropica*, 24:121–133, 1992.
Cristou et al., *Plant Physiol*, 87:671–674, 1988.
Cuozzo et al., *Bio/Technology*, 6:549–553, 1988.
Curiel et al., "Adenovirus enhancement of transferrin-polylysine-mediated gene delivery," *Proc. Nat'l Acad. Sci. USA* 88(19):8850–8854, 1991.
Curiel et al., high-efficiency gene transfer mediated by adenovirus coupled to DNA-polylysine complexes," *Hum. Gen. Ther.* 3(2):147–154, 1992.
Cutler et al., *J. Plant Physiol.*, 135:351–354, 1989.
Czapla and Lang, *J. Econ. Entomol.*, 83:2480–2485, 1990.
Davies et al., *Plant Physiol.*, 93:588–595, 1990.
Dellaporta et al., *In: Chromosome Structure and Function: Impact of New Concepts, 18th Stadler Genetics Symposium*, 11:263–282, 1988.
Depicker et al., *Plant Cell Reports*, 7:63–66, 1988.
Dillon et al., *Recombinant DNA Methodology*, 1985.
Dure et al., *Plant Molecular Biology*, 12:475–486, 1989.
Earnshaw et al., "Proteins of the inner and outer centromere of mitotic chromosomes," *Genome*, 31:541–552, 1989.
Earnshaw, "When is a centromere not a kinetochore?," *J. Cell Sci.*, 99:14, 1991.
Ecker, J R, Genomics, 19:137–144
Eglitis et al., "Retroviral vectors for introduction of genes into mammalian cells," *Biotechniques* 6(7):608–614, 1988.
Eglitis et al., "Retroviral-mediated gene transfer into hemopoietic cells," *Avd. Exp. Med. Biol.* 241:19–27, 1988.
Erdmann et al., *J. Gen. Microbiology*, 138:363–368, 1992.
Fitzpatrick, *Gen. Engineering News*, 22:7, 1993.
Forster and Symons, "Self-cleavage of plus and minus RNAs of a virusoid and a structural model for the active sites," *Cell*, 49:211–220, 1987.
Fraley et al., *Biotechnology*, 3:629, 1985.
Fromm et al., "Expression of genes transferred into monocot and dicot plant cells by electroporation," *Proc. Nat'l Acad. Sci. USA* 82(17):5824–5828, 1985.
Fromm M. E., Taylor L. P., Walbot V. (1986). *Nature* 312:791–793.
Fujimura et al., *Plant Tissue Culture Letters*, 2:74, 1985.
Fynan et al., "DNA vaccines: protective immunizations by parenteral, mucosal, and gene gun inoculations," *Proc. Nat'l Acad. Sci. USA* 90(24): 11478–11482, 1993.
Gatehouse et al., *J. Sci. Food. Agric.*, 35:373–380, 1984.
Gefter et al., *Somatic Cell Genet.* 3:231–236, 1977.
Gerlach et al., "Construction of a plant disease resistance gene from the satellite RNA of tobacco rinspot virus," *Nature* (London), 328:802–805, 1987.
Goding, "Monoclonal Antibodies: Principles and Practice," pp. 60–74. 2nd Edition, Academic Press, Orlando, Fla., 1986.
Goring et al., *Proc. Natl. Acad. Sci. USA*, 88:1770–1774, 1991.
Graham et al., "Transformation of rat cells by DNA of human adenovirus 5," *Virology* 54(2):536–539, 1973.
Guerrero et al., *Plant Molecular Biology*, 15:11–26, 1990.
Gupta et al., *Proc. Natl. Acad. Sci. USA*, 90:1629–1633, 1993.
Haaf et al., "Integration of human α-satellite DNA into simian chromosomes: centromere protein binding and disruption of normal chromosome segregation," *Cell*, 70:681–696, 1992.

Hadlaczky et al., "Centromere formation in mouse cells cotransformed with human DNA and a dominant marker gene," *Proc. Natl. Acad. Sci. USA*, 88:8106–8110, 1991.

Hammock et al., *Nature*, 344:458461, 1990.

Hegemann et al., "The centromere of budding yeast," *Bioassays*, 15(7):451–460, 1993.

Hemenway et al., *The EMBO J*, 7:1273–1280, 1988.

Hilder et al., *Nature*, 330:160–163, 1987.

Hsiao et al., *J. Proc. Nat'l Acad. Sci. USA*, 76:3829–3833, 1979.

Hwang et al., "Identification and map position of YAC clones comprising one-third of the *Arabidopsis* genome, *The Plant Journal*, 1:367–374, 1991.

Ikeda et al, *J. Bacteriol.*, 169:5615–5621, 1987.

Johnston et al, "Gene gun transfection of animal cells and genetic immunization," *Methods Cell. Biol.* 43(A): 353–365, 1994.

Jones, *Embo J.*, 4:2411–2418, 1985.

Jones, *Mol Gen. Genet.*, 207:478, 1987.

Jorgensen et al., *Mol. Gen. Genet.*, 207:471, 1987.

Joyce, "RNA evolution and the origins of life," *Nature*, 338:217–244, 1989.

Kaasen et al., *J. Bacteriology*, 174:889–898, 1992.

Karsten et al, *Botanica Marina*, 35:11–19, 1992.

Kim and Cech, "Three dimensional model of the active site of the self-splicing rRNA precursor of Tetrahymena," *Proc. Natl. Acad. Sci. USA*, 84:8788–8792, 1987.

Klee et al., *Bio/Technology* 3:637–642, 1985.

Klein et al, *Nature*, 327:70–73, 1987.

Klein et al., *Proc. Nat'l Acad. Sci. USA*, 85:8502–8505, 1988.

Kohler et al., *Eur. J. Immunol.* 6:511–519, 1976.

Kohler et al, *Nature* 256:495–497, 1975.

Konieczny et al, "A procedure for mapping *Arabidopsis* mutations using codominant ecotype-specific PCR-based markers," *The Plant Journal*, 4:403–410, 1993.

Koorneef et al., *Genetica*, 61:41–46, 1983.

Koorneef, "Linkage map of *Arabidopsis thaliana* (2n=10)," In S J O'Brien, ed, *Genetic Maps* 1987: A compilation of linkage and restriction maps of genetically studied organisms, 724–745, 1987.

Koorneef, "The use of telotrisomics for centromere mapping in *Arabidopsis thaliana* (L.) Heynh, *Genetica*, 62:3340, 1983.

Koster and Leopold, *Plant Physiol.*, 88:829–832, 1988.

Kuby, J., *Immunology* 2nd Edition, W. H. Freeman & Company, NY, 1994

Kyte et al, *A simple method for displaying the hydropathic character of a protein," J. Mol. Biol.* 157(1):105–132, 1982.

Lechner et al., "A 240 kd multisubunit protein complex, CBF3 is a major component of the budding yeast centromere," *Cell*, 64:717–725, 1991.

Lee and Saier, *J. of Bacteriol.*, 153–685, 1983.

Levings, *Science*, 250:942–947, 1990.

Lewin, *Genes II*, John Wiley & Sons, Publishers, N.Y., 1985.

Li et al., *P.N.A.S.*, 87:4580–4584, 1990.

Lieber and Strauss, "Selection of efficient cleavage sites in target RNAs by using a ribozyme expression library." *Mol. Cell. Biol.*, 15: 540–551, 1995.

Loomis et al., *J. Expt. Zoology*, 252:9–15, 1989.

Lorz et al., *Mol. Gen. Genet.*, 199:178, 1985.

Lu et al., "High efficiency retroviral mediated gene transduction into single isolated immature and replatable CD34(3+) hematopoietic stem/progenitor cells from human umbilical cord blood," *J. Exp. Med.* 178(6):2089–2096, 1993.

Maloy, S. R., "Experimental Techniques in Bacterial Genetics" Jones and Bartlett Prokop, A., and Bajpai, R. K. "Recombinant DNA Technology I" *Ann. N.Y. Acad. Sci.* vol. 646, 1991.

Maluszynaska et al., "Molecular cytogenetics of the genus *Arabidopsis*: In situ localization of rDNA sites, chromosome numbers and diversity in centromeric heterochromatin," *Annals Botany*, 71:479484, 1993.

Maluszynska et al., "Localization of tandemly repeated DNA sequences in *Arabidopsis thaliana*," *Plant Jour.*, 1(2): 159–166, 1991.

Maniatis et al, "Molecular Cloning: a Laboratory Manual," Cold Spring Harbor Laboratory, Cold Spring Harbor, N.Y., 1982.

Marcotte et al., *Nature*, 335:454, 1988.

Mariani et al., *Nature*, 347:737–741, 1990.

Martinez-Zapater et al., *Mol. Gen. Genet.*, 204:417–423, 1986.

McCabe et al, *Biotechnology*, 6:923, 1988.

Michel and Westhof, "Modeling of the three-dimensional architecture of group I catalytic introns based on comparative sequence analysis," *J. Mol. Biol.*, 216:585–610, 1990.

Mortimer et al., "Genetic mapping in *Saccharomyces cerevisiae*," Life Cycle and Inheritance, In: *The Molecular Biology of the Yeast Saccharomyces*, 11–26, 1981.

Mundy and Chua, *The EMBO J*, 7:2279–2286, 1988.

Murdock et al., *Phytochemistry*, 29:85–89, 1990.

Murray et al., *Nature*, 305:189–193, 1983.

Napoli, Lemieux, Jorgensen, "Introduction of a chimeric chalcone synthase gene into petunia results in reversible co-suppression of homologous genes in trans," *Plant Cell*, 2:279–289, 1990.

Nester, *Ann. Rev. Plant Phys.*, 35:387–413, 1984.

Nicklas, "The forces that move chromosomes in mitosis," *Annu. Rev. Biophys. Biophys. Chem.*, 17:431–39, 1988.

Nussbaum et al., *Proc. Nat'l Acad Sci USA*, 73:1068, 1976.

Omirulleh et al., *Plant Molecular Biology*, 21:415–428, 1993.

Palukaitis et al., "Characterization of a viroid associated with avacado sunblotch disease," *Virology*, 99:145–151, 1979.

Perkins, "The detection of linkage in tetrad analysis," *Genetics*, 38, 187–197, 1953.

Perlak et al., *Proc. Natl. Acad. Sci. USA*, 88:3324–3328, 1991.

Perriman et al., "Extended target-site specificity for a hammerhead ribozyme," *Gene*, 113:157–163, 1992.

Phi-Van et al., *Mol. Cell. Biol.*, 10:2302–2307. 1990.

Piatkowski et al., *Plant Physiol.*, 94:1682–1688, 1990.

Potrykus et al., *Mol. Gen. Genet.*, 199:183, 1985.

Preuss et al., "Tetrad analysis possible in *Arabidopsis* with mutation of the QUARTET (QRT) genes," *Science*, 264: 1458, 1994.

Price et al., "Systematic relationships of *Arabidopsis*: a molecular and morpohorical perspective", in: Somerville, C. and Meyerowitz, E. (eds.) *Arabidopsis*, Cold Spring Harbor Press, NY, 1995.

Prody et al., "Autolytic processing of dimeric plant virus satellite RNA." *Science*, 231:1577–1580, 1986.

Prokop et al., *Ann. N.Y. Acad. Sci.* 646, 1991

Rattner, "The structure of the mammalian centromere," *Bioassays*, 13(2):51–56, 1991.

Reed et al., *J. Gen. Microbiology*, 130:1–4, 1984.

Reinhold-Hurek and Shub, "Self-splicing introns in tRNA genes of widely divergent bacteria," *Nature*, 357:173–176, 1992.

Rensburg et al., *J. Plant Physiol.,* 141:188–194, 1993.

Richards et al., "The centromere region of *Arabidopsis thaliana* chromosome 1 contains telomere-similar sequences," *Nucleic Acids Research,* 19(12):3351–3357, 1991.

Rieder, "The formation, structure and composition of the mammalian kinetochore and kinetochore fiber," *Int. Rev. Cytol,* 79:1–58, 1982.

Rogers et al., *Meth. in Enzymol.,* 153:253–277, 1987.

Rosenberg et al, "RFLP subtraction: A method for making libraries of polymorphic markers," *Proc. Nat'l Acad. Sci. USA,* 91:6113–6117, 1994.

Schwartz et al., Cold Spring Harbor Symp. *Quant. Biol.,* 47, 195–198, 1982.

Sears et al., "Cytogenetic studies in *Arabidopsis thaliana,*" *Can. J. Genet. Cytol.,* 12:217–233, 1970.

Segal, "Biochemical Calculations" 2nd Edition. John Wiley & Sons, New York, 1976.

Setlow et al., *Genetic Engineering: Principles and Methods,* 1979.

Shagan and Bar-Zvi, *Plant Physiol.,* 101:1397–1398, 1993.

Shapiro, *In: Mobile Genetic Elements,* 1983.

Shingo et al., *Mol. Cell. Biol.,* 6:1787, 1986.

Smith, Watson, Bird, Ray, Schuch, Grierson, "Expression of a truncated tomato polygalacturonase gene inhibits expression of the endogenous gene in transgenic plants," *Mol Gen. Genet.,* 224:447–481, 1990.

Smithies et al., *Nature,* 317:230–234, 1985.

Smythe, "Pollen clusters," *Current Biology,* 4:851–853, 1994.

Spielmann et al., *Mol. Gen. Genet.,* 205:34, 1986.

Stiefel et al., *Nature,* 341:343, 1989.

Stinchcomb et al, *Nature,* 282:3943, 1979.

Stougaard, *The Plant Journal,* 3:755–761, 1993.

Symington et al., *Cell,* 52:237–240, 1988.

Symons, "Avacado sunblotch viroid: primary sequence and proposed secondary structure." *Nucl. Acids Res.,* 9:6527–6537, 1981.

Symons, "Small catalytic RNAs." *Annu. Rev. Biochem.,* 61:641–671, 1992.

Tarczynski et al., "Expression of a bacterial mtlD gene in transgenic tobacco leads to production and accumulation of mannitol," *Proc. Natl. Acad. Sci. USA,* 89:1–5, 1992.

Tarczynski et al., "Stress Protection of Transgenic Tobacco by Production of the Osmolyte Mannitol," *Science,* 259: 508–510, 1993.

Thomas et al., *Cell,* 44:419–428, 1986.

Thomas et al., *Proc. Nat 7 Acad. Sci. USA,* 71:4579, 1974.

Thompson et al., "Decreased expression of BRCA1 accelerates growth and is often present during sporadic breast cancer progression," Nature Genet., 9:444–450, 1995.

Toriyama et al., *Theor Appl. Genet.,* 73:16, 1986.

Tyler-Smith et al., "Mammalian chromosome structure," Current Biology, 3:390–397, 1993.

Uchimiya et al., *Mol. Gen. Genet.,* 204:204, 1986.

Van der Krol, Mur, Beld, Mol, Stuitje, "Flavonoid genes in petunia: addition of a limiting number of copies may lead to a suppression of gene expression," *Plant Cell,* 2:291–99, 1990.

Vasil et al., "Herbicide-resistant fertile transgenic wheat plants obtained by microprojectile bombardment of regenerable embryogenic callus," Biotechnology, 10:667–674, 1992.

Vasil, *Biotechnology,* 6:397, 1988.

Vernon and Bohnert, *The EMBO J,* 11:2077–2085, 1992.

Wagner et al., "Coupling of adenovirus to transferrin-polylysine/DNA complexes greatly enhances receptor-mediated gene delivery and expression of transfected genes," *Proc. Nat'l Acad. Sci. USA* 89 (13):6099–6103, 1992.

Watrud et al., *In: Engineered Organisms and the Environment,* 1985.

Watson et al., *Recombinant DNA: A Short Course,* 1983.

Weinsink et al., *Cell,* 3:315–325, 1974.

Wevrick et al., "Partial deletion of alpha satellite DNA association with reduced amounts of the centromere protein CENP-B in a mitotically stable human chromosome rearrangement," *Mol Cell Biol.,* 10:6374–6380, 1990.

Whitehouse, *Nature,* No. 4205: 893, 1950.

Wigler et al., *Cell,* 11:223, 1977.

Willard, H.,"Centromeres of mammalian chromosomes" *Trends Genet.,* 6:410–416, 1990.

Willard, H., *Nature Genetics* 15:345–354, 1997

Wolter et al., *The EMBO J,* 4685–4692, 1992.

Wong et al, "Electric field mediated gene transfer," *Biochim. Biophys. Res. Commun.* 107(2):584–587, 1982.

Xiang and Guerra, *Plant Physiol.,* 102:287–293, 1993.

Xu et al., *Plant Physiol.,* 110:249–257, 1996.

Yamada et al., *Plant Cell Rep.,* 4:85, 1986.

Yamaguchi-Shinozaki et al., *Plant Cell Physiol.,* 33:217–224, 1992.

Yen, *Embo J.* 10(5), 1245–1254, 1991.

Young et al., In: *Eukaryotic Genetic Systems ICN-UCLA Symposia on Molecular and Cellular Biology, VII,* 315–331, 1977.

Yuan and Altman, "Selection of guide sequences that direct efficient cleavage of mRNA by human ribonuclease P," *Science,* 263:1269–1273, 1994.

Yuan et al., "Targeted cleavage of mRNA by human RNase P," Proc. Natl. Acad. Sci. USA, 89:8 8010, 1992.

Zatloukal et al., "Transferrinfection: a highly efficient way to express gene constructs in eukaryotic cells," Ann. N.Y. Acad. Sci., 660:136–153, 1992.

What is claimed is:

1. A transgenic cell comprising an artificial plant chromosome, said artificial plant chromosome prepared by a method comprising the steps of:
   a) obtaining a nucleic acid molecule comprising *Arabidopsis thaliana* centromere DNA having the following characteristics:
      1) mapping to a location on an *Arabidopsis thaliana* chromosome defined by a pair of genetic markers selected from the group consisting of UFO and GAPB, m246 and m216, GL1 and TOPP5, GA1 and nga8, and nga76 and PhyC; and
      2) sorts DNA to the spindle poles in meiosis 1 in a pattern indicating the disjunction of homologous chromosomes
   b) preparing an artificial plant chromosome comprising said nucleic acid molecule; and
   c) transforming a recipient cell with said plant artificial chromosome.

2. A transgenic cell comprising an artificial plant chromosome, said artificial plant chromosome comprising *Arabidopsis thaliana* centromere DNA having the following characteristics:
   1) mapping to a location on an *Arabidopsis thaliana* chromosome defined by a pair of genetic markers selected from the group consisting of UFO and GAPB, m246 and m216, GL1 and TOPP5, GA1 and nga8, and nga76 and PhyC; and
   2) sorts DNA to the spindle poles in meiosis 1 in a pattern indicating the disjunction of homologous chromosomes.

3. The transgenic cell of claim 1 or 2, wherein said cell is a eukaryotic cell.

4. The transgenic cell of claim 3, wherein said cell is a plant cell.

5. The transgenic cell of claim 1, which has been transformed with said plant artificial chromosome, wherein said transforming comprises use of a method selected from the group consisting of *Agrobacterium*-mediated transformation, protoplast transformation, electroporation, or particle bombardment.

6. The transgenic cell of claim 1 or 2, wherein said plant artificial chromosome comprises a telomere.

7. The transgenic cell of claim 6, wherein said telomere is an *Arabidopsis thaliana* telomere.

8. The transgenic cell of claim 6, wherein said telomere is a yeast telomere.

9. The transgenic cell of claim 1 or 2, wherein said plant artificial chromosome comprises an autonomous replicating sequence (ARS).

10. The transgenic cell of claim 9, wherein said ARS is an *Arabidopsis thaliana* ARS.

11. The transgenic cell of claim 1 or 2, wherein said plant artificial chromosome comprises a selectable marker gene.

12. The transgenic cell of claim 1 or 2, wherein said plant artificial chromosome comprises a structural gene.

13. The transgenic cell of claim 12, wherein said structural gene is selected from the group consisting of an antibiotic resistance gene, a herbicide resistance gene, a nitrogen fixation gene, a plant pathogen defense gene, a plant stress-induced gene, a toxin gene, a seed storage gene, a hormone gene, an enzyme gene, an interleukin gene, a clotting factor gene, a cytokine gene, an antibody gene, and a growth factor gene.

14. A transgenic plant regenerated from the transgenic cell of claim 1 or 2.

15. The transgenic cell of claim 1 or 2, wherein said marker pair is m246 and m216.

16. The transgenic cell of claim 15, wherein said nucleic acid molecule is further defined as flanked by a genetic marker pair selected from the group consisting of m246 and THYIB, m246 and m497A, m497A and 84553, 84553 and RNS1, RNSI and Ve013, Ve013 and Cds3, Cds3 and mi310, mi310 and EKRII-C, EKRII-C and EKRII, EKRII and mi444, mi444 and mi421, mi421 and 84532, 84532 and SEP2A, SEP2A and 84133, 84133 and PR1, PR1 and mi398, and mi398 and m216.

\* \* \* \* \*

UNITED STATES PATENT AND TRADEMARK OFFICE
CERTIFICATE OF CORRECTION

PATENT NO.        : 7,015,372 B2                                        Page 1 of 1
APPLICATION NO. : 10/161849
DATED             : March 21, 2006
INVENTOR(S)       : Daphne Preuss et al.

It is certified that error appears in the above-identified patent and that said Letters Patent is hereby corrected as shown below:

In the Filing Date, please delete "Aug. 6, 2002" and insert --June 4, 2002--.

In the Inventors, please delete "Daphne Preuss" and insert --Daphne Kay Preuss--.

In the Inventors, please delete "Gregory Copenhaver" and insert --Gregory Paul Copenhaver--.

In Claim 1, pleas delete "thialiana" and insert --thaliana--.

In Claim 16, please delete "RNS1, RNSl" and insert --RNS1, RNS1--.

In Claim 16, please delete "84133,84133" and insert --84133, 84133--.

Signed and Sealed this

Ninth Day of January, 2007

JON W. DUDAS
*Director of the United States Patent and Trademark Office*